United States Patent
Van Leest et al.

(10) Patent No.: US 10,453,758 B2
(45) Date of Patent: Oct. 22, 2019

(54) METHOD AND APPARATUS TO DETERMINE A PATTERNING PROCESS PARAMETER USING AN ASYMMETRIC OPTICAL CHARACTERISTIC DISTRIBUTION PORTION

(71) Applicant: ASML NETHERLANDS B.V., Veldhoven (NL)

(72) Inventors: Adriaan Johan Van Leest, Eindhoven (NL); Anagnostis Tsiatmas, Eindhoven (NL); Paul Christiaan Hinnen, Veldhoven (NL); Elliott Gerard McNamara, Eindhoven (NL); Alok Verma, Eindhoven (NL); Thomas Theeuwes, Veldhoven (NL); Hugo Augustinus Joseph Cramer, Eindhoven (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 15/445,522

(22) Filed: Feb. 28, 2017

(65) Prior Publication Data
US 2017/0255737 A1    Sep. 7, 2017

Related U.S. Application Data

(60) Provisional application No. 62/458,932, filed on Feb. 14, 2017, provisional application No. 62/435,649,
(Continued)

(51) Int. Cl.
*G06F 17/50* (2006.01)
*H01L 21/66* (2006.01)
(Continued)

(52) U.S. Cl.
CPC .......... *H01L 22/12* (2013.01); *G01N 21/9501* (2013.01); *G03F 7/70633* (2013.01); *G03F 7/70683* (2013.01); *G03F 9/7003* (2013.01)

(58) Field of Classification Search
CPC ............. G03F 7/70633; G03F 7/70683; G03F 9/7003; G03F 7/705; G03F 7/70516;
(Continued)

(56) References Cited

U.S. PATENT DOCUMENTS 6,555,274 B1 *   4/2003   Kye .................... G03F 7/70283
                                                          430/5
7,791,727 B2     9/2010   Den Boef et al.
(Continued)

FOREIGN PATENT DOCUMENTS

WO   2009/078708   6/2009
WO   2009/100867   8/2009
(Continued)

OTHER PUBLICATIONS

Taiwanese Office Action issued in corresponding Taiwanese Patent Application No. 106106740, dated Aug. 10, 2018.
(Continued)

*Primary Examiner* — Nghia M Doan
(74) *Attorney, Agent, or Firm* — Pillsbury Winthrop Shaw Pittman LLP

(57) ABSTRACT

A method of determining a parameter of a patterning process, the method including: obtaining a detected representation of radiation redirected by a structure having geometric symmetry at a nominal physical configuration, wherein the detected representation of the radiation was obtained by illuminating a substrate with a radiation beam such that a beam spot on the substrate was filled with the structure; and determining, by a hardware computer system, a value of the patterning process parameter based on optical characteristic
(Continued)

values from an asymmetric optical characteristic distribution portion of the detected radiation representation with higher weight than another portion of the detected radiation representation, the asymmetric optical characteristic distribution arising from a different physical configuration of the structure than the nominal physical configuration.

29 Claims, 25 Drawing Sheets

Related U.S. Application Data filed on Dec. 16, 2016, provisional application No. 62/435,662, filed on Dec. 16, 2016, provisional application No. 62/435,670, filed on Dec. 16, 2016, provisional application No. 62/435,630, filed on Dec. 16, 2016, provisional application No. 62/301,880, filed on Mar. 1, 2016.

(51) Int. Cl.
  *G03F 9/00* (2006.01)
  *G01N 21/95* (2006.01)
  *G03F 7/20* (2006.01)

(58) Field of Classification Search
  CPC ............ G03F 7/70616; G03F 7/70625; G03F 7/70641; G03F 7/7065; G03F 7/7085; G06F 17/5009; G06F 17/5072; G06F 17/5081; G06F 2217/12; G06F 17/50; G06F 19/12
  USPC .................................... 716/50–56; 430/5, 30
  See application file for complete search history.

(56) References Cited

U.S. PATENT DOCUMENTS

| | | |
|---|---|---|
| 7,791,732 B2 | 9/2010 | Den Boef et al. |
| 8,339,595 B2 | 12/2012 | Den Boef |
| 8,411,287 B2 | 4/2013 | Smilde et al. |
| 8,705,007 B2 | 4/2014 | Cramer et al. |
| 8,867,020 B2 | 10/2014 | Smilde et al. |
| 9,081,303 B2 | 7/2015 | Cramer et al. |
| 9,110,385 B2 | 8/2015 | Den Boef |
| 2005/0185174 A1 | 8/2005 | Laan et al. |
| 2006/0033921 A1 | 2/2006 | Den Boef et al. |
| 2006/0065625 A1* | 3/2006 | Abdulhalim ........ G03F 7/70633 216/59 |
| 2006/0066855 A1 | 3/2006 | Den Boef et al. |
| 2006/0146310 A1* | 7/2006 | De Kruif ............ G03F 7/70558 355/69 |
| 2008/0218610 A1 | 9/2008 | Chapman et al. |
| 2009/0087756 A1 | 4/2009 | Schulz |
| 2009/0224413 A1 | 9/2009 | Ghinovker |
| 2010/0201963 A1 | 8/2010 | Cramer et al. |
| 2010/0328655 A1 | 12/2010 | Den Boef |
| 2011/0027704 A1 | 2/2011 | Cramer et al. |
| 2011/0043791 A1 | 2/2011 | Smilde et al. |
| 2011/0069292 A1 | 3/2011 | Den Boef |
| 2012/0227014 A1 | 9/2012 | Pforr |
| 2012/0242970 A1 | 9/2012 | Smilde et al. |
| 2013/0135600 A1 | 5/2013 | Middlebrooks et al. |
| 2013/0208279 A1* | 8/2013 | Smith .................... G01B 11/26 356/401 |
| 2015/0185625 A1 | 7/2015 | Chen et al. |

FOREIGN PATENT DOCUMENTS

| | | |
|---|---|---|
| WO | 2009/106279 | 9/2009 |
| WO | 2010034674 | 4/2010 |
| WO | 2011151121 | 12/2011 |
| WO | 2014/062972 | 4/2014 |
| WO | 2015/009619 | 1/2015 |
| WO | 2015/082158 | 6/2015 |
| WO | 2015/090838 | 6/2015 |

OTHER PUBLICATIONS

Taiwan Office Action dated Jan. 26, 2018 in corresponding Taiwan Patent Application No. 106106741.
Non-Final Office Action dated Mar. 9, 2018 in corresponding U.S. Appl. No. 15/445,465.
International Search Report and Written Opinion dated Apr. 24, 2017 in corresponding International Patent Application No. PCT/US2017/054714.
International Search Report and Written Opinion dated Apr. 24, 2017 in corresponding International Patent Application No. PCT/EP2017/054748.
International Search Report and Written Opinion dated May 9, 2017 in corresponding International Patent Application No. PCT/EP2017/054719.
International Search Report and Written Opinion dated Apr. 7, 2017 in corresponding International Patent Application No. PCT/EP2017/054761.
U.S. Office Action issued in corresponding U.S. Appl. No. 15/445,465, dated Feb. 21, 2019.
U.S. Office Action issued in corresponding U.S. Appl. No. 15/445,536, dated Dec. 3, 2018.
U.S. Office Action issued in corresponding U.S. Appl. No. 15/445,478, dated Nov. 29, 2018.
Final Office Action issued in corresponding U.S. Appl. No. 15/445,478, dated Jun. 13, 2019.

* cited by examiner

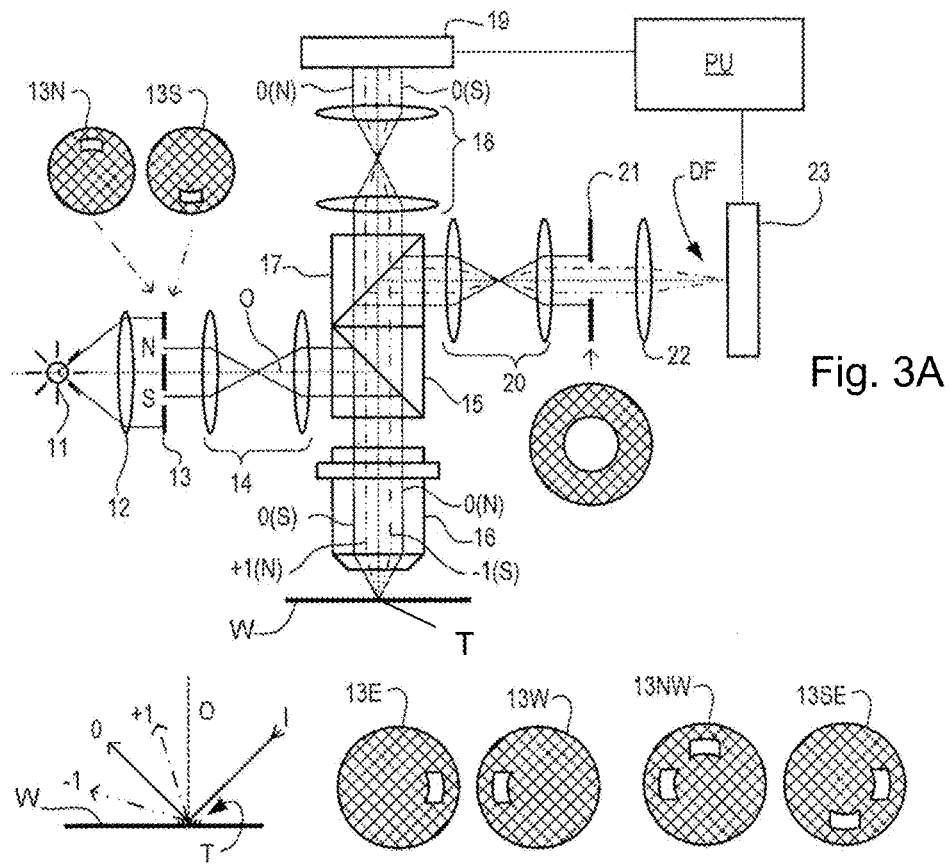
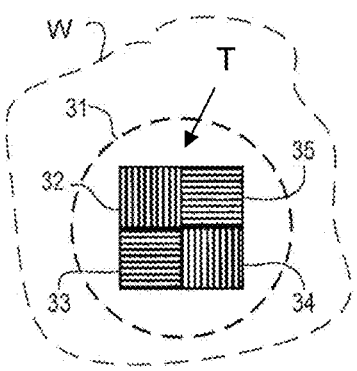 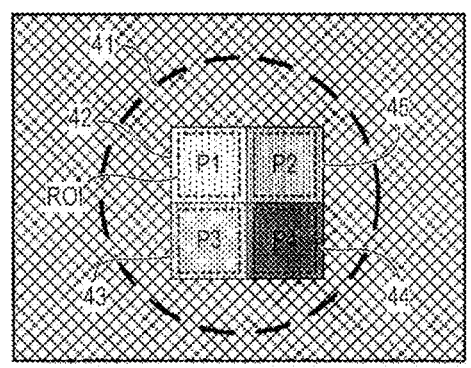
Fig. 4  Fig. 5

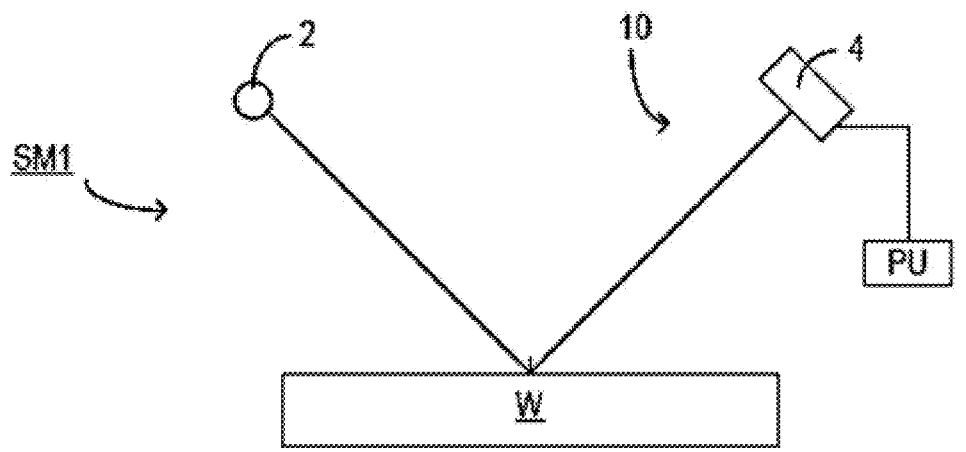
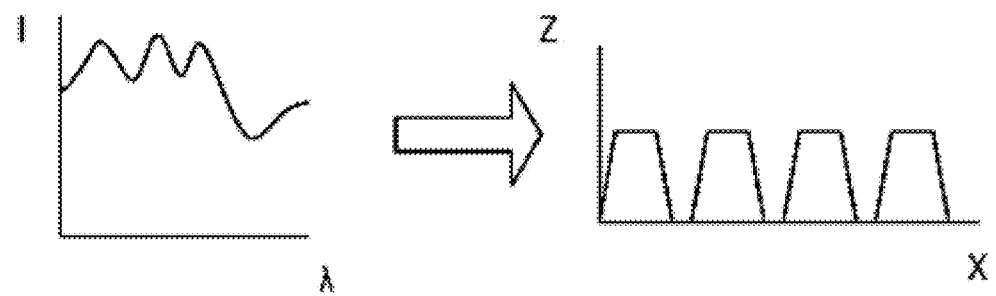
Fig. 6

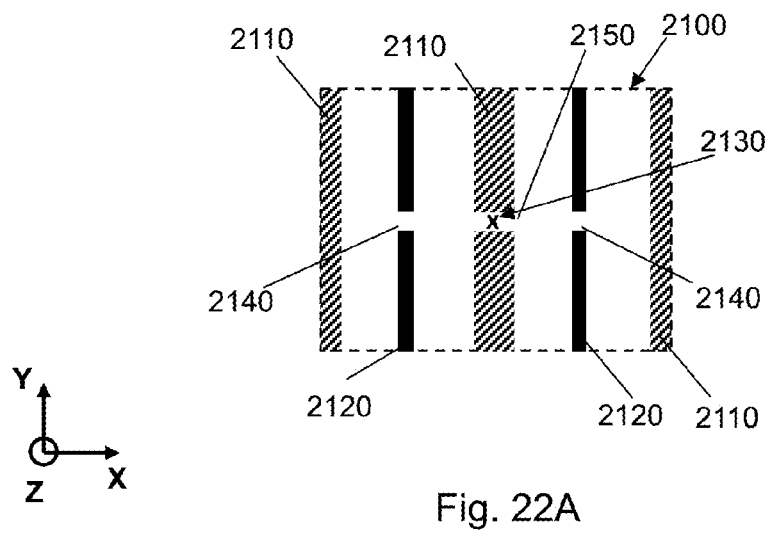
Fig. 22A
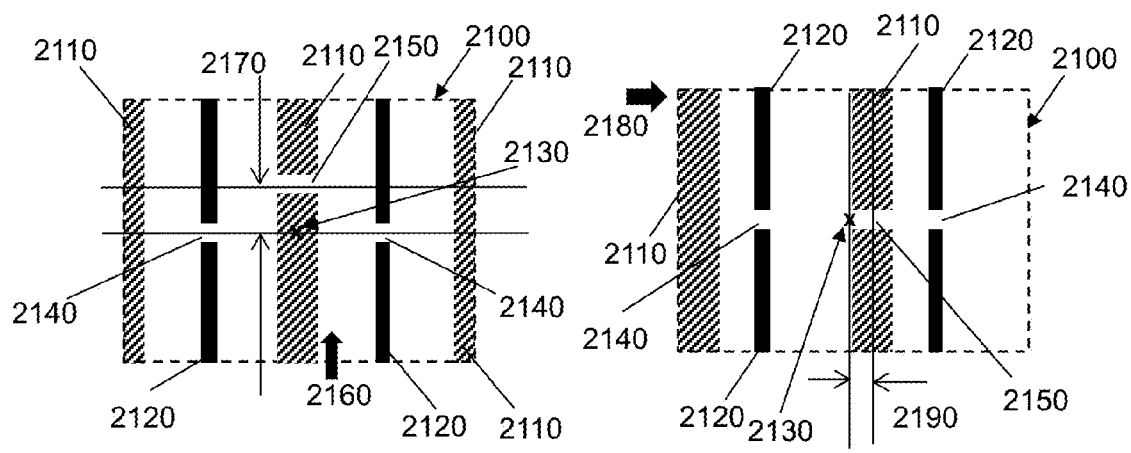
Fig. 22B
Fig. 22C

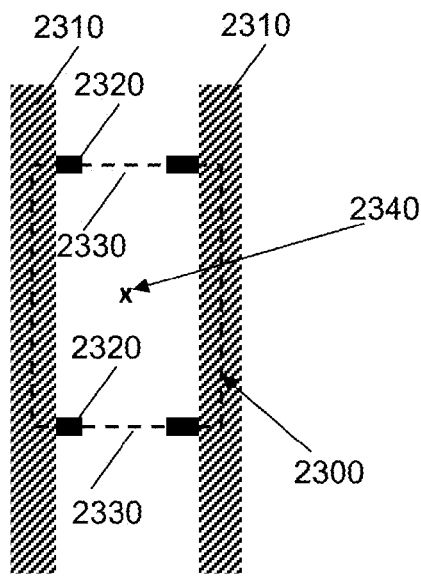
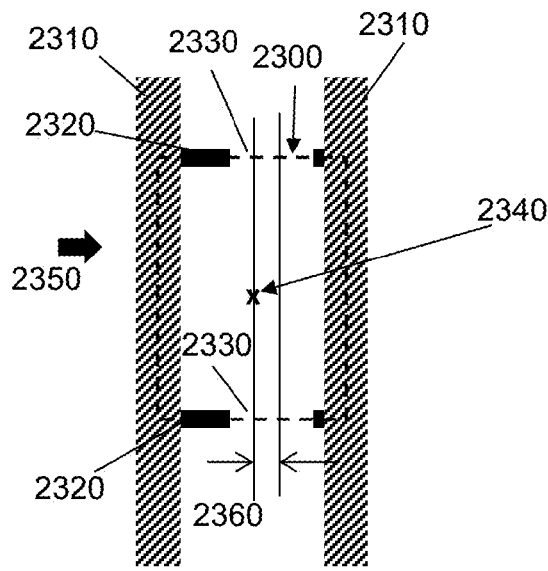
Fig. 23A      Fig. 23B
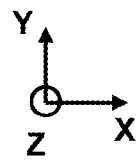
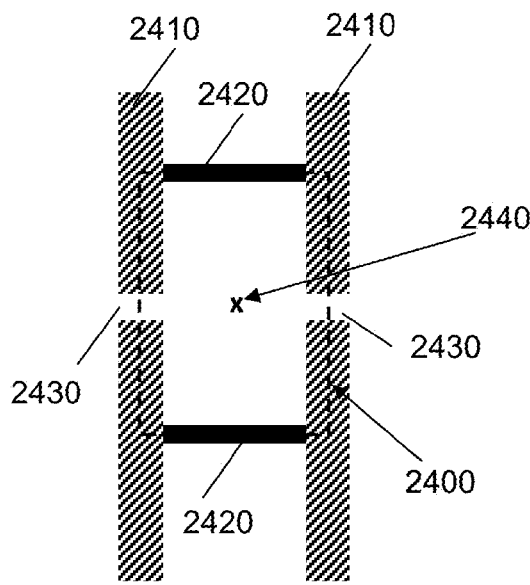
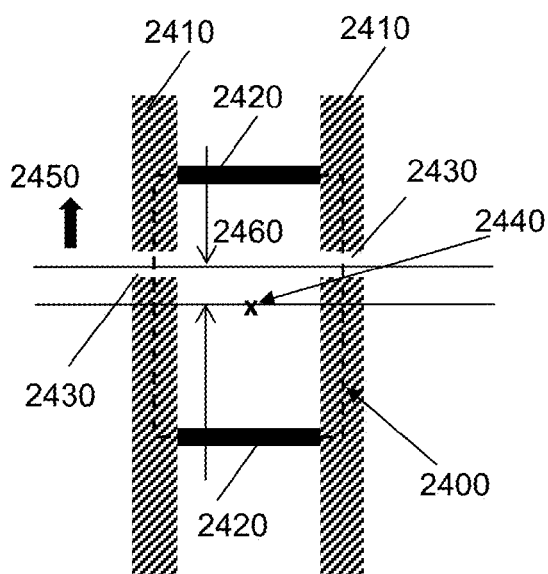
Fig. 24A      Fig. 24B

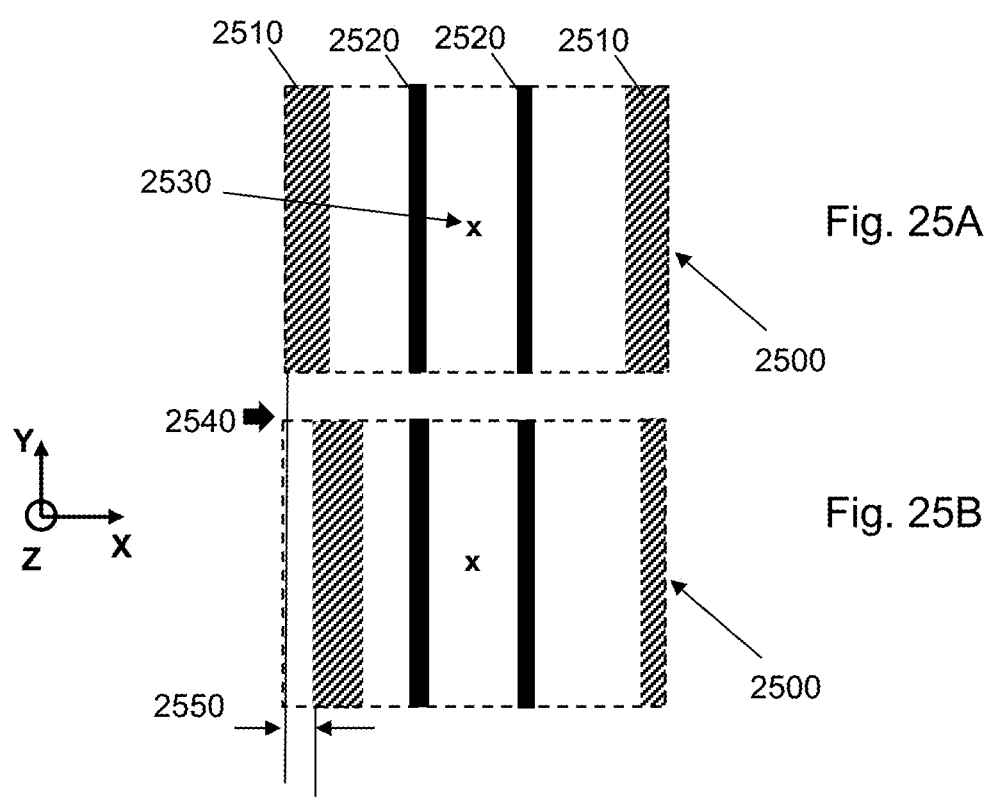

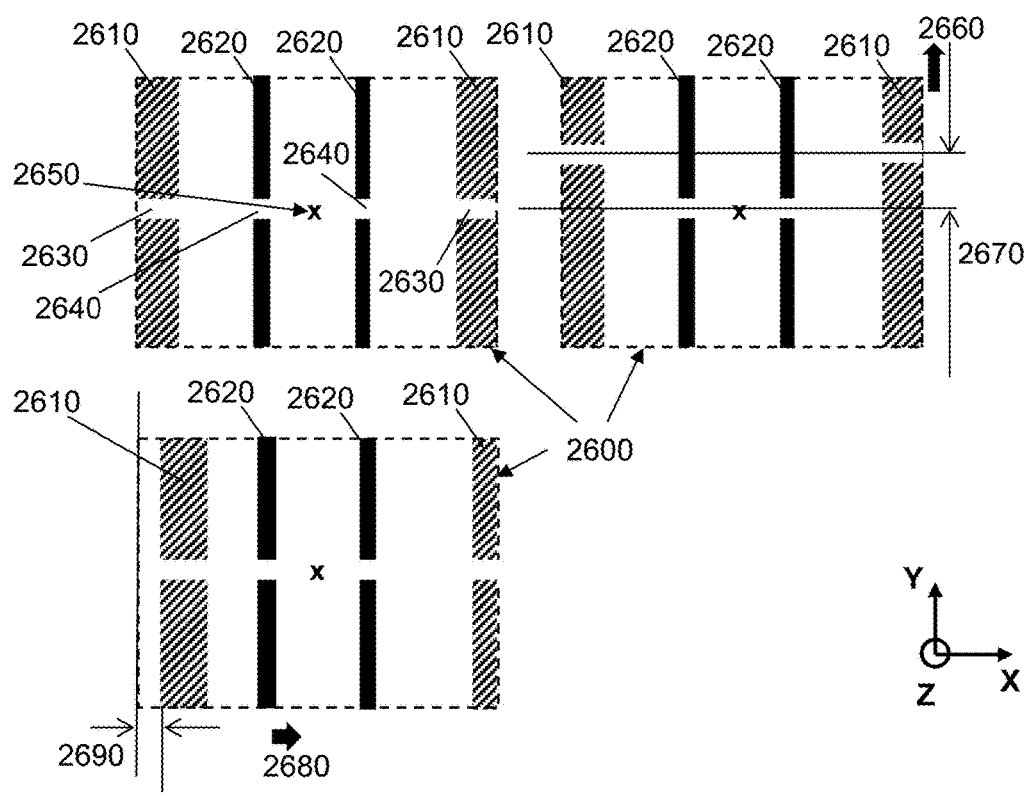

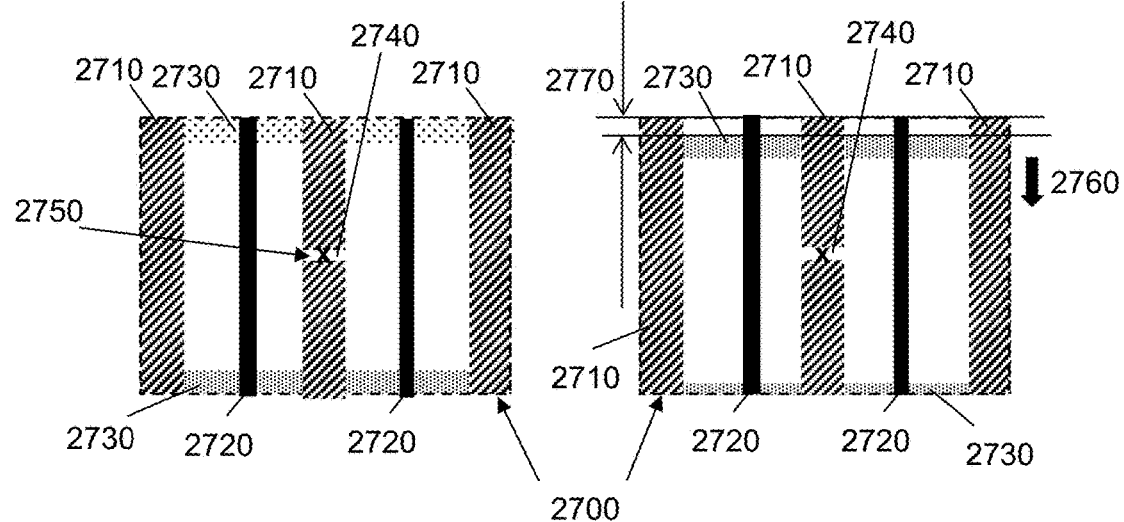
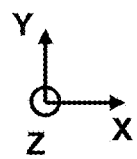
Fig. 27A   Fig. 27B
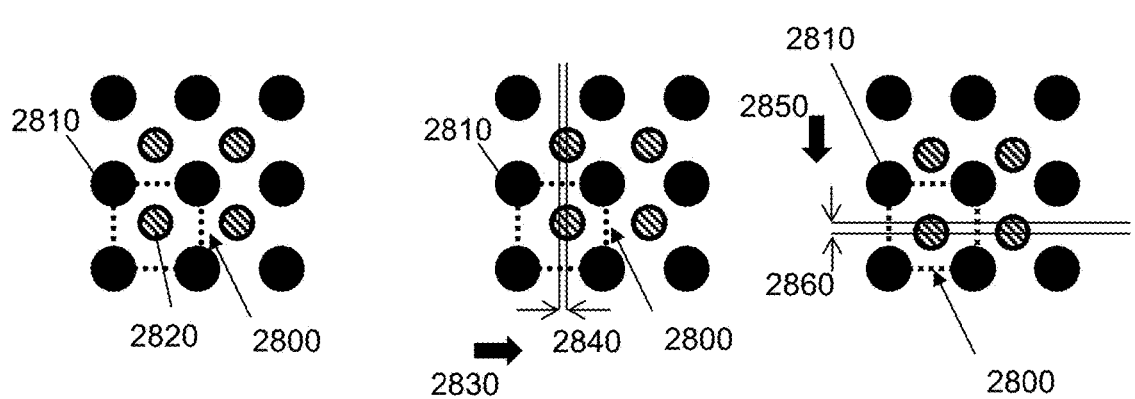
Fig. 28A   Fig. 28B   Fig. 28C

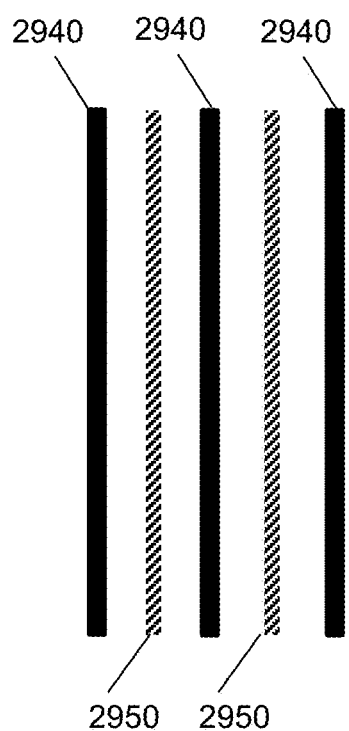
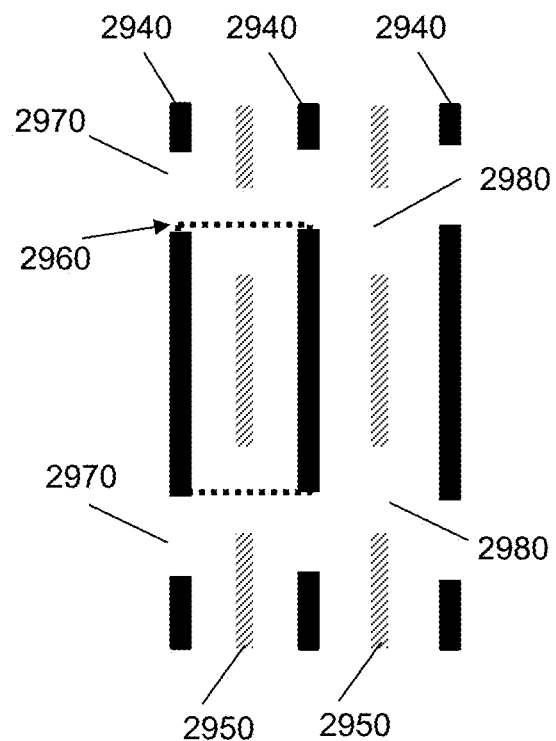
Fig. 29F          Fig. 29G
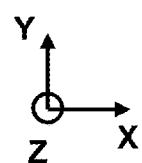

METHOD AND APPARATUS TO DETERMINE A PATTERNING PROCESS PARAMETER USING AN ASYMMETRIC OPTICAL CHARACTERISTIC DISTRIBUTION PORTION

This application claims priority under 35 USC § 119(e) to U.S. Provisional Patent Application No. 62/301,880, filed Mar. 1, 2016, to U.S. Provisional Patent Application No. 62/435,662, filed Dec. 16, 2016, to U.S. Provisional Patent Application No. 62/435,670, filed Dec. 16, 2016, to U.S. Provisional Patent Application No. 62/435,649, filed Dec. 16, 2016, to U.S. Provisional Patent Application No. 62/435,630, filed Dec. 16, 2016 and to U.S. Provisional Patent Application No. 62/458,932, filed Feb. 14, 2017, each of the foregoing applications incorporated herein its entirety by reference.

FIELD

The present description relates to a method and apparatus to determine a parameter (such as overlay) of a process, for example, to create a pattern on a substrate and which determined parameter can be used to design, monitor, adjust, etc. one or more variables related to the processing.

BACKGROUND

A lithographic apparatus is a machine that applies a desired pattern onto a substrate, usually onto a target portion of the substrate. A lithographic apparatus can be used, for example, in the manufacture of integrated circuits (ICs) or other devices designed to be functional. In that instance, a patterning device, which is alternatively referred to as a mask or a reticle, may be used to generate a circuit pattern to be formed on an individual layer of the device designed to be functional. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti parallel to this direction. It is also possible to transfer the pattern from the patterning device to the substrate by imprinting the pattern onto the substrate.

SUMMARY

Manufacturing devices, such as semiconductor devices, typically involves processing a substrate (e.g., a semiconductor wafer) using a number of fabrication processes to form various features and often multiple layers of the devices. Such layers and/or features are typically manufactured and processed using, e.g., deposition, lithography, etch, chemical-mechanical polishing, and ion implantation. Multiple devices may be fabricated on a plurality of dies on a substrate and then separated into individual devices. This device manufacturing process may be considered a patterning process. A patterning process involves a pattern transfer step, such as optical and/or nanoimprint lithography using a lithographic apparatus, to provide a pattern on a substrate and typically, but optionally, involves one or more related pattern processing steps, such as resist development by a development apparatus, baking of the substrate using a bake tool, etching the pattern by an etch apparatus, etc. Further, one or more metrology processes are involved in the patterning process.

Metrology processes are used at various steps during a patterning process to monitor and/or control the process. For example, metrology processes are used to measure one or more characteristics of a substrate, such as a relative location (e.g., registration, overlay, alignment, etc.) or dimension (e.g., line width, critical dimension (CD), thickness, etc.) of features formed on the substrate during the patterning process, such that, for example, the performance of the patterning process can be determined from the one or more characteristics. If the one or more characteristics are unacceptable (e.g., out of a predetermined range for the characteristic(s)), one or more variables of the patterning process may be designed or altered, e.g., based on the measurements of the one or more characteristics, such that substrates manufactured by the patterning process have an acceptable characteristic(s).

With the advancement of lithography and other patterning process technologies, the dimensions of functional elements have continually been reduced while the amount of the functional elements, such as transistors, per device has been steadily increased over decades. In the meanwhile, the requirement of accuracy in terms of overlay, critical dimension (CD), etc. has become more and more stringent. Error, such as error in overlay, error in CD, etc., will inevitably be produced in the patterning process. For example, imaging error may be produced from optical aberration, patterning device heating, patterning device error, and/or substrate heating and can be characterized in terms of, e.g., overlay, CD, etc. Additionally or alternatively, error may be introduced in other parts of the patterning process, such as in etch, development, bake, etc. and similarly can be characterized in terms of, e.g., overlay, CD, etc. The error may cause a problem in terms of the functioning of the device, including failure of the device to function or one or more electrical problems of the functioning device. Accordingly, it is desirable to be able to characterize one or more these errors and take steps to design, modify, control, etc. a patterning process to reduce or minimize one or more of these errors.

In an embodiment, there is provided a method of determining a parameter of a patterning process, the method comprising: obtaining a detected representation of radiation redirected by a structure having geometric symmetry at a nominal physical configuration, wherein the detected representation of the radiation was obtained by illuminating a substrate with a radiation beam such that a beam spot on the substrate was filled with the structure; and determining, by a hardware computer system, a value of the patterning process parameter based on optical characteristic values from an asymmetric optical characteristic distribution portion of the detected radiation representation with higher weight than another portion of the detected radiation representation, the asymmetric optical characteristic distribution arising from a different physical configuration of the structure than the nominal physical configuration.

In an embodiment, there is provided a method of determining overlay of a patterning process, the method comprising: obtaining a detected representation of radiation redirected by a structure having geometric symmetry at a nominal overlay value, wherein the detected representation of the radiation was obtained by illuminating a substrate with a radiation beam such that a beam spot on the substrate was filled with the structure and wherein, at a non-nominal value of the overlay, the physical configuration of the structure causes an asymmetric optical characteristic distribution in the detected radiation representation; and determining, by a hardware computer system, a non-nominal value of the overlay of the structure based on a summation for a plurality of pixels of the detected radiation representation of an optical characteristic value for each pixel multiplied by an associated weighting for that pixel, wherein the weighting for pixels in the asymmetric optical characteristic distribution are different than the weighting for pixels in a symmetric optical characteristic distribution portion of the detected radiation representation.

In an embodiment, there is provided a method comprising: obtaining a detected representation of radiation redirected by a structure that has geometric symmetry at a nominal physical configuration, wherein a different physical configuration of the structure than the nominal physical configuration causes an asymmetric optical characteristic distribution in the detected representation and a patterning process parameter measures change in the physical configuration; and determining, by a hardware computer system, a value of the patterning process parameter at the different physical configuration using a reconstruction process that processes optical characteristic values derived from the detected representation.

In an embodiment, there is provided a method comprising: obtaining a detected representation of radiation redirected by a structure that has geometric symmetry at a nominal physical configuration, wherein a different physical configuration of the structure than the nominal physical configuration causes an asymmetric optical characteristic distribution in the detected representation and a patterning process parameter measures change in the physical configuration; and determining, by a hardware computer system, a value of the patterning process parameter at the different physical configuration using a non-linear solver that processes optical characteristic values derived from the detected representation.

In an aspect, there is provided a non-transitory computer program product comprising machine-readable instructions for causing a processor system to cause performance of a method described herein. In an aspect, there is provided a computer program product comprising a computer non-transitory readable medium having instructions recorded thereon, the instructions when executed by a computer implementing a method or one or more process steps described herein.

In an aspect, there is provided a metrology apparatus for measuring an object of a patterning process, the metrology apparatus configured to perform a method as described herein. In an aspect, there is provided an inspection apparatus for inspecting an object of a patterning process, the inspection apparatus being operable to perform a method as described herein.

In an aspect, there is provided a system comprising: a metrology apparatus configured to provide a beam of radiation onto an object surface and to detect radiation redirected by the structure on the object surface; and a computer program product as described herein. In an embodiment, the system further comprises a lithographic apparatus comprising a support structure configured to hold a patterning device to modulate a radiation beam and a projection optical system arranged to project the modulated radiation beam onto a radiation-sensitive substrate, wherein the object is the substrate.

In an embodiment, there is provided a system comprising: a hardware processor system; and a non-transitory computer readable storage medium configured to store machine-readable instructions, wherein when executed, the machine-readable instructions cause the hardware processor system to perform a method as described herein.

BRIEF DESCRIPTION OF THE DRAWINGS

Embodiments will now be described, by way of example only, with reference to the accompanying drawings in which:

FIG. 3A is schematic diagram of a measurement apparatus for use in measuring targets according to an embodiment using a first pair of illumination apertures providing certain illumination modes;

FIG. 3B is a schematic detail of a diffraction spectrum of a target for a given direction of illumination;

FIG. 3C is a schematic illustration of a second pair of illumination apertures providing further illumination modes in using a measurement apparatus for diffraction based overlay measurements;

FIG. 3D is a schematic illustration of a third pair of illumination apertures combining the first and second pairs of apertures providing further illumination modes in using a measurement apparatus for diffraction based overlay measurements;

FIG. 4 schematically depicts a form of multiple periodic structure (e.g., multiple grating) target and an outline of a measurement spot on a substrate;

FIG. 5 schematically depicts an image of the target of FIG. 4 obtained in the apparatus of FIG. 3;

FIG. 6 schematically depicts an example metrology apparatus and metrology technique;

FIG. 22A, FIG. 22B, FIG. 22C and FIG. 22D schematically depict examples of a non-product target design;

FIG. 23A and FIG. 23B schematically depict an example of a non-product target design;

FIG. 24A and FIG. 24B schematically depict an example of a non-product target design;

FIG. 25A and FIG. 25B schematically depict an example of a non-product target design;

FIG. 26A, FIG. 26B and FIG. 26C schematically depict an example of a non-product target design;

FIG. 27A and FIG. 27B schematically depict an example of a non-product target design;

FIG. 28A, FIG. 28B and FIG. 28C schematically depict an example of a non-product target design;

FIG. 29F schematically depicts an example of structures of a non-product target design corresponding to the steps of FIGS. 29B and 29D;

FIG. 29G schematically depicts an example of a non-product target design created from the structures of FIG. 29F;

DETAILED DESCRIPTION

Before describing embodiments in detail, it is instructive to present an example environment in which embodiments may be implemented.

Figure 1:
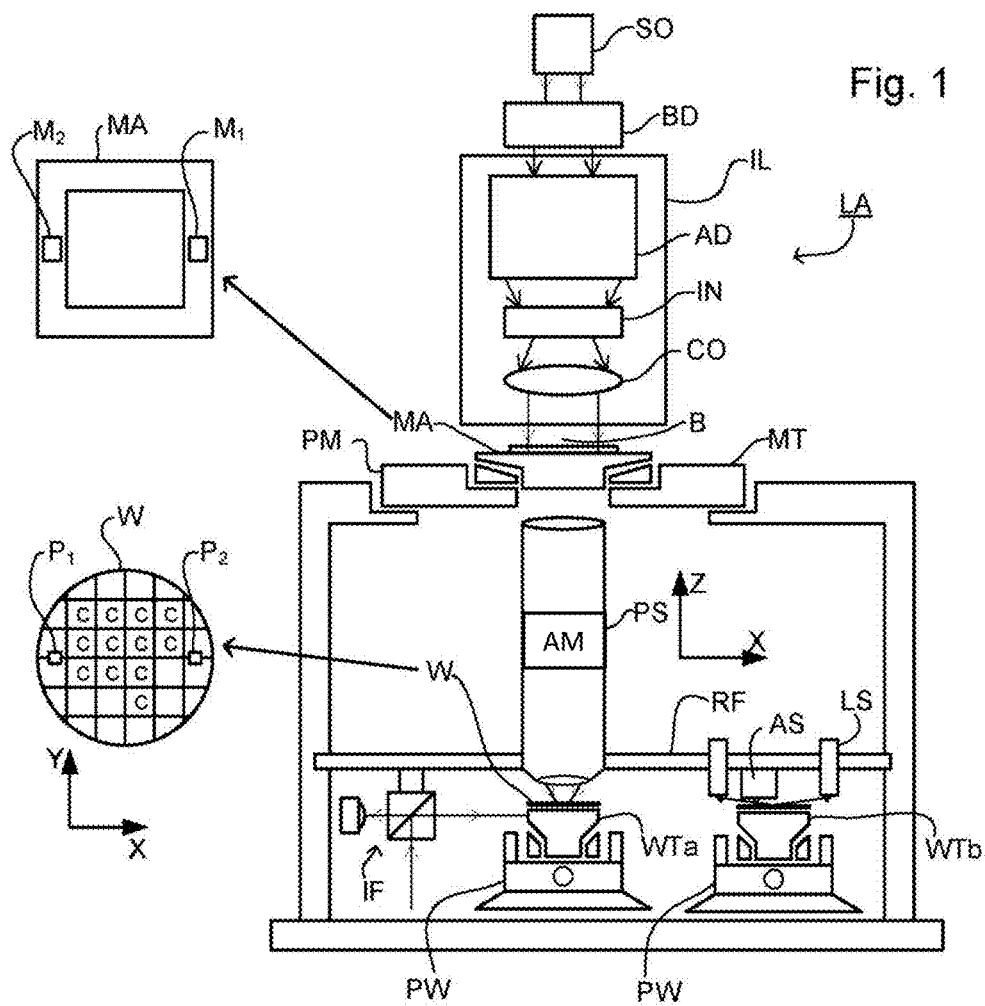
FIG. 1 schematically depicts an embodiment of a lithographic apparatus.

FIG. 1 schematically depicts a lithographic apparatus LA. The apparatus comprises:

an illumination system (illuminator) IL configured to condition a radiation beam B (e.g. UV radiation or DUV radiation);

a support structure (e.g. a mask table) MT constructed to support a patterning device (e.g. a mask) MA and connected to a first positioner PM configured to accurately position the patterning device in accordance with certain parameters;

a substrate table (e.g. a wafer table) WT constructed to hold a substrate (e.g. a resist-coated wafer) W and connected to a second positioner PW configured to accurately position the substrate in accordance with certain parameters; and a projection system (e.g. a refractive projection lens system) PS configured to project a pattern imparted to the radiation beam B by patterning device MA onto a target portion C (e.g. comprising one or more dies) of the substrate W, the projection system supported on a reference frame (RF).

The illumination system may include various types of optical components, such as refractive, reflective, magnetic, electromagnetic, electrostatic or other types of optical components, or any combination thereof, for directing, shaping, or controlling radiation.

The support structure supports the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a pattern in a target portion of the substrate. In an embodiment, a patterning device is any device that can be used to impart a radiation beam with a pattern in its cross-section so as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

The projection system PS has an optical transfer function which may be non-uniform, which can affect the pattern imaged on the substrate W. For unpolarized radiation such effects can be fairly well described by two scalar maps, which describe the transmission (apodization) and relative phase (aberration) of radiation exiting the projection system PS as a function of position in a pupil plane thereof. These scalar maps, which may be referred to as the transmission map and the relative phase map, may be expressed as a linear combination of a complete set of basis functions. A particularly convenient set is the Zernike polynomials, which form a set of orthogonal polynomials defined on a unit circle. A determination of each scalar map may involve determining the coefficients in such an expansion. Since the Zernike polynomials are orthogonal on the unit circle, the Zernike coefficients may be determined by calculating the inner product of a measured scalar map with each Zernike polynomial in turn and dividing this by the square of the norm of that Zernike polynomial.

The transmission map and the relative phase map are field and system dependent. That is, in general, each projection system PS will have a different Zernike expansion for each field point (i.e. for each spatial location in its image plane). The relative phase of the projection system PS in its pupil plane may be determined by projecting radiation, for example from a point-like source in an object plane of the projection system PS (i.e. the plane of the patterning device MA), through the projection system PS and using a shearing interferometer to measure a wavefront (i.e. a locus of points with the same phase). A shearing interferometer is a common path interferometer and therefore, advantageously, no secondary reference beam is required to measure the wavefront. The shearing interferometer may comprise a diffraction grating, for example a two dimensional grid, in an image plane of the projection system (i.e. the substrate table WT) and a detector arranged to detect an interference pattern in a plane that is conjugate to a pupil plane of the projection system PS. The interference pattern is related to the derivative of the phase of the radiation with respect to a coordinate in the pupil plane in the shearing direction. The detector may comprise an array of sensing elements such as, for example, charge coupled devices (CCDs).

The projection system PS of a lithography apparatus may not produce visible fringes and therefore the accuracy of the determination of the wavefront can be enhanced using phase stepping techniques such as, for example, moving the diffraction grating. Stepping may be performed in the plane of the diffraction grating and in a direction perpendicular to the scanning direction of the measurement. The stepping range may be one grating period, and at least three (uniformly distributed) phase steps may be used. Thus, for example, three scanning measurements may be performed in the y-direction, each scanning measurement being performed for a different position in the x-direction. This stepping of the diffraction grating effectively transforms phase variations into intensity variations, allowing phase information to be determined. The grating may be stepped in a direction perpendicular to the diffraction grating (z direction) to calibrate the detector.

The transmission (apodization) of the projection system PS in its pupil plane may be determined by projecting radiation, for example from a point-like source in an object plane of the projection system PS (i.e. the plane of the patterning device MA), through the projection system PS and measuring the intensity of radiation in a plane that is conjugate to a pupil plane of the projection system PS, using a detector. The same detector as is used to measure the wavefront to determine aberrations may be used.

The projection system PS may comprise a plurality of optical (e.g., lens) elements and may further comprise an adjustment mechanism AM configured to adjust one or more of the optical elements so as to correct for aberrations (phase variations across the pupil plane throughout the field). To achieve this, the adjustment mechanism may be operable to manipulate one or more optical (e.g., lens) elements within the projection system PS in one or more different ways. The projection system may have a co-ordinate system wherein its optical axis extends in the z direction. The adjustment mechanism may be operable to do any combination of the following: displace one or more optical elements; tilt one or more optical elements; and/or deform one or more optical elements. Displacement of an optical element may be in any direction (x, y, z or a combination thereof), Tilting of an optical element is typically out of a plane perpendicular to the optical axis, by rotating about an axis in the x and/or y directions although a rotation about the z axis may be used for a non-rotationally symmetric aspherical optical element. Deformation of an optical element may include a low frequency shape (e.g. astigmatic) and/or a high frequency shape (e.g. free form aspheres). Deformation of an optical element may be performed for example by using one or more actuators to exert force on one or more sides of the optical element and/or by using one or more heating elements to heat one or more selected regions of the optical element. In general, it may not be possible to adjust the projection system PS to correct for apodization (transmission variation across the pupil plane). The transmission map of a projection system PS may be used when designing a patterning device (e.g., mask) MA for the lithography apparatus LA. Using a computational lithography technique, the patterning device MA may be designed to at least partially correct for apodization.

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more tables (e.g., two or more substrate tables WTa, WTb, two or more patterning device tables, a substrate table WTa and a table WTb below the projection system without a substrate that is dedicated to, for example, facilitating measurement, and/or cleaning, etc.). In such "multiple stage" machines the additional tables may be used in parallel, or preparatory steps may be carried out on one or more tables while one or more other tables are being used for exposure. For example, alignment measurements using an alignment sensor AS and/or level (height, tilt, etc.) measurements using a level sensor LS may be made.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the patterning device and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD configured to adjust the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask) MA, which is held on the support structure (e.g., mask table) MT, and is patterned by the patterning device. Having traversed the patterning device MA, the radiation beam B passes through the projection system PS, which focuses the beam onto a target portion C of the substrate W. With the aid of the second positioner PW and position sensor IF (e.g. an interferometric device, linear encoder, 2-D encoder or capacitive sensor), the substrate table WT can be moved accurately, e.g. so as to position different target portions C in the path of the radiation beam B. Similarly, the first positioner PM and another position sensor (which is not explicitly depicted in FIG. 1) can be used to accurately position the patterning device MA with respect to the path of the radiation beam B, e.g. after mechanical retrieval from a mask library, or during a scan. In general, movement of the support structure MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the support structure MT may be connected to a short-stroke actuator only, or may be fixed. Patterning device MA and substrate W may be aligned using patterning device alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device MA, the patterning device alignment marks may be located between the dies.

The depicted apparatus could be used in at least one of the following modes:

1. In step mode, the support structure MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the support structure MT and the substrate table WT are scanned synchronously while a pattern imparted to the radiation beam is projected onto a target portion C (i.e. a single dynamic exposure). The velocity and direction of the substrate table WT relative to the support structure MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the support structure MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
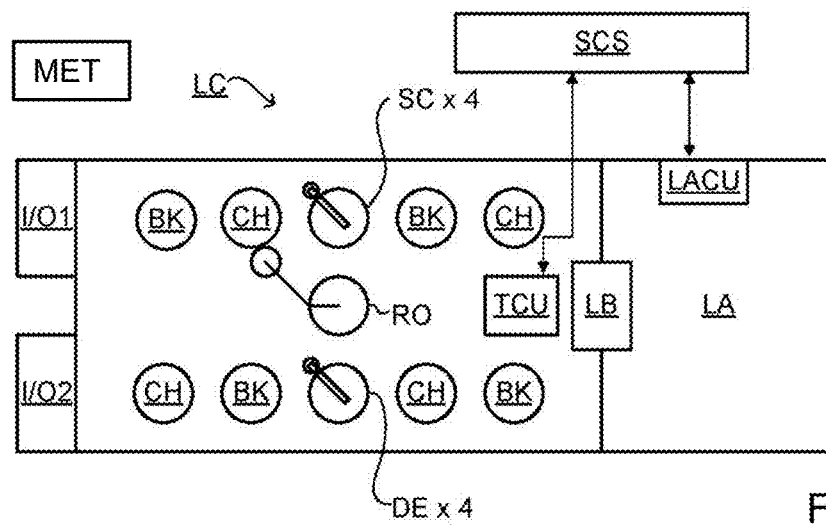
FIG. 2 schematically depicts an embodiment of a lithographic cell or cluster.

As shown in FIG. 2, the lithographic apparatus LA may form part of a lithographic cell LC, also sometimes referred to a lithocell or cluster, which also includes apparatuses to perform pre- and post-exposure processes on a substrate. Conventionally these include one or more spin coaters SC to deposit one or more resist layers, one or more developers DE to develop exposed resist, one or more chill plates CH and/or one or more bake plates BK. A substrate handler, or robot, RO picks up one or more substrates from input/output port I/O1, I/O2, moves them between the different process apparatuses and delivers them to the loading bay LB of the lithographic apparatus. These apparatuses, which are often collectively referred to as the track, are under the control of a track control unit TCU which is itself controlled by the supervisory control system SCS, which also controls the lithographic apparatus via lithography control unit LACU. Thus, the different apparatuses can be operated to maximize throughput and processing efficiency.

In order that a substrate that is exposed by the lithographic apparatus is exposed correctly and consistently, it is desirable to inspect an exposed substrate to measure or determine one or more properties such as overlay (which can be, for example, between structures in overlying layers or between structures in a same layer that have been provided separately to the layer by, for example, a double patterning process), line thickness, critical dimension (CD), focus offset, a material property, etc. Accordingly a manufacturing facility in which lithocell LC is located also typically includes a metrology system MET which receives some or all of the substrates W that have been processed in the lithocell. The metrology system MET may be part of the lithocell LC, for example it may be part of the lithographic apparatus LA.

Metrology results may be provided directly or indirectly to the supervisory control system SCS. If an error is detected, an adjustment may be made to exposure of a subsequent substrate (especially if the inspection can be done soon and fast enough that one or more other substrates of the batch are still to be exposed) and/or to subsequent exposure of the exposed substrate. Also, an already exposed substrate may be stripped and reworked to improve yield, or discarded, thereby avoiding performing further processing on a substrate known to be faulty. In a case where only some target portions of a substrate are faulty, further exposures may be performed only on those target portions which are good.

Within a metrology system MET, a metrology apparatus is used to determine one or more properties of the substrate, and in particular, how one or more properties of different substrates vary or different layers of the same substrate vary from layer to layer. The metrology apparatus may be integrated into the lithographic apparatus LA or the lithocell LC or may be a stand-alone device. To enable rapid measurement, it is desirable that the metrology apparatus measure one or more properties in the exposed resist layer immediately after the exposure. However, the latent image in the resist has a low contrast—there is only a very small difference in refractive index between the parts of the resist which have been exposed to radiation and those which have not—and not all metrology apparatus have sufficient sensitivity to make useful measurements of the latent image. Therefore measurements may be taken after the post-exposure bake step (PEB) which is customarily the first step carried out on an exposed substrate and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of a faulty substrate but may still provide useful information.

To enable the metrology, one or more targets can be provided on the substrate. In an embodiment, the target is specially designed and may comprise a periodic structure. In an embodiment, the target is a part of a device pattern, e.g., a periodic structure of the device pattern. In an embodiment, the device pattern is a periodic structure of a memory device (e.g., a Bipolar Transistor (BPT), a Bit Line Contact (BLC), etc. structure).

In an embodiment, the target on a substrate may comprise one or more 1-D periodic structures (e.g., gratings), which are printed such that after development, the periodic structural features are formed of solid resist lines. In an embodiment, the target may comprise one or more 2-D periodic structures (e.g., gratings), which are printed such that after development, the one or more periodic structures are formed of solid resist pillars or vias in the resist. The bars, pillars or vias may alternatively be etched into the substrate (e.g., into one or more layers on the substrate).

In an embodiment, one of the parameters of interest of a patterning process is overlay. Overlay can be measured using dark field scatterometry in which the zeroth order of diffraction (corresponding to a specular reflection) is blocked, and only higher orders processed. Examples of dark field metrology can be found in PCT patent application publication nos. WO 2009/078708 and WO 2009/106279, which are hereby incorporated in their entirety by reference. Further developments of the technique have been described in U.S. patent application publications US2011-0027704, US2011-0043791 and US2012-0242970, which are hereby incorporated in their entirety by reference. Diffraction-based overlay using dark-field detection of the diffraction orders enables overlay measurements on smaller targets. These targets can be smaller than the illumination spot and may be surrounded by device product structures on a substrate. In an embodiment, multiple targets can be measured in one radiation capture.

A metrology apparatus suitable for use in embodiments to measure, e.g., overlay is schematically shown in FIG. 3A. A target T (comprising a periodic structure such as a grating) and diffracted rays are illustrated in more detail in FIG. 3B. The metrology apparatus may be a stand-alone device or incorporated in either the lithographic apparatus LA, e.g., at the measurement station, or the lithographic cell LC. An optical axis, which has several branches throughout the apparatus, is represented by a dotted line O. In this apparatus, radiation emitted by an output 11 (e.g., a source such as a laser or a xenon lamp or an opening connected to a source) is directed onto substrate W via a prism 15 by an optical system comprising lenses 12, 14 and objective lens 16. These lenses are arranged in a double sequence of a 4F arrangement. A different lens arrangement can be used, provided that it still provides a substrate image onto a detector.

In an embodiment, the lens arrangement allows for access of an intermediate pupil-plane for spatial-frequency filtering. Therefore, the angular range at which the radiation is incident on the substrate can be selected by defining a spatial intensity distribution in a plane that presents the spatial spectrum of the substrate plane, here referred to as a (conjugate) pupil plane. In particular, this can be done, for example, by inserting an aperture plate 13 of suitable form between lenses 12 and 14, in a plane which is a back-projected image of the objective lens pupil plane. In the example illustrated, aperture plate 13 has different forms, labeled 13N and 13S, allowing different illumination modes to be selected. The illumination system in the present examples forms an off-axis illumination mode. In the first illumination mode, aperture plate 13N provides off-axis illumination from a direction designated, for the sake of description only, as 'north'. In a second illumination mode, aperture plate 13S is used to provide similar illumination, but from an opposite direction, labeled 'south'. Other modes of illumination are possible by using different apertures. The rest of the pupil plane is desirably dark as any unnecessary radiation outside the desired illumination mode may interfere with the desired measurement signals.

As shown in FIG. 3B, target T is placed with substrate W substantially normal to the optical axis O of objective lens 16. A ray of illumination I impinging on target T from an angle off the axis O gives rise to a zeroth order ray (solid line 0) and two first order rays (dot-chain line +1 and double dot-chain line −1). With an overfilled small target T, these rays are just one of many parallel rays covering the area of the substrate including metrology target T and other features. Since the aperture in plate 13 has a finite width (necessary to admit a useful quantity of radiation), the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown. Note that the periodic structure pitch and illumination angle can be designed or adjusted so that the first order rays entering the objective lens are closely aligned with the central optical axis. The rays illustrated in FIGS. 3A and 3B are shown somewhat off axis, purely to enable them to be more easily distinguished in the diagram. At least the 0 and +1 orders diffracted by the target on substrate W are collected by objective lens 16 and directed back through prism 15.

Returning to FIG. 3A, both the first and second illumination modes are illustrated, by designating diametrically opposite apertures labeled as north (N) and south (S). When the incident ray I is from the north side of the optical axis, that is when the first illumination mode is applied using aperture plate 13N, the +1 diffracted rays, which are labeled +1(N), enter the objective lens 16, In contrast, when the second illumination mode is applied using aperture plate 13S the −1 diffracted rays (labeled −1(S)) are the ones which enter the lens 16. Thus, in an embodiment, measurement results are obtained by measuring the target twice under certain conditions, e.g., after rotating the target or changing the illumination mode or changing the imaging mode to obtain separately the −1st and the +1st diffraction order intensities. Comparing these intensities for a given target provides a measurement of asymmetry in the target, and asymmetry in the target can be used as an indicator of a parameter of a lithography process, e.g., overlay. In the situation described above, the illumination mode is changed.

A beam splitter 17 divides the diffracted beams into two measurement branches. In a first measurement branch, optical system 18 forms a diffraction spectrum (pupil plane image) of the target on first sensor 19 (e.g. a CCD or CMOS sensor) using the zeroth and first order diffractive beams. Each diffraction order hits a different point on the sensor, so that image processing can compare and contrast orders. The pupil plane image captured by sensor 19 can be used for focusing the metrology apparatus and/or normalizing intensity measurements. The pupil plane image can also be used for other measurement purposes such as reconstruction, as described further hereafter.

In the second measurement branch, optical system 20, 22 forms an image of the target on the substrate W on sensor 23 (e.g. a CCD or CMOS sensor). In the second measurement branch, an aperture stop 21 is provided in a plane that is conjugate to the pupil-plane of the objective lens 16. Aperture stop 21 functions to block the zeroth order diffracted beam so that the image of the target formed on sensor 23 is formed from the −1 or +1 first order beam. Data regarding the images measured by sensors 19 and 23 are output to processor and controller PU, the function of which will depend on the particular type of measurements being performed. Note that the term 'image' is used in a broad sense. An image of the periodic structure features (e.g., grating lines) as such will not be formed, if only one of the −1 and +1 orders is present.

The particular forms of aperture plate 13 and stop 21 shown in FIG. 3 are purely examples. In another embodiment, on-axis illumination of the targets is used and an aperture stop with an off-axis aperture is used to pass substantially only one first order of diffracted radiation to the sensor. In yet other embodiments, 2nd, 3rd and higher order beams (not shown in FIG. 3) can be used in measurements, instead of or in addition to the first order beams.

In order to make the illumination adaptable to these different types of measurement, the aperture plate 13 may comprise a number of aperture patterns formed around a disc, which rotates to bring a desired pattern into place. Note that aperture plate 13N or 13S are used to measure a periodic structure of a target oriented in one direction (X or Y depending on the set-up). For measurement of an orthogonal periodic structure, rotation of the target through 90° and 270° might be implemented. Different aperture plates are shown in FIGS. 3C and D. FIG. 3C illustrates two further types of off-axis illumination mode. In a first illumination mode of FIG. 3C, aperture plate 13E provides off-axis illumination from a direction designated, for the sake of description only, as 'east' relative to the 'north' previously described. In a second illumination mode of FIG. 3C, aperture plate 13W is used to provide similar illumination, but from an opposite direction, labeled 'west'. FIG. 3D illustrates two further types of off-axis illumination mode. In a first illumination mode of FIG. 3D, aperture plate 13NW provides off-axis illumination from the directions designated 'north' and 'west' as previously described. In a second illumination mode, aperture plate 13SE is used to provide similar illumination, but from an opposite direction, labeled 'south' and 'east' as previously described. The use of these, and numerous other variations and applications of the apparatus are described in, for example, the prior published patent application publications mentioned above.

FIG. 4 depicts an example composite metrology target T formed on a substrate. The composite target comprises four periodic structures (in this case, gratings) 32, 33, 34, 35 positioned closely together. In an embodiment, the periodic structure layout may be made smaller than the measurement spot (i.e., the periodic structure layout is overfilled). Thus, in an embodiment, the periodic structures are positioned closely together enough so that they all are within a measurement spot 31 formed by the illumination beam of the metrology apparatus. In that case, the four periodic structures thus are all simultaneously illuminated and simultaneously imaged on sensors 19 and 23. In an example dedicated to overlay measurement, periodic structures 32, 33, 34, 35 are themselves composite periodic structures (e.g., composite gratings) formed by overlying periodic structures, i.e., periodic structures are patterned in different layers of the device formed on substrate W and such that at least one periodic structure in one layer overlays at least one periodic structure in a different layer. Such a target may have outer dimensions within 20 μm×20 μm or within 16 μm×16 μm. Further, all the periodic structures are used to measure overlay between a particular pair of layers. To facilitate a target being able to measure more than a single pair of layers, periodic structures 32, 33, 34, 35 may have differently biased overlay offsets in order to facilitate measurement of overlay between different layers in which the different parts of the composite periodic structures are formed. Thus, all the periodic structures for the target on the substrate would be used to measure one pair of layers and all the periodic structures for another same target on the substrate would be used to measure another pair of layers, wherein the different bias facilitates distinguishing between the layer pairs.

Returning to FIG. 4, periodic structures 32, 33, 34, 35 may also differ in their orientation, as shown, so as to diffract incoming radiation in X and Y directions. In one example, periodic structures 32 and 34 are X-direction periodic structures with biases of +d, −d, respectively. Periodic structures 33 and 35 may be Y-direction periodic structures with offsets +d and −d respectively. While four periodic structures are illustrated, another embodiment may include a larger matrix to obtain desired accuracy. For example, a 3×3 array of nine composite periodic structures may have biases −4d, −3d, −2d, −d, 0, +d, +2d, +3d, +4d. Separate images of these periodic structures can be identified in an image captured by sensor 23.

FIG. 5 shows an example of an image that may be formed on and detected by the sensor 23, using the target of FIG. 4 in the apparatus of FIG. 3, using the aperture plates 13NW or 13SE from FIG. 3D. While the sensor 19 cannot resolve the different individual periodic structures 32 to 35, the sensor 23 can do so. The dark rectangle represents the field of the image on the sensor, within which the illuminated spot 31 on the substrate is imaged into a corresponding circular area 41. Within this, rectangular areas 42-45 represent the images of the periodic structures 32 to 35. The target can be positioned in among device product features, rather than or in addition to in a scribe lane. If the periodic structures are located in device product areas, device features may also be visible in the periphery of this image field. Processor and controller PU processes these images using pattern recognition to identify the separate images 42 to 45 of periodic structures 32 to 35. In this way, the images do not have to be aligned very precisely at a specific location within the sensor frame, which greatly improves throughput of the measuring apparatus as a whole.

Once the separate images of the periodic structures have been identified, the intensities of those individual images can be measured, e.g., by averaging or summing selected pixel intensity values within the identified areas. Intensities and/or other properties of the images can be compared with one another. These results can be combined to measure different parameters of the lithographic process. Overlay performance is an example of such a parameter.

In an embodiment, one of the parameters of interest of a patterning process is feature width (e.g., CD). FIG. 6 depicts a highly schematic example metrology apparatus (e.g., a scatterometer) that can enable feature width determination. It comprises a broadband (white light) radiation projector 2 which projects radiation onto a substrate W. The redirected radiation is passed to a spectrometer detector 4, which measures a spectrum 10 (intensity as a function of wavelength) of the specular reflected radiation, as shown, e.g., in the graph in the lower left. From this data, the structure or profile giving rise to the detected spectrum may be reconstructed by processor PU, e.g. by Rigorous Coupled Wave Analysis and non-linear regression or by comparison with a library of simulated spectra as shown at the bottom right of FIG. 6. In general, for the reconstruction the general form of the structure is known and some variables are assumed from knowledge of the process by which the structure was made, leaving only a few variables of the structure to be determined from the measured data. Such a metrology apparatus may be configured as a normal-incidence metrology apparatus or an oblique-incidence metrology apparatus. Moreover, in addition to measurement of a parameter by reconstruction, angle resolved scatterometry is useful in the measurement of asymmetry of features in product and/or resist patterns. A particular application of asymmetry measurement is for the measurement of overlay, where the target comprises one set of periodic features superimposed on another. The concepts of asymmetry measurement in this manner are described, for example, in U.S. patent application publication US2006-066855, which is incorporated herein in its entirety.

Figure 7:
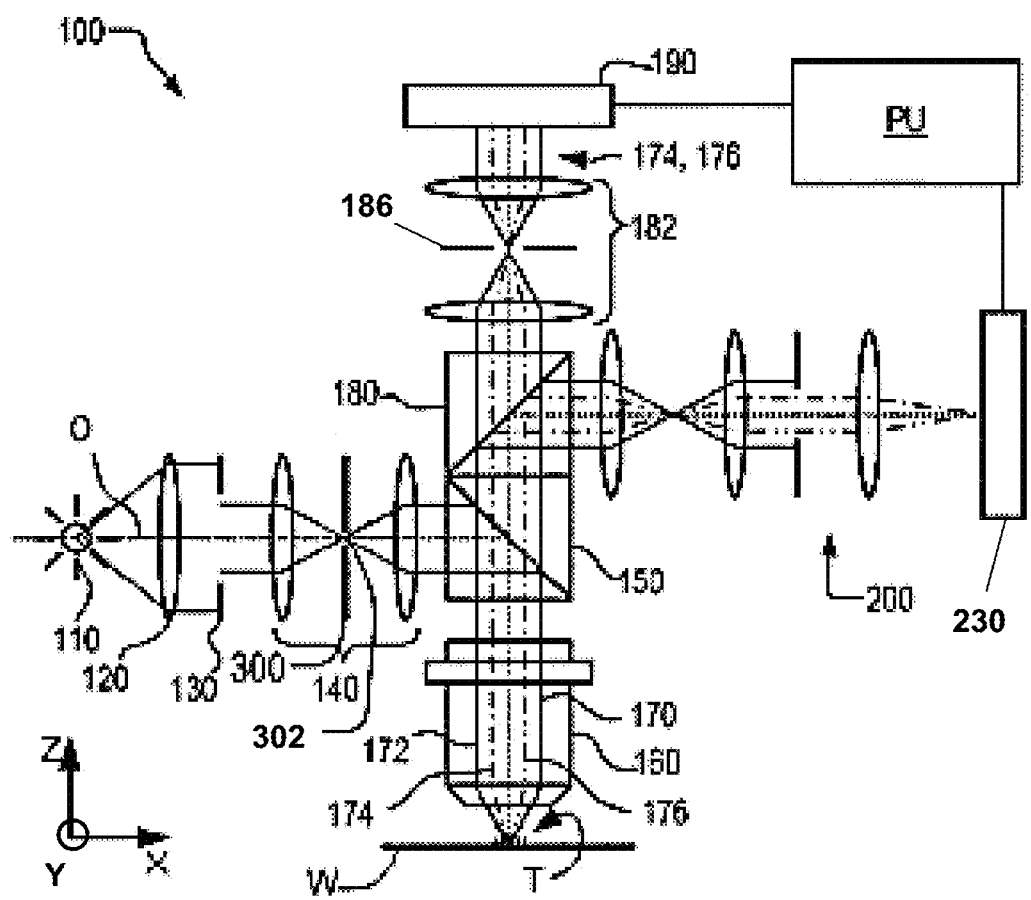
FIG. 7 schematically depicts an example metrology apparatus.

FIG. 7 illustrates an example of a metrology apparatus 100 suitable for use in embodiments of the invention disclosed herein. The principles of operation of this type of metrology apparatus are explained in more detail in the U.S. Patent Application Nos. US 2006-033921 and US 2010-201963, which are incorporated herein in their entireties by reference. An optical axis, which has several branches throughout the apparatus, is represented by a dotted line O. In this apparatus, radiation emitted by source 110 (e.g., a xenon lamp) is directed onto substrate W via by an optical system comprising: lens system 120, aperture plate 130, lens system 140, a partially reflecting surface 150 and objective lens 160. In an embodiment these lens systems 120, 140, 160 are arranged in a double sequence of a 4 F arrangement. In an embodiment, the radiation emitted by radiation source 110 is collimated using lens system 120. A different lens arrangement can be used, if desired. The angular range at which the radiation is incident on the substrate can be selected by defining a spatial intensity distribution in a plane that presents the spatial spectrum of the substrate plane. In particular, this can be done by inserting an aperture plate 130 of suitable form between lenses 120 and 140, in a plane which is a back-projected image of the objective lens pupil plane. Different intensity distributions (e.g., annular, dipole, etc.) are possible by using different apertures. The angular distribution of illumination in radial and peripheral directions, as well as properties such as wavelength, polarization and/or coherency of the radiation, can all be adjusted to obtain desired results. For example, one or more interference filters 130 (see FIG. 9) can be provided between source 110 and partially reflecting surface 150 to select a wavelength of interest in the range of, say, 400-900 nm or even lower, such as 200-300 nm. The interference filter may be tunable rather than comprising a set of different filters. A grating could be used instead of an interference filter. In an embodiment, one or more polarizers 170 (see FIG. 9) can be provided between source 110 and partially reflecting surface 150 to select a polarization of interest. The polarizer may be tunable rather than comprising a set of different polarizers.

As shown in FIG. 7, the target T is placed with substrate W normal to the optical axis O of objective lens 160. Thus, radiation from source 110 is reflected by partially reflecting surface 150 and focused into an illumination spot S (see FIG. 8) on target T on substrate W via objective lens 160. In an embodiment, objective lens 160 has a high numerical aperture (NA), desirably at least 0.9 or at least 0.95. An immersion metrology apparatus (using a relatively high refractive index fluid such as water) may even have a numerical aperture over 1.

Rays of illumination 170, 172 focused to the illumination spot from angles off the axis O gives rise to diffracted rays 174, 176. It should be remembered that these rays are just one of many parallel rays covering an area of the substrate including target T. Each element within the illumination spot is within the field of view of the metrology apparatus. Since the aperture in plate 130 has a finite width (necessary to admit a useful quantity of radiation), the incident rays 170, 172 will in fact occupy a range of angles, and the diffracted rays 174, 176 will be spread out somewhat. According to the point spread function of a small target, each diffraction order will be further spread over a range of angles, not a single ideal ray as shown.

At least the $0^{th}$ order diffracted by the target on substrate W is collected by objective lens 160 and directed back through partially reflecting surface 150. An optical element 180 provides at least part of the diffracted beams to optical system 182 which forms a diffraction spectrum (pupil plane image) of the target T on sensor 190 (e.g. a CCD or CMOS sensor) using the zeroth and/or first order diffractive beams. In an embodiment, an aperture 186 is provided to filter out certain diffraction orders so that a particular diffraction order is provided to the sensor 190. In an embodiment, the aperture 186 allows substantially or primarily only zeroth order radiation to reach the sensor 190. In an embodiment, the sensor 190 may be a two-dimensional detector so that a two-dimensional angular scatter spectrum of a substrate target T can be measured. The sensor 190 may be, for example, an array of CCD or CMOS sensors, and may use an integration time of, for example, 40 milliseconds per frame. The sensor 190 may be used to measure the intensity of redirected radiation at a single wavelength (or narrow wavelength range), the intensity separately at multiple wavelengths or integrated over a wavelength range. Furthermore, the sensor may be used to separately measure the intensity of radiation with transverse magnetic- and/or transverse electric-polarization and/or the phase difference between transverse magnetic- and transverse electric-polarized radiation.

Optionally, optical element 180 provides at least part of the diffracted beams to measurement branch 200 to form an image of the target on the substrate W on a sensor 230 (e.g. a CCD or CMOS sensor). The measurement branch 200 can be used for various auxiliary functions such as focusing the metrology apparatus (i.e., enabling the substrate W to be in focus with the objective 160), and/or for dark field imaging of the type mentioned in the introduction.

In order to provide a customized field of view for different sizes and shapes of grating, an adjustable field stop 300 is provided within the lens system 140 on the path from source 110 to the objective lens 160. The field stop 300 contains an aperture 302 and is located in a plane conjugate with the plane of the target T, so that the illumination spot becomes an image of the aperture 302. The image may be scaled according to a magnification factor, or the aperture and illumination spot may be in 1:1 size relation. In order to make the illumination adaptable to different types of measurement, the aperture plate 300 may comprise a number of aperture patterns formed around a disc, which rotates to bring a desired pattern into place. Alternatively or in addition, a set of plates 300 could be provided and swapped, to achieve the same effect. Additionally or alternatively, a programmable aperture device such as a deformable mirror array or transmissive spatial light modulator can be used also.

Typically, a target will be aligned with its periodic structure features running either parallel to the Y axis or parallel to the X axis. With regard to its diffractive behavior, a periodic structure with features extending in a direction parallel to the Y axis has periodicity in the X direction, while the a periodic structure with features extending in a direction parallel to the X axis has periodicity in the Y direction. In order to measure the performance in both directions, both types of features are generally provided. While for simplicity there will be reference to lines and spaces, the periodic structure need not be formed of lines and space. Moreover, each line and/or space between lines may be a structure formed of smaller sub-structures. Further, the periodic structure may be formed with periodicity in two dimensions at once, for example where the periodic structure comprises posts and/or via holes.

Figure 8:
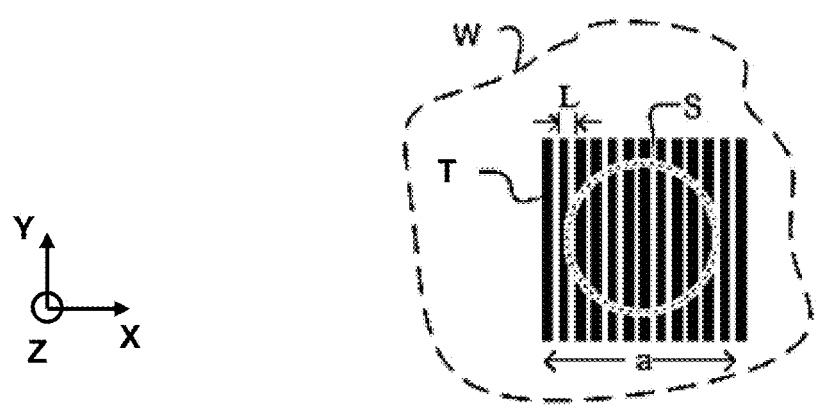
FIG. 8 illustrates the relationship between an illumination spot of a metrology apparatus and a metrology target.

FIG. 8 illustrates a plan view of a typical target T, and the extent of illumination spot S in the apparatus of FIG. 7. To obtain a diffraction spectrum that is free of interference from surrounding structures, the target T, in an embodiment, is a periodic structure (e.g., grating) larger than the width (e.g., diameter) of the illumination spot S. The width of spot S may be smaller than the width and length of the target. The target in other words is 'underfilled' by the illumination, and the diffraction signal is essentially free from any signals from product features and the like outside the target itself. This simplifies mathematical reconstruction of the target as it can be regarded as infinite.

Figure 9:
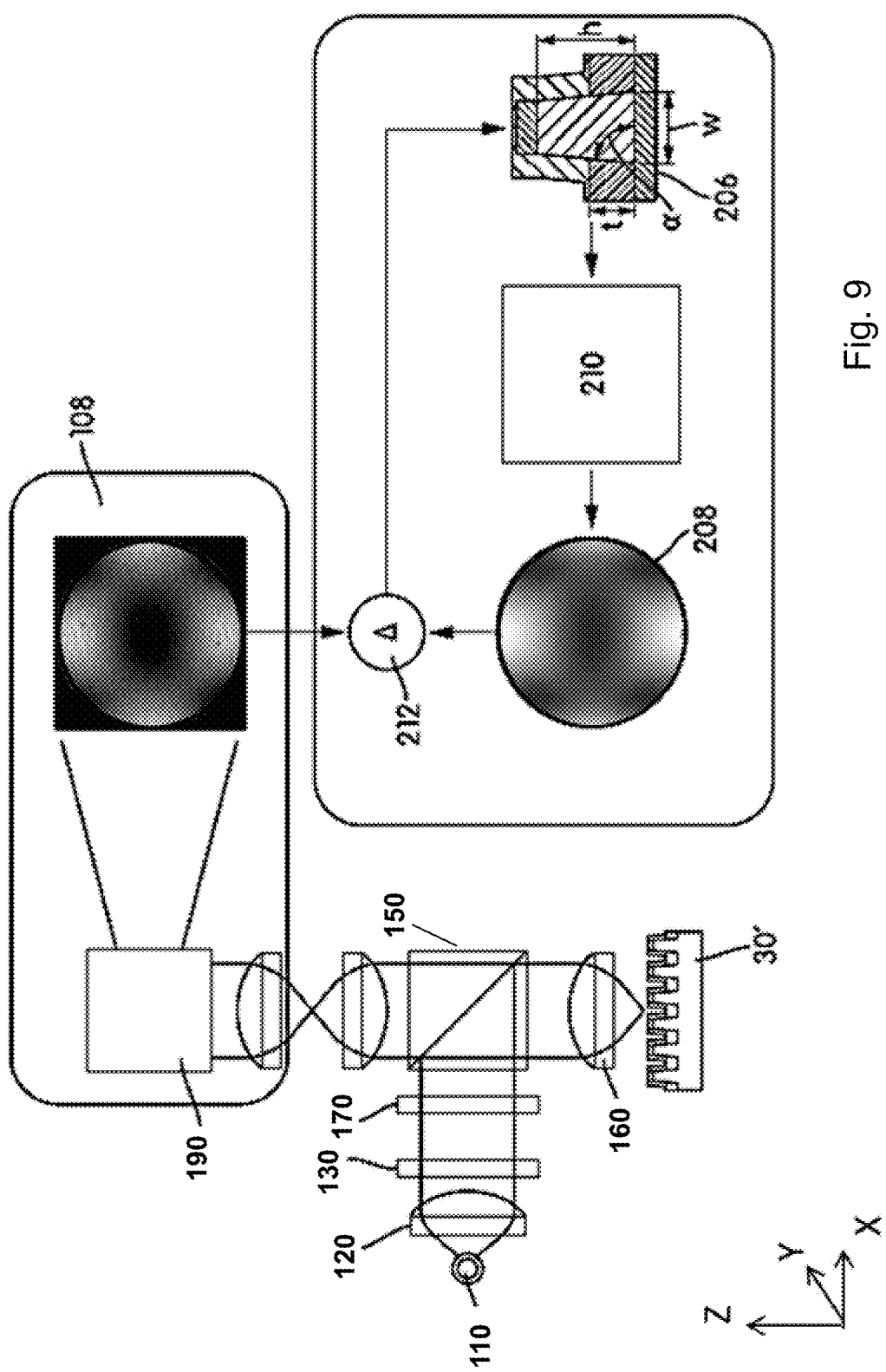
FIG. 9 schematically depicts a process of deriving one or more variables of interest based on measurement data.

FIG. 9 schematically depicts an example process of the determination of the value of one or more variables of interest of a target pattern 30' based on measurement data obtained using metrology. Radiation detected by the detector 190 provides a measured radiation distribution 108 for target 30'.

For the given target 30', a radiation distribution 208 can be computed/simulated from a parameterized mathematical model 206 using, for example, a numerical Maxwell solver 210. The parameterized mathematical model 206 shows example layers of various materials making up, and associated with, the target. The parameterized mathematical model 206 may include one or more of variables for the features and layers of the portion of the target under consideration, which may be varied and derived. As shown in FIG. 9, the one or more of the variables may include the thickness t of one or more layers, a width w (e.g., CD) of one or more features, a height h of one or more features, a sidewall angle α of one or more features, and/or relative position between features (herein considered overlay). Although not shown, the one or more of the variables may further include, but is not limited to, the refractive index (e.g., a real or complex refractive index, refractive index tensor, etc.) of one or more of the layers, the extinction coefficient of one or more layers, the absorption of one or more layers, resist loss during development, a footing of one or more features, and/or line edge roughness of one or more features. One or more values of one or more parameters of a 1-D periodic structure or a 2-D periodic structure, such as a value of width, length, shape or a 3-D profile characteristic, may be input to the reconstruction process from knowledge of the patterning process and/or other measurement processes. For example, the initial values of the variables may be those expected values of one or more parameters, such as a value of CD, pitch, etc., for the target being measured.

In some cases, a target can be divided into a plurality of instances of a unit cell. To help ease computation of the radiation distribution of a target in that case, the model 206 can be designed to compute/simulate using the unit cell of the structure of the target, where the unit cell is repeated as instances across the full target. Thus, the model 206 can compute using one unit cell and copy the results to fit a whole target using appropriate boundary conditions in order to determine the radiation distribution of the target.

Additionally or alternatively to computing the radiation distribution 208 at the time of reconstruction, a plurality of radiation distributions 208 can be pre-computed for a plurality of variations of variables of the target portion under consideration to create a library of radiation distributions for use at the time of reconstruction.

The measured radiation distribution 108 is then compared at 212 to the computed radiation distribution 208 (e.g., computed near that time or obtained from a library) to determine the difference between the two. If there is a difference, the values of one or more of the variables of the parameterized mathematical model 206 may be varied, a new computed radiation distribution 208 obtained (e.g., calculated or obtained from a library) and compared against the measured radiation distribution 108 until there is sufficient match between the measured radiation distribution 108 and the radiation distribution 208. At that point, the values of the variables of the parameterized mathematical model 206 provide a good or best match of the geometry of the actual target 30'. In an embodiment, there is sufficient match when a difference between the measured radiation distribution 108 and the computed radiation distribution 208 is within a tolerance threshold.

In these metrology apparatuses, a substrate support may be provided to hold the substrate W during measurement operations. The substrate support may be similar or identical in form to the substrate table WT of FIG. 1. In an example where the metrology apparatus is integrated with the lithographic apparatus, it may even be the same substrate table. Coarse and fine positioners may be provided to accurately position the substrate in relation to a measurement optical system. Various sensors and actuators are provided for example to acquire the position of a target of interest, and to bring it into position under the objective lens. Typically many measurements will be made on targets at different locations across the substrate W. The substrate support can be moved in X and Y directions to acquire different targets, and in the Z direction to obtain a desired location of the target relative to the focus of the optical system. It is convenient to think and describe operations as if the objective lens is being brought to different locations relative to the substrate, when, for example, in practice the optical system may remain substantially stationary (typically in the X and Y directions, but perhaps also in the Z direction) and only the substrate moves. Provided the relative position of the substrate and the optical system is correct, it does not matter in principle which one of those is moving in the real world, or if both are moving, or a combination of a part of the optical system is moving (e.g., in the Z and/or tilt direction) with the remainder of the optical system being stationary and the substrate is moving (e.g., in the X and Y directions, but also optionally in the Z and/or tilt direction).

In an embodiment, the measurement accuracy and/or sensitivity of a target may vary with respect to one or more attributes of the beam of radiation provided onto the target, for example, the wavelength of the radiation beam, the polarization of the radiation beam, the intensity distribution (i.e., angular or spatial intensity distribution) of the radiation beam, etc. Thus, a particular measurement strategy can be selected that desirably obtains, e.g., good measurement accuracy and/or sensitivity of the target.

In order to monitor the patterning process (e.g., a device manufacturing process) that includes at least one pattern transfer step (e.g., an optical lithography step), the patterned substrate is inspected and one or more parameters of the patterned substrate are measured/determined. The one or more parameters may include, for example, overlay between successive layers formed in or on the patterned substrate, critical dimension (CD) (e.g., critical linewidth) of, for example, features formed in or on the patterned substrate, focus or focus error of an optical lithography step, dose or dose error of an optical lithography step, optical aberrations of an optical lithography step, placement error (e.g., edge placement error), etc. This measurement may be performed on a target of the product substrate itself and/or on a dedicated metrology target provided on the substrate. The measurement can be performed after-development of a resist but before etching or can be performed after-etch.

In an embodiment, a parameter obtained from a measurement process is a parameter derived from a parameter determined directly from the measurement process. As an example, a derived parameter obtained from a measurement parameter is edge placement error for the patterning process. The edge placement error provides a variation in the location of an edge of a structure created by the patterning process. In an embodiment, the edge placement error is derived from an overlay value. In an embodiment, the edge placement error is derived from a combination of an overlay value and CD value. In an embodiment, the edge placement is derived from a combination of an overlay value, a CD value and a value corresponding to a local variation (e.g., edge roughness, shape asymmetry, etc. of the individual structures). In an embodiment, the edge placement error comprises an extreme value (e.g., 3 standard deviation, i.e., 3σ) of overlay and CD errors combined. In an embodiment, in a multi-patterning process involving creating structures and involving "cutting" structures by removing a portion of structure through etching of a pattern provided by the patterning process in relation to the structure, the edge placement error has the following form (or comprises one or more of the following terms):

$$\sqrt{(3\sigma_{overlay})^2 + \left(\frac{3\sigma_{CDU\ structure}}{2}\right)^2 + \left(\frac{3\sigma_{CDU\ cuts}}{2}\right)^2 +} \\ \frac{3\sigma_{OPE,PBA}}{2} + 6\sigma_{LER,LPE},$$

wherein σ is standard deviation, $\sigma_{overlay}$ corresponds to the standard deviation of overlay, corresponds to the standard deviation of overlay, $\sigma_{CDU\ structures}$ corresponds to the standard deviation of the critical dimension uniformity (CDU) of structures created in the patterning process, $\sigma_{CDU\ cuts}$ corresponds to the standard deviation of the critical dimension uniformity (CDU) of cuts, if any, created in the patterning process, $\sigma_{OPE,PBA}$ corresponds to the standard deviation of optical proximity effects (OPE) and/or proximity bias average (PBA) which is a difference between CD at pitch to a reference CD, and $\sigma_{LER,LPE}$ corresponds to the standard deviation of line edge roughness (LER) and/or local placement error (LPE). While formulation above is in relation standard deviation, it can be formulated in a different comparable statistical manner, such as variance.

There are various techniques for making measurements of the structures formed in the patterning process, including the use of a scanning electron microscope, an image-based measurement tool and/or various specialized tools. As discussed above, a fast and non-invasive form of specialized metrology tool is one in which a beam of radiation is directed onto a target on the surface of the substrate and properties of the scattered (diffracted/reflected) beam are measured. By evaluating one or more properties of the radiation scattered by the substrate, one or more properties of the substrate can be determined. This may be termed diffraction-based metrology. One such application of this diffraction-based metrology is in the measurement of feature asymmetry within a target. This can be used as a measure of overlay, for example, but other applications are also known. For example, asymmetry can be measured by comparing opposite parts of the diffraction spectrum (for example, comparing the −1st and +1$^{st}$ orders in the diffraction spectrum of a periodic grating). This can be done as described above and as described, for example, in U.S. patent application publication US2006-066855, which is incorporated herein in its entirety by reference. Another application of diffraction-based metrology is in the measurement of feature width (CD) within a target. Such techniques can use the apparatus and methods described above in respect of FIGS. 6-9.

Now, while these techniques are effective, it is desirable to provide a new measurement technique that derives feature asymmetry within a target (such as overlay, CD asymmetry, sidewall angle asymmetry, etc.). This technique can be effective for specially designed metrology targets or perhaps more significantly, for determining feature asymmetry directly on a device pattern.

Figures 10A, 10B:
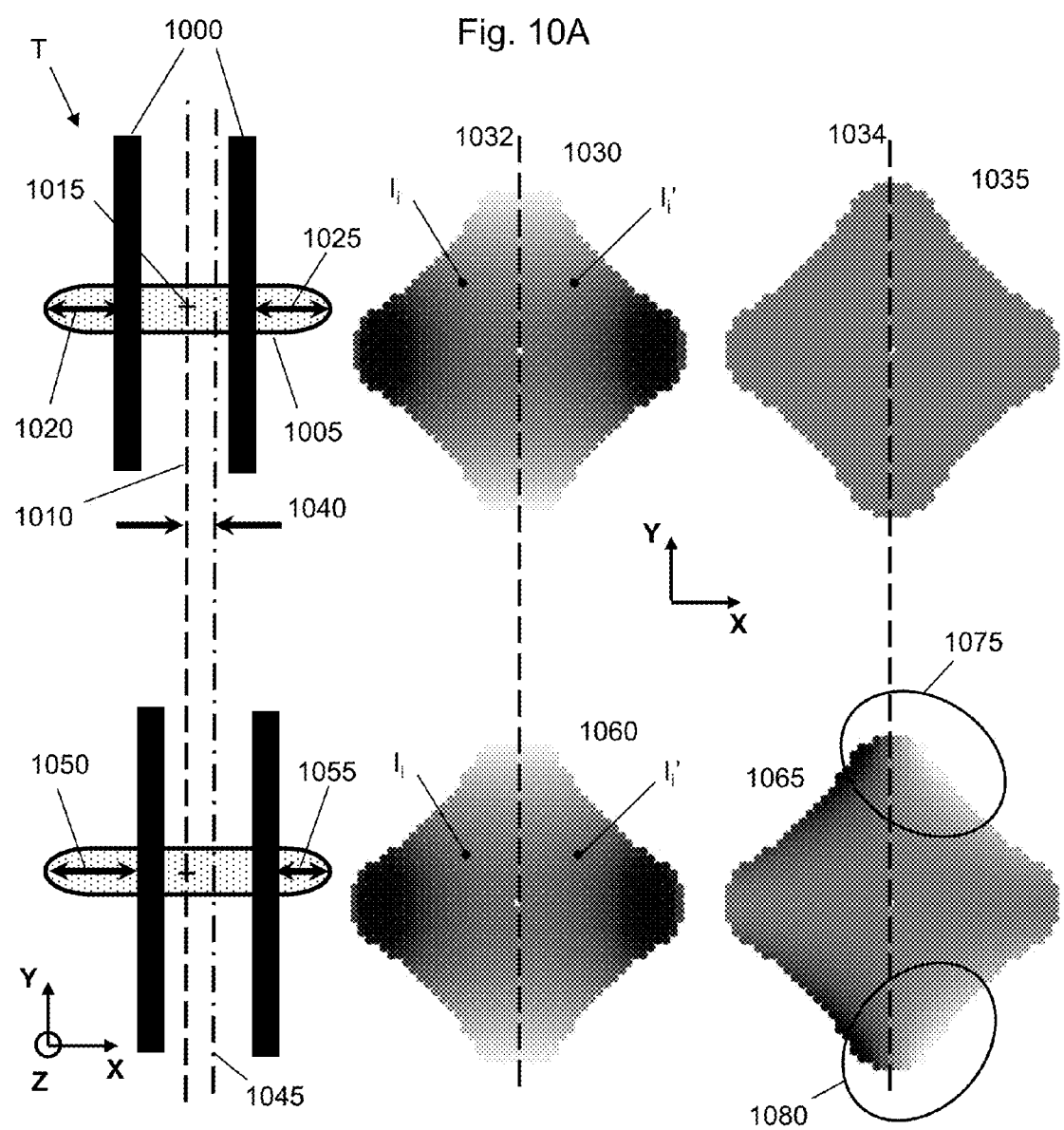
FIG. 10A schematically depicts an example unit cell, an associated pupil representation, and an associated derived pupil representation.
FIG. 10B schematically depicts an example unit cell, an associated pupil representation, and an associated derived pupil representation.
Figure 10C:
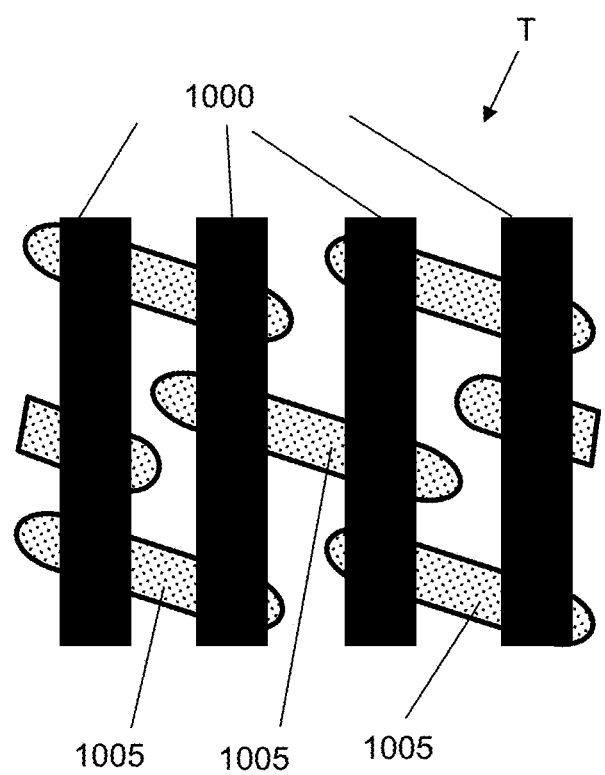
FIG. 10C schematically depicts an example target comprising one or more physical instances of a unit cell.

Referring to FIG. 10, principles of this measurement technique are described in the context of an overlay embodiment. In FIG. 10A, a geometrically symmetric unit cell of a target T is shown. The target T can comprise just a single physical instance of a unit cell or can comprise a plurality of physical instances of the unit cell as shown in FIG. 10C.

The target T can be a specially designed target. In an embodiment, the target is for a scribe lane. In an embodiment, the target can be an in-die target, i.e., the target is among the device pattern (and thus between the scribe lanes). In an embodiment, the target can have a feature width or pitch comparable to device pattern features. For example, the target feature width or pitches can be less than or equal to 300% of the smallest feature size or pitch of the device pattern, be less than or equal to 200% of the smallest feature size or pitch of the device pattern, be less than or equal to 150% of the smallest feature size or pitch of the device pattern, or be less than or equal to 100% of the smallest feature size or pitch of the device pattern.

The target T can be a device structure. For example, the target T can be a portion of a memory device (which often has one or more structures that are, or can be, geometrically symmetric as discussed further below).

In an embodiment, the target T or a physical instance of the unit cell can have an area of less than or equal to 2400 square microns, an area of less than or equal to 2000 square microns, an area of less than or equal to 1500 square microns, an area of less than or equal to 1000 square microns, an area of less than or equal to 400 square microns, less than or equal to 200 square microns, less than or equal to 100 square microns, less than or equal to 50 square microns, less than or equal to 25 square microns, less than or equal to 10 square microns, less than or equal to 5 square microns, less than or equal to 1 square micron, less than or equal to 0.5 square microns, or less than or equal to 0.1 square microns. In an embodiment, the target T or a physical instance of the unit cell has a cross-sectional dimension parallel to the plane of the substrate of less than or equal to 50 microns, less than or equal to 30 microns, less than or equal to 20 microns, less than or equal to 15 microns, less than or equal to 10 microns, less than or equal to 5 microns, less than or equal to 3 microns, less than or equal to 1 micron, less than or equal to 0.5 microns, less than or equal to 0.2 microns, or less than or equal to 0.1 microns.

In an embodiment, the target T or a physical instance of the unit cell has a pitch of structures of less than or equal to less than or equal to 5 microns, less than or equal to 2 microns, less than or equal to 1 micron, less than or equal to 500 nm, less than or equal to 400 nm, less than or equal to 300 nm, less than or equal to 200 nm, less than or equal to 150 nm, less than or equal to 100 nm, less than or equal to 75 nm, less than or equal to 50 nm, less than or equal to 32 nm, less than or equal to 22 nm, less than or equal to 16 nm, less than or equal to 10 nm, less than or equal to 7 nm or less than or equal to 5 nm.

In an embodiment, the target T has a plurality of physical instances of the unit cell. Thus, a target T could typically have the higher dimensions listed here, while the physical instances of the unit cell will have the lower dimensions listed here. In an embodiment, the target T comprises 50,000 or more physical instances of the unit cell, 25,000 or more physical instances of the unit cell, 15,000 or more physical instances of the unit cell, 10,000 or more physical instances of the unit cell, 5,000 or more physical instances of the unit cell, 1000 or more physical instances of the unit cell, 500 or more physical instances of the unit cell, 200 or more physical instances of the unit cell, 100 or more physical instances of the unit cell, 50 or more physical instances of the unit cell, or 10 or more physical instances of the unit cell.

Desirably, the physical instance of the unit cell or the plurality of physical instances of the unit cell collectively fills a beam spot of the metrology apparatus. In that case, the measured results comprise essentially only information from the physical instance of the unit cell (or its plurality of instances). In an embodiment, the beam spot has a cross-sectional width of 50 microns or less, 40 microns or less, 30 microns or less, 20 microns or less, 15 microns or less, 10 microns or less, 5 microns or less, or 2 microns or less.

The unit cell in FIG. 10A comprises at least two structures that are, or will be, physically instantiated on the substrate. A first structure 1000 comprises lines and a second structure 1005 comprises an oval-type shape. Of course, the first and second structures 1000, 1005 can be different structures than depicted.

Further, in this example, there can be a relative shift between the first and second structures 1000, 1005 from their expected position due to their separate transfer onto the substrate so as to have an error in overlay. In this example, the first structure 1000 is located in a higher layer on a substrate than the second structure 1005. Thus, in an embodiment, the second structure 1005 can be produced in a first lower layer in a first execution of a patterning process and the first structure 1000 can be produced in a second higher layer than the first lower layer in a second execution of the patterning process. Now, it is not necessary that the first and second structures 1000, 1005 be located in different layers. For example, in a double patterning process (including, for example, an etching process as part thereof), the first and second structures 1000, 1005 could be produced in a same layer to form essentially a single pattern but there could still be an "overlay" concern in terms of their relative placement within the same layer. In this single layer example, both the first and second structures 1000, 1005 could have, for example, the form of lines like shown in FIG. 10A for the first structure 1000 but the lines of the second structure 1005, already provided on the substrate by a first pattern transfer process, could be interleaved with the lines of the structure 1000 provided in a second pattern transfer process.

Significantly, the unit cell has, or is capable of having, a geometric symmetry with respect to an axis or point. For example, the unit cell in FIG. 10A has reflection symmetry with respect to, for example, axis 1010 and point/rotational symmetry with respect to, for example, point 1015. Similarly, it can be seen that a physical instance of the unit cell (and thus a combination of physical instances of the unit cell) in FIG. 10C has a geometric symmetry.

In an embodiment, the unit cell has a geometric symmetry for a certain feature (such as overlay). Embodiments herein focus on the unit cell having zero overlay when it is geometrically symmetric. However, instead, the unit cell can have zero overlay for a certain geometric asymmetry. Appropriate offsets and calculations would then be used to account for the unit cell having a zero overlay when it has a certain geometric asymmetry. Pertinently, the unit cell should be capable of change in symmetry (e.g., become asymmetry, or become further asymmetric, or become symmetric from an asymmetric situation) depending on the certain feature value.

In the example of FIG. 10A, the unit cell has a geometric symmetry for a zero overlay (although it need not be zero overlay). This is represented by the arrows 1020 and 1025 which shows that the lines of the first structure 1000 are evenly aligned with respect to the oval-type shape of the second structure 1005 (and which even alignment at least in part enables the unit cell to have geometric symmetry as shown in FIG. 10A). So, in this example, when the unit cell has geometric symmetry, there is zero overlay. However, when there is an error in overlay (e.g., a non-zero overlay), the unit cell is no longer geometrically symmetric and by definition the target is no longer geometrically symmetric.

Further, where a target comprises a plurality of physical instances of the unit, the instances of the unit cell are arranged periodically. In an embodiment, the instances of the unit cell are arranged in a lattice. In an embodiment, the periodic arrangement has a geometric symmetry within the target.

So, in this technique, as discussed further hereafter, advantage is taken of the change in geometric symmetry (e.g., a change to a geometric asymmetry, or change to a further geometric asymmetry, or a change from geometric asymmetry to geometric symmetry) related to a feature asymmetry of interest (e.g., non-zero overlay) to be able to determine the feature asymmetry (e.g., non-zero overlay).

A target comprising a physical instance of the unit cell of FIG. 10A can be illuminated with radiation using, for example, the metrology apparatus of FIG. 7. The radiation redirected by the target can be measured, e.g., by detector 190. In an embodiment, a pupil of the redirected radiation is measured, i.e., a Fourier transform plane. An example measurement of such a pupil is depicted as pupil image 1030. While the pupil image 1030 has a diamond-type shape, it need not have such a shape. The term pupil and pupil plane herein includes any conjugates thereof unless the context otherwise requires (for example, where a pupil plane of a particular optical system is being identified). The pupil image 1030 is effectively an image, specified in terms of an optical characteristic (in this case intensity), of a pupil of the redirected radiation.

For convenience, the discussion herein will focus on intensity as an optical characteristic of interest. But, the techniques herein may be used with one or more alternative or additional optical characteristics, such as phase and/or reflectivity.

Further, for convenience, the discussion herein focuses on detecting and processing images of redirected radiation and in particular pupil images. However, the optical properties of the redirected radiation can be measured and represented in different manners than images. For example, the redirected radiation can be processed in terms of one or more spectrums (e.g., intensity as a function of wavelength). Thus, a detected image of redirected radiation can be considered as an example of an optical representation of the redirected radiation. So, in the case of a pupil plane image, a pupil image is an example of a pupil representation.

Further, the redirected radiation can be polarized or non-polarized. In an embodiment, the measurement beam radiation is polarized radiation. In an embodiment, the measurement beam radiation is linearly polarized.

In an embodiment, a pupil representation is of primarily, or substantially, one diffraction order of redirected radiation from the target. For example, the radiation can be 80% or more, 85% or more, 90% or more, 95% or more, 98% or more or 99% or more, of a particular order of the radiation. In an embodiment, the pupil representation is of primarily, or substantially, zeroth order redirected radiation. This can occur, for example, when the pitch of the target, the wavelength of the measurement radiation, and optionally one or more other conditions cause the target to redirect primarily zeroth order (although there can be radiation of one or more higher orders). In an embodiment, a majority of the pupil representation is zeroth order redirected radiation. In an embodiment, the pupil representation is of zeroth radiation and separately of $1^{st}$ order radiation, which can then be linearly combined (superposition). The aperture 186 in FIG. 7 can be used to select a particular order, e.g., the zeroth order, of radiation.

Having regard to pupil image 1030 corresponding to the geometrically symmetric unit cell of the first and second structures 1000, 1005, it can be seen that the intensity distribution is essentially symmetric within the pupil image (e.g., with the same symmetry type as of the geometric structure). This is further confirmed by removing the symmetric intensity distribution portion from the pupil image 1030, which results in the derived pupil image 1035. To remove the symmetric intensity distribution portion, a particular pupil image pixel (e.g., a pixel) can have the symmetric intensity distribution portion removed by subtracting from the intensity at that particular pupil image pixel the intensity of a symmetrically located pupil image pixel, and vice versa. In an embodiment, the pixel can correspond to the pixels of the detector (e.g., detector 190), but it need not; for example, a pupil image pixel could be a plurality of the pixels of the detector. In an embodiment, the point or axis of symmetry across which pixel intensities are subtracted corresponds with a point or axis of symmetry of the unit cell. So, for example, considering pupil image 1030, the symmetry intensity distribution portion can be removed by, for example, subtracting from the intensity $I_i$ at that particular pixel shown the intensity $I_i'$ from a symmetrically located pixel, i.e., symmetrically located with respect to axis 1032. Thus, the intensity at a particular pixel with the symmetrical intensity portion removed, $S_i$, is then $S_i=I_i-I_i'$. This can be repeated for a plurality of pixels of the pupil image, e.g., all the pixels in the pupil image. As seen in the derived pupil image 1035, the intensity distribution corresponding to the symmetric unit cell is essentially completely symmetric. Thus, a symmetric target with a symmetric unit cell geometry (and if applicable, a certain periodicity of instances of the unit cell) results in a symmetric pupil response as measured by a metrology apparatus.

Referring now to FIG. 10B, an example of an error in overlay is depicted with respect to the unit cell depicted in FIG. 10A. In this case, the first structure 1000 is shifted in the X-direction with respect to the second structure 1005. In particular, the axis 1010 centered on the lines of the first structure 1000 has shifted to the right in FIG. 10B to axis 1045. Thus, there is an error in the overlay 1040 in the X-direction; that is, an X direction overlay error. Of course, the second structure 1005 could be shifted relative to the first structure 1000 or both could be shifted relative to each other. In any event, the result is an X direction overlay error. However, as should be appreciated from this unit cell arrangement, a purely relative shift in the Y-direction between the first structure 1000 and the second structure 1005 would not change the geometric symmetry of this unit cell. But, with an appropriate geometric arrangement, overlay in two directions or between different combinations of parts of the unit cell can change symmetry and could also be determined, as further discussed below.

As a consequence of the change in the physical configuration of the unit cell from the nominal physical configuration of the unit cell in FIG. 10A and represented by the error in overlay 1040, the result is that the unit cell has become geometrically asymmetric. This can be seen by the arrows 1050 and 1055 of different length, which show that the oval-type shape of the second structure 1005 is unevenly located relative to the lines of the first structure 1000. The symmetry is examined with respect to the point or axis of symmetry of the pupil image 1030, i.e. in that case, axis 1032 which is now shown axis 1034.

The physical instance of the unit cell of FIG. 10B can be illuminated with radiation using, for example, the metrology apparatus of FIG. 7. A pupil image of the redirected radiation can be recorded, e.g., by detector 190. An example of such a pupil image is depicted as pupil image 1060. The pupil image 1060 is effectively an image of the intensity. While the pupil image 1060 has a diamond-type shape, it need not have such a shape; it can be a circular shape or any other shape. Moreover, the pupil image 1060 is of a substantially same axis or coordinate location as pupil image 1030. That is, in this embodiment, an axis of symmetry 1010 in the unit cell of FIG. 10A and the same axis in the unit cell of FIG. 10B align with an axis of symmetry 1032 of the pupil images 1030, 1060.

Having regard to pupil image 1060 corresponding to the geometrically asymmetric unit cell of the first and second structures 1000, 1005, it visually seems like the intensity distribution is essentially symmetric within the pupil image. However, there is an asymmetric intensity distribution portion within the pupil image. This asymmetric intensity distribution portion is due to the asymmetry in the unit cell. Moreover, the asymmetric intensity distribution is significantly lower in magnitude than a symmetric intensity distribution portion in the pupil image.

So, in an embodiment, to more effectively isolate the asymmetric intensity distribution portion, the symmetric intensity distribution portion can be removed from the pupil image 1060, which results in the derived pupil image 1065. Like with obtaining derived pupil image 1035, a particular pupil image pixel (e.g., a pixel) can have the symmetric intensity distribution portion removed by subtracting from the intensity at that particular pupil image pixel the intensity of a symmetrically located pupil image pixel, and vice versa, as discussed above. So, for example, considering pupil image 1060, the symmetry intensity distribution portion can be removed by, for example, subtracting from the intensity $I_i$ at that particular pixel shown the intensity $I_i'$ from a symmetrically located pixel, i.e., symmetrically located with respect to axis 1032 to yield $S_i$. This can be repeated for a plurality of pixels of the pupil image, e.g., all the pixels in the pupil image. In FIGS. 10A and 10B, the full derived pupil images of $S_i$ are depicted for explanation purposes. As will be appreciated, half of a derived pupil image of FIG. 10A or 10B is the same as the other half thereof. So, in an embodiment, the values from only half of the pupil image can be used for further processing discussed herein and so a derived image pupil used in further processing herein can be only half of the $S_i$. values for a pupil.

As seen in the derived pupil image 1065, the intensity distribution measured using a physical instance of an asymmetric unit cell is not symmetric. As seen in regions 1075 and 1080, there is an asymmetric intensity distribution portion visible once the symmetric intensity distribution portion is removed. As noted above, the full derived pupil image 1065 is shown and so the asymmetric intensity distribution portion is shown on both halves (even though they are equal to each other in terms of magnitude and distribution in their respective halves).

Thus, an asymmetry in the geometrical domain corresponds to an asymmetry in the pupil. So, in an embodiment, a method is provided that uses the optical response of a periodic target that possesses, or is capable of, inherent geometric symmetry in its physical instance of a unit cell to determine a parameter corresponding to a physical configuration change that causes a change in geometric symmetry (e.g., cause an asymmetry, or cause a further asymmetry, or cause an asymmetric unit cell to become symmetric) of the physical instance of the unit cell. In particular, in an embodiment, an overlay induced asymmetry (or lack thereof) in the pupil as measured by a metrology apparatus can be exploited to determine the overlay. That is, the pupil asymmetry is used to measure the overlay within the physical instance of the unit cell and thus within the target.

To consider how to determine the parameter corresponding to a physical configuration change that causes a geometric asymmetry in a unit cell, the intensity of a pixel in the pupil image can be considered in terms of the physical characteristics of the target that impact that pixel. To do so, an overlay example will be considered but the techniques and principles can be extended to another parameter corresponding to a physical configuration change that causes a geometric asymmetry in a unit cell (e.g., asymmetric sidewall angle, asymmetric bottom wall tilt, ellipticity in contact holes, etc.).

Referring back to the unit cells of FIGS. 10A and 10B, the intensity of a pixel $I_i$, $I_i'$ in the pupil image 1060 can be evaluated analytically as a combination of intensity components attributable to different physical characteristics of the unit cell. In particular, the physical configuration changes from the symmetric unit cell to the asymmetric unit cell can be evaluated to determine in what manner the intensity distribution changes and specifically within a pupil image.

So, in a very simple example to illustrate the principles, several changes in physical configuration of the unit cell profile can be evaluated (but of course more or different physical configuration changes can occur). One of the physical configuration changes that will be considered is the change in height of the structure 1000 in the Z direction, which is designated as $\Delta x_h$. But, significantly, this change in height will generally be uniform across the physical instance of the unit cell. That is, the $\Delta x_h$ will result in a same changed physical configuration of the unit cell at one side of an axis or point of symmetry as at another side of the axis or point of symmetry. Similarly, other physical configuration changes, such as CD, sidewall angle, etc. changes, will also be generally uniform across the physical instance of the unit cell and thus yield a same changed physical configuration of the unit cell at one side of an axis or point of symmetry as at another side of the axis or point of symmetry. So, for convenience, only $\Delta x_h$ will be considered, but is representative of numerous other physical configuration changes that are uniform across the unit cell.

Another one of the physical configuration changes of the unit cell of interest is the relative shift between structure 1000 and structure 1005, namely the change in overlay 1040. This overlay shift will be referred to as $\Delta x_{ov}$. Of course, the overlay can be considered in a different or additional direction. Significantly, the $\Delta x_{ov}$ will result in a different physical configuration of the unit cell at one side of an axis or point of symmetry than at another side of the axis or point of symmetry; each pair of symmetric pixels has information about overlay. Significantly, while change in most target profile parameters (CD, height, etc.) induce symmetric changes in the pupil (and thus can be considered symmetric parameters), change in overlay results in an asymmetric change in the measured pupil. Thus, a change in overlay gives an asymmetric pupil response. Further, most, if not all, other unit cell profile parameters do not create asymmetry of the unit cell or the pupil response. However, they can have an effect on the measured overlay value. As discussed below, to the first order, other unit cell profile parameters may have no effect. In an embodiment, to a second or higher order, other unit cell profile parameters have an effect on determination of the overlay value. Hence, as discussed in more detail below, by measuring the pupil asymmetry, overlay can be determined therefrom.

Specifically, to evaluate how overlay can be determined from a measured pupil asymmetry, the intensity $I_i$ of a pixel i in the pupil image 1060 can be defined as:

$$I_i = I_0 + a\Delta x_{ov} + d\Delta x_h + b\Delta x_{ov}\Delta x_h + e\Delta x_{ov}^2 + f\Delta x_h^2 + \ldots c\Delta x_{ov}^3 + \quad (1)$$

where $I_0$ is a base intensity attributable to the illumination radiation and a, e, f and g are coefficients. So, similarly, the intensity of the complementary symmetric pixel $I'_i$ in the pupil image 1060 can be defined as:

$$I'_i = I_0 + a'\Delta x_{ov} + d'\Delta x_h + b'\Delta x_{ov}\Delta x_h + e'\Delta x_{ov}^2 + f'\Delta x_h^2 + \ldots c'\Delta x_{ov}^3 + \quad (2)$$

where coefficients a', b', c', d', e' and f' are specific to the intensity of the complementary symmetric pixel $I'_i$ and are comparable to the coefficients a, b, c, d, e and f for the intensity of a pixel $I_i$ in the pupil image 1060.

The difference of the intensity $S_i = I_i - I'_i$ between the symmetric pixels in the pupil image 1060 can then be evaluated as:

$$S_i = I_i - I'_i = (a-a')\Delta x_{ov} + (b-b')\Delta x_{ov}\Delta x_h + (c-c')\Delta x_{ov}^3 + \quad (3)$$

It has been discovered that due to, e.g., symmetry, all the terms that can contain only symmetric parameters, such as $e\Delta x_h$, drop out as seen in equation (3). Further, due to, e.g., symmetry, the terms with an even power of overlay have been discovered to be equal for symmetrically positioned pixels and so terms such $\Delta x_{ov}^2$ likewise drop out. That leaves, terms that have a combination of overlay with a symmetric parameter and terms that have only overlay to an odd power (e.g., to the power of 1, 3, 5, 7, etc.).

In equation (3) above, it has been discovered that the difference of the intensity $S_i$ is primarily dependent on $a\Delta x_{ov}$. That is, the difference of the intensity $S_i$ is in great part linearly dependent on overlay or more significantly, overlay is in great part linearly dependent on the intensity, specifically the difference of the intensity $S_i$. Thus, a combination of the intensities of the pixels can yield a good estimated value of the overlay when linearly combined with an appropriate conversion factor.

So, in an embodiment, it has been discovered that an overlay can be determined from a combination of intensities of the pixels that are appropriately weighted (wherein the weighting themselves acts a conversion factor of intensity to overlay or that can be combined with a conversion factor from intensity to overlay). In an embodiment, an overlay signal can be described as:

$$M = \Sigma_i w_i S_i \quad (4)$$

wherein the overlay signal M is the weighted combination of the signal components $S_i$ in the measured pupil and $w_i$ are the respective weights for each of the signal components $S_i$ (and the weights act as a conversion factor between the signal component and overlay; as noted above, instead, a conversion factor could be used in combination with weights that do not act to convert the signal component to overlay). In an embodiment, the weights $w_i$ are a vector whose magnitude is related to the overlay. As noted above, the signal components $S_i$ can be determined for half of the measured pupil. In an embodiment, if the signal components $S_i$ have a substantially same magnitude for all pairs (N/2) of symmetric pixels (N), then the signal components $S_i$ can be averaged and combined with a conversion factor C from the total of the signal components $S_i$ to overlay according to the following formula to yield a total overlay:

$$M = C\frac{2}{N}\sum_i^{N/2} S_i.$$

So, in an embodiment, the weights can have two roles—one is as a trust per pair of pixels in respect of its measurement of overlay and the other role is to convert a value of the optical characteristic of the signal component (e.g., intensity level, e.g., gray level) to an overlay value (in terms of, e.g., nanometers), As discussed above, the second role can be delegated to a conversion factor.

But, where, e.g., the signal components $S_i$ do not have a substantially same magnitude for all pairs of symmetric pixels, weighting all pixels in the measured pupil equally could result in a low signal-to-noise ratio (poor precision). So, it is desirable to weight those pixels that are sensitive to overlay to have a greater contribution to the calculation of the overlay. So, in an embodiment, pixels sensitive to overlay get different (e.g., higher) weights than those pixels that have low sensitivity to overlay (effectively inactive pixels). As noted above, the pixels in regions 1075 and 1080 of the derived pupil 1065 have relatively higher sensitivity to overlay while the remaining pixels in the derived pupil 1065, which have low to no intensity relative to the pixels in regions 1075 and 1080, have low sensitivity to overlay (and accordingly should be weighted to have lower contribution to the overlay determination).

In an embodiment, the weights are effectively determined for the $a\Delta_{ov}$ term of equation (3). In an embodiment, the weights can be extended to be determined for the $a\Delta x_{ov}$ term as well as the $v\Delta x_{ov}\Delta x_h$ (and typically other comparable terms for other parameters, such as CD, sidewall angle, etc.). However, this calculation can be more complex than determining the weights effectively only for the $a\Delta x_{ov}$ term of equation (3). Moreover, there is a tradeoff between robustness to non-linear processes (for symmetric parameters) and precision of determining overlay (i.e., in terms of how close the determined values are for each determination of the same actual overlay). So, there can be a sacrifice of precision for enhanced robustness using this calculation. Accordingly, an optimization can be performed to enhance precision (e.g., maximizing the influence of the linear terms and suppressing the non-linear terms), enhance robustness (e.g., maximizing the non-linear terms) or find a balance of both. But, in any event, the use of a combination of intensities linearly combined with associated weightings can lead to a quick determination of overlay as it requires merely a pupil acquisition and simple calculation of equation (4).

In an embodiment, where higher order terms become significant, a non-linear solution technique can be adopted to solve equation (3) having the $c\Delta x_{ov}^3$ and/or other higher order terms. As will be appreciated, a non-linear solution technique can be more complex than simply multiplying each signal components $S_i$ in the measured pupil with a respective weight $w_i$ for each signal components $S_i$ and then adding all of them up. Moreover, there is again tradeoff between robustness to non-linear processes and precision of determining overlay (i.e., in terms of how close the determined values are for each determination of the same actual overlay). So, there can be a sacrifice of precision for enhanced robustness using this calculation. Accordingly, an optimization can be performed to enhance precision and/or enhance robustness.

So, with the realization of an asymmetric intensity distribution arising from a geometric asymmetry of a unit cell caused by overlay, the error in overlay can be determined through an analysis that has a focus on this asymmetric intensity distribution. Thus, a technique for determining overlay from the asymmetric intensity distribution arising due to the change in physical configuration of a target associated with overlay will now be discussed.

Figure 11:
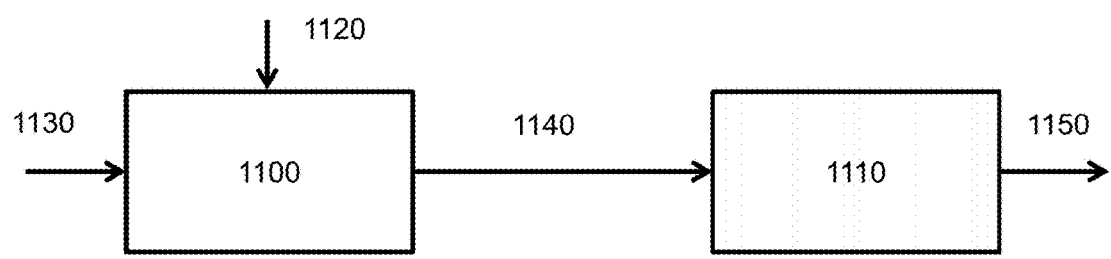
FIG. 11 depicts a high-level flow of obtaining weightings for determining a patterning process parameter from measured radiation.

Referring to FIG. 11, a method of determining the weights is schematically depicted. To enable the weight determination, the reconstruction techniques described above with respect to FIG. 9 will be used to advantage. That is, in an embodiment, CD reconstruction is used to isolate an overlay signal from a pupil image of an physical instance of an asymmetric unit cell.

The method of FIG. 11 involves two processes. A first process 1100 involves using reconstruction techniques for CD and/or one or more other profile parameters of a target to derive a nominal profile of the target (and thus of the one or more physical instances of the unit cell therein) as exposed on a substrate as part of a patterning process. With the nominal profile of the target, the basic engine of the reconstruction technique is used in process 1110 to derive the weightings. The weightings can then be used to derive overlay from a measured pupil as described further in relation to FIG. 12.

So, at process 1100, measurements 1130 of a substrate having one or more physical instances of a unit cell of interest provided thereon as a target, are obtained. In an embodiment, the measurements are of the target after etch. In an embodiment, the measurements are of the target after development but before etch. In an embodiment, the target is a device structure. In an embodiment, the measurements can be made, or have been made, using a metrology apparatus such as the metrology apparatus of FIG. 7. For example, the target can comprise a physical instance of the unit cell of FIG. 10A or FIG. 10B, e.g. a single instance or a plurality of adjacent instance as shown in FIG. 10C. In an embodiment, measurements of a plurality of targets (and thus of a plurality of physical instances of the unit cell) are obtained. In an embodiment, the measurements are of targets that are distributed across the substrate. In an embodiment, a plurality of substrates, each with one or more targets (each having one or more physical instances of the unit cell), is measured. So, in an embodiment, a radiation distribution 108 is obtained for each measured target.

Then, a reconstruction process at 1100, such as the reconstruction process described in and with respect to FIG. 9, is used to derive a nominal profile of the physical instance of the unit cell, comparable to the profile 206 of FIG. 9. The reconstruction process obtains an expected profile 1120 of the physical instance of the unit cell to start and facilitate the reconstruction process. In an embodiment, the derived nominal profile is obtained from an average of the profile of targets across one or more substrates. For example, the radiation distribution 108 for each target can be processed to derive a particular profile of that instance of the target and then the profiles for the plurality of instances of the target can be averaged together to derive the nominal profile. In an embodiment, the nominal profile comprises at least a geometric profile of the target. In an embodiment, the geometric profile is a 3-D profile. In an embodiment, the nominal profile comprises information regarding one or more materials properties of one or more layers making up the physical target.

So, in an embodiment, the nominal profile can be considered as a center of gravity for the values of various parameters of the profile of the target (and thus the unit cell) obtained from measuring numerous instances of the target across the substrate and optionally on more than one substrate. But, in an embodiment, the nominal profile can have different forms and be more specific. For example, the nominal profile can be defined for one or more particular instances of a target (e.g., by using values from the same target location(s) from multiple substrates). As another example, the nominal profile can be defined for a particular substrate (e.g., by using values from only that substrate). In an embodiment, the nominal profile can be tuned for a particular target and/or substrate as part of the process of FIG. 12. For example, when the target and/or substrate is measured as part of the process of FIG. 12, a reconstruction technique can be used with the measured data to fine tune the nominal profile for that target and/or substrate, the fine-tuned nominal profile can then be used as the nominal profile herein to determine weights and which weighs can then be used with the same measured data to yield one or more overlay values.

The reconstructed nominal profile 1140 is then provided to process 1110. Thus, in an embodiment, process 1110 uses a derived nominal profile of the target, e.g., a geometric after-etch profile of the unit cell of a device derived from measured data. In an embodiment, the nominal profile can be in the form of a parameterized model, like model 206 parameterized in accordance with the measured unit cell. Thus, in an embodiment, process 1110 uses a derived profile model of the unit cell, e.g., a model of the geometric after-etch profile of the physical instance of a unit cell of a device derived from measured data.

The basic engine of the reconstruction technique described herein is used in process 1110, along with the derived profile or the derived profile model, to derive the weightings. In an embodiment, the derived profile model or a derived profile model derived from the derived profile is used to determine pupil pixels sensitive to overlay in the unit cell. In particular, in an embodiment, the sensitivity to overlay of pupil response is determined by, using simulations (e.g., the Maxwell solver), to determine a change in pupil response to an induced change in overlay for the nominal profile.

This can be accomplished by causing the derived profile model to be changed such that an overlay change of a certain amount is induced (e.g., 1 nm) in the model, leaving all other parameters/variables of the derived profile model unchanged. This effectively causes a symmetric unit cell to become asymmetric or causes an already asymmetric unit cell ell can be symmetric) to change symmetry (including to become further asymmetric or to become symmetric from an asymmetric situation).

A pupil as would be expected in the metrology apparatus (e.g., for radiation at a certain measurement beam wavelength, measurement beam polarization, measurement beam intensity, etc.) can then be derived (e.g., using a Maxwell solver, a library search or other reconstruction technique) based on the derived profile model with the induced overlay change. Where the physical instance of the unit cell is smaller than a beam spot, the reconstruction can treat the beam spot as being filled with physical instances of the unit cell. In an embodiment, the derived pupil can be a simulated pupil image 1060 and/or a derived pupil image 1065 based on the simulated pupil image.

The derived pupil can be then used to determine the sensitivities of the intensity in a plurality of the pupil pixels to overlay change, for example by comparison with a derived pupil for the unit cell without the induced overlay (for example, the derived pupil for the unit cell without the induced overlay can be a simulated pupil image 1030 and/or a derived pupil image 1035 based on the simulated pupil image). In an embodiment, these sensitivities form the basis of the weightings.

In an embodiment, the pixels of the pupil (and thus the pixel intensities, signal components $S_i$, etc.) can be expressed as a vector. In an embodiment, the weightings can then be derived from a Jacobian matrix generated in the modelling. In an embodiment, the weightings can be derived from a Moore-Penrose pseudo inverse of the Jacobian matrix generated in the modelling. So, the weights are effectively determined for the $a\Delta x_{ov}$ term of equation (3). The weightings derived from the Jacobian matrix or the Moore-Penrose pseudo inverse of the Jacobian matrix appear to apply well for the relatively modest overlay variations (e.g., within ±3 nm or within ±4 nm or within ±5 nm).

In an embodiment, the weights can be extended to be determined for the $a\Delta x_{ov}$ term as well as the $b\Delta x_{ov}\Delta x_h$ (and typically other comparable terms for other parameters, such as CD, sidewall angle, etc.). In this case, the weightings are, or can be derived from, a Hessian matrix generated in the modelling in addition to the Jacobian matrix. The Hessian shows how the response to the overlay changes due to a change of a certain amount of another (symmetric) parameter (such as CD). So, for every such parameter there is a column in the Hessian. In an embodiment, to be (more) robust, the weights could be altered such that they become more orthogonal to the column (parameter) for which the unit cell is sensitive. To become more orthogonal, the one or more sensitive columns can be concatenated to the Jacobian, and then the Moore-Penrose pseudo inverse can be computed from this Jacobian with one or more columns from the Hessian concatenated thereto. From this computation, the weights follow. However, this calculation can be more complex and thus may be suitable for those situations where overlay values in practice are expected to exceed the overlay variation range for which the weightings derived from the (Moore-Penrose pseudo inverse of) Jacobian matrix show good results.

In an embodiment, the weights can be extended to be determined for other terms of equation (3). In that case, the weightings are, or can be derived from, third order derivatives generated in the modelling in addition to the Jacobian matrix.

As noted above, the nominal profile could be a fine-tuned nominal profile per target or substrate. For example, when the particular target or substrate is measured as part of the process of FIG. 12, a reconstruction technique can be used with the measured data to fine tune the nominal profile for that target or substrate. Now, depending on the fine-tuning, the weights can be (re-)determined and/or a choice made between the type of weighting being made (e.g., Jacobian or a combination of the Jacobian and Hessian). For example, weights, based on a nominal profile that wasn't fine-tuned, may have been previously selected to suppress the effect of $\Delta x_h$ but if the fine-tuning identifies and updates the $\Delta x_h$ for the target and/or substrate, the effect of $\Delta x_h$ may not need to be suppressed. Thus, weights could be chosen that more favor precision over robustness.

So, from process 1110, a collection (e.g., a vector) of weights $w_i$ can be output. The weights $w_i$ themselves can act as a conversion factor of intensity to overlay or they can be combined with a conversion factor from intensity to overlay (which conversion factor can be derived as part of the same modelling). As will be appreciated from pupil image 1065, the pixels in the regions 1075 and 1080 have relatively higher sensitivity to overlay than pixels outside of regions 1075 and 1080 and thus their weightings will be noticeably different (e.g., higher) than the weighting of pixels outside of region 1075 and 1080 (which pixels have relatively low sensitivity to overlay). So, when the weights are combined (such as according to equation (4)) with measured intensity values of a target having one or more physical instances of the unit cell, an overlay signal can be obtained for the particular target (such as a device pattern having a physical instance of the unit cell).

Further, one or more measurement parameters can be determined to form a measurement strategy for use in obtaining the measured intensity values of the target. One or more measurement parameters can affect the overlay sensitivity of pixels. For example, overlay sensitivity varies across different measurement beam wavelengths. So, in an embodiment, one or more measurement parameters (such as wavelength, polarization, dose, a number of optical characteristic readings taken by a detector sensor of a particular one illumination of the target (the readings typically averaged to provide an averaged optical characteristic value for the measurement of the target)) can be varied as part of the modelling process 1110. For example, one or more measurement parameters can be examined for a particular induced overlay change to determine a value of the one or more measurement parameters that reduces an error residual, for example between an overlay obtained when the weightings are for one value of the one or more parameters in relation to overlay obtained when the weightings are for another value of the one or more parameters, to a minimum or below a certain threshold. So, a value of one or more measurement parameters can then be obtained that improve precision.

Further, robustness to process variations differs across different values of one or more measurement parameters. For example, in particular, robustness to process variations differs across different values of measurement beam wavelength and/or measurement polarization. Thus, in an embodiment, the weighting scheme should address at least a dominant contributor to lack of robustness to process variation. So, additionally or alternatively to determining a value of one or more measurement parameters for improved precision, one or more measurement parameters can be examined for different particular induced overlay change values (and/or for particular induced changes of one or more other parameters of the derived profile model, such as a change in CD, side wall angle, etc.) to obtain a value of one or more measurement parameters that enables results using the weightings that have enhanced robustness to process variation. For example, for different amounts of induced overlay change, various values of the one or more measurement parameters can be evaluated to determine a value of the one or more measurement parameters that causes a minimum (or below a threshold) variation in the determined overlay using the weightings associated with the value of the one or more measurement parameters. Of course, a balance can be used in selection of the value of the one or more measurement parameters between precision and enhanced robustness. For example, a weighting can be applied between a value of the one or more measurement parameters determined for precision (e.g., a weight applied to a performance metric that measures precision) and a value of the one or more measurement parameters determined for enhanced robustness (e.g., a weight applied to a performance metric that measures robustness) and then a largest, top ranked, etc. combination can be selected. And of course, a plurality of values of one or more measurement parameters can be determined such that there is in effect a plurality of different measurement strategies in the overall measurement strategy. The plurality of values could be ranked according to one or more performance metrics. Thus, optionally, a measurement strategy can be output from process 1110 for use in obtaining measured intensity values of a target having one or more physical instances of the unit cell.

Further, one or more non-overlay parameters, such as CD, sidewall angle, etc., can affect the weights used for mapping the intensity signal to overlay. As noted above, an example manner of determining the weights in this context is to use a Hessian matrix and/or third order derivatives. So, in an embodiment, various possible weighting schemes are possible to take account of one or more non-overlay parameters so as to still maintain a good overlay value. In an embodiment, the overlay informative overlay pixels and their weightings can be optimized for overlay determination precision. This may require good model quality, i.e., good estimates of the non-overlay parameters. In an embodiment, the overlay informative pixels and their weights can be optimized for increased robustness to process variations such as in the non-overlay parameters. This may be at the expense of precision.

In an embodiment, estimates of the one or more non-overlay parameters can be made using, for example, the reconstruction techniques described in relation to FIG. 9, and fed-forward to tune the derived profile or derived profile model. For example, a CD reconstruction can estimate a CD of a target at a particular location at a substrate and/or for a particular combination of patterning process settings (e.g., exposure dose, exposure focus, etc.) and use that CD estimate to tune the CD parameter of the derived profile or derived profile model. In an embodiment, iterative reconstructions of the exact derived profile or derived profile model parameters can be performed.

Figure 12:
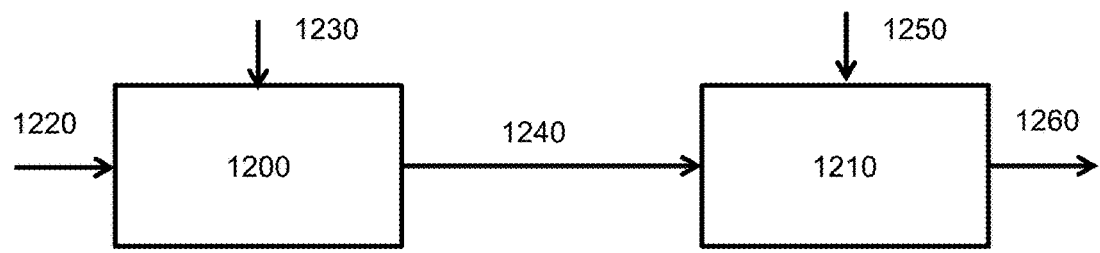
FIG. 12 depicts a high-level flow of determining a patterning process parameter from measured radiation.

Referring to FIG. 12, a method of determining an overlay value for a target having one or more physical instances of a unit cell capable of being geometrically symmetric. This method involves two processes 1200 and 1210. Process 1200 involves obtaining a measurement of the target having the one or more physical instances of the unit cell. Process 1210 involves determining an overlay value for the measured target based on the measurement of the target from process 1200.

Process 1200 takes an input the target 1220 to be measured including one or more physical instances of a unit cell as described herein capable of being geometrically symmetry. In an embodiment, a substrate with one or more instances of the target is provided to a metrology apparatus, such as the metrology apparatus of FIG. 7.

Optionally, process 1200 takes as input a particular measurement strategy 1230 specified for the target. In an embodiment, the measurement strategy can specify a value of one or more measurement parameters, such as one or more selected from: measurement beam wavelength, measurement beam polarization, measurement beam dose, and/or a number of optical characteristic readings taken by a detector sensor of the metrology apparatus of a particular one illumination of the target. In an embodiment, the measurement strategy can comprises a plurality of measurement strategies, each specifying a value of one or more measurement parameters. The measurement strategy can be used to measure the target.

Process 1200 then measures the target using a metrology apparatus according to the optional measurement strategy. In an embodiment, the metrology apparatus obtains a pupil representation of the redirected radiation. In an embodiment, the metrology apparatus can produce a pupil representation such as pupil image 1030 (if, for example, the target has no error in overlay) or pupil image 1060 (if, for example, the target has an error in overlay). Thus, in an embodiment, the process 1200 outputs optical information 1240 regarding the redirected radiation from the target, such as a pupil representation of the radiation.

Process 1210 then receives the optical information 1240 and processes the optical information to determine an overlay value 1260 for the target. In an embodiment, the process 1210 receives as input the weightings 1250 determined from the method of FIG. 11, which then are combined with one or more optical characteristic values (e.g., intensities) obtained or derived from the optical information 1240.

In an embodiment, the process 1210 (or process 1200) can process the optical information to derive a raw overlay signal from the optical information. In an embodiment, the raw overlay signal comprises a differential of the optical information, i.e., a difference in optical characteristic values between symmetric pixels across an axis or point of symmetry. In an embodiment, the derived pupil image 1035 (if, for example, the target has no error in overlay) or derived pupil image 1065 (if, for example, the target has an error in overlay) can be obtained.

In an embodiment, the weightings and optical information with respect to radiation redirected by the target (e.g., the optical information from process 1200 or a processed version of the optical information from process 1200 such as the raw overlay signal) are combined to determine the overlay value. In an embodiment, the use of a combination of redirected measurement beam intensities linearly combined with associated weightings can lead to a quick determination of overlay. For example, in an embodiment, the overlay value can be derived using equation (4) wherein the overlay value M is calculated as the weighted combination of signal components $S_i$ from the raw overlay signal using respective weights $w_i$ for each of the signal components $S_i$.

In an embodiment, the optical information collected from process 1200 can be used additionally to derive one or more target related parameters other than overlay. For example, the optical information collected from process 1200 can be used in a reconstruction process to derive any one or more geometric profile parameters of the target, such as CD, sidewall angle, bottom floor tilt, etc. So, in an embodiment, a same set of optical information collected from a target, such as an in-die after-etch target, can be used to determine overlay, CD and/or one or more other geometric profile parameters of the target (such as a device structure).

While, as noted above, focus has been on intensity, in an embodiment, the optical characteristic can be reflectivity, the radiation can be polarized and the measurements can be cross-polarization measurements. For example, a target exposed to a certain linear polarization can be measured with that polarization or at a different polarization. So, for symmetric pixels $p_i$ and $p'_i$ (where the apostrophe denotes the symmetric location), then reflectivity R for those pixels can be measured as follows:

$$\overline{R}_i = \begin{bmatrix} R_{ss} & R_{sp} \\ R_{ps} & R_{pp} \end{bmatrix} \quad (4)$$

$$\overline{R}'_i = \begin{bmatrix} R'_{ss} & R'_{sp} \\ R'_{ps} & R'_{pp} \end{bmatrix} \quad (5)$$

wherein s denotes s polarization and p denotes p polarization. Thus, the reflectivity $R_{ss}$ corresponds to reflectivity R of s polarized radiation measured when the target was illuminated using s polarization, reflectivity $R_{sp}$ corresponds to reflectivity R of s polarized radiation measured when the target was illuminated using p polarization, and so on. Moreover, these measurements can be taken at different wavelengths. And, it has been discovered that, in certain embodiments, the overlay for a symmetric unit cell that changes its symmetry in response to overlay change can be found and determined from the congruents $R_{ps}$ and $R_{sp}$.

Further, non-linearity can arise from overlay and/or from other parameters. As discussed above, certain non-linearity can be addressed through appropriate selection of weightings, e.g., by deriving the weightings using a Hessian matrix and/or third order derivatives. In an embodiment, the non-linearity can be addressed by using a non-linear solution to derive the overlay from the measured optical information of redirected radiation from a target.

In an embodiment, the overlay can be determined through using the reconstruction engine as described above used to derive the nominal profile. For example, a non-linear solver working from a model based on the derived nominal profile and/or a derived nominal profile model can be used to derive a simulated version of the optical information expected from redirected radiation from a target of interest, which can be compared to the measured optical information of the target of interest. As noted above, the target of interest comprises one or more physical instances of a unit cell that can be symmetric and that changes its symmetry when subject to overlay. Then, if there is not agreement within a certain threshold, a geometric profile parameter (e.g., overlay) can be varied and the simulated version of the optical information re-computed and compared to the measured optical information until there is agreement within a threshold. Similarly, measured optical information of a target of interest can be compared against a library of the optical information expected from redirected radiation from the target of interest (which library would typically be derived using a non-linear solver). Then, if there is not agreement within a certain threshold, a geometric profile parameter (e.g., overlay) can be varied and the library can be consulted again for a simulated version of the optical information which is compared to the measured optical information until there is agreement within a threshold.

In an embodiment, the use of the reconstruction engine with the measured optical information from a target of interest uses measured optical information from which a symmetric distribution of radiation has been removed as described above, e.g., by subtracting from the optical characteristic value at each pixel the optical characteristic value at a pixel symmetrically located across a point or axis of symmetry. Thus, the optical information relates to substantially only the asymmetric distribution of radiation. Similarly, the simulated or library version of the optical information relates to substantially only the asymmetric distribution of radiation. This will facilitate the speed of calculation and/or comparison as a significant portion of optical information won't need to be calculated or evaluated since it will eliminate through the differencing.

In a further embodiment of a non-linear solution, the expansion of equation (3) can be solved with a non-linear solver to derive $\Delta x_{ov}$. In particular, the values of (a–a'), (b–b'), (c–c'), etc. (as applicable) in equation (3) can be determined as part of the determination of the derived nominal profile and/or the derived nominal profile model of a unit cell of interest. For example, once the derived nominal profile has been determined as part of the non-linear reconstruction, simulated or library optical information for a pupil corresponding to the derived nominal profile (e.g., corresponding to a perturbation of the derived nominal profile for a particular change in overlay (e.g., $\Delta x_{ov}$)) can be obtained and then the values of a, b, c, etc. (as applicable) can be determined for each pixel in the pupil with a non-linear solver that, e.g., iterates through solutions (e.g., responsive to one or more perturbations in overlay (e.g., $\Delta x_{ov}$)) in order to minimize the residual. The result is a vector of a values for the pupil (each a value corresponding to a pixel of the pupil), a vector of b values for the pupil (each b value corresponding to a pixel of the pupil), a vector of c values for the pupil (each a value corresponding to a pixel of the pupil), and so on as applicable. These vectors can then be combined with a vector of $S_i$ values determined from a measured pupil of a target having the unit cell of interest. A non-linear solver that, e.g., iterates through solutions in order to minimize the residual, can take these input vectors and then solve for the overlay $\Delta x_{ov}$.

While the discussion above has focused on using a model that models the physical profile of the unit cell, in an embodiment, the weightings can be derived using a data driven technique that does not require physical profile modelling or can be derived with a data driven technique that supplements physical profile modeling. So, in an embodiment, the data driven technique can advantageously not require a physical profile model; this can be useful, for example, for limiting the sharing of confidential information because the physical profile modeling starts with, and determines, details regarding the unit cell (and thus the target) which can be sensitive information if the unit cell is a device pattern structure. In an embodiment, the data driven technique can be enable relatively quick determination of, for example, the weights as discussed above to translate measured optical information (e.g., pupil intensity) into a patterning process parameter (e.g., overlay). In an embodiment, the data driven technique enables determination of the patterning process parameter in an early stage since as discussed below the data technique driven may need only measured data and an associated reference.

So, in an embodiment, the data driven technique involves processing data measured ("get" data) from one or more substrates having physical instances of the unit cell of interest patterned thereon as one or more targets, with one or more certain set values of the patterning process parameter (e.g., overlay) of interest. This combination of "set" intentional values of a certain patterning process parameter (e.g., overlay) to create patterns along with data measured from those patterns ("get" data) is referred to as a "set-get" process. For example, an overlay of a particular amount of the physical instance of unit cell is created as part of the patterning process and then the target having the physical instance of the unit cell is measured to obtain, e.g., a pupil image thereof (i.e., "get" data). In an embodiment, a plurality of substrates can be patterned and measured in this manner. In an embodiment, a plurality of different set values of overlay are created, which different values of overlay can be on one substrate, can be across different substrates, etc. In an embodiment, each substrate will have a plurality of targets measured, yielding, e.g., a plurality of pupil images. In an embodiment, the overlay can be created by inducing a magnification change from the design magnification between patterning different parts of the physical instance of the unit cell. In an embodiment, the overlay can be created by providing an intentional translation from the design positioning between patterning different parts of the physical instance of the unit cell. Thus, the result is a deliberate applied overlay in targets that are, e.g., induced by the lithographic apparatus.

In an embodiment, in general, there is obtained measurement data and associated reference values. So, in an embodiment, deliberate overlay need not be provided if there are different overlays but those overlays are determined by another means (e.g., from a scanning electron microscope).

In an embodiment, critical dimension uniformity substrates with corresponding reference data (e.g. coming from a CD-SEM) can be used as the input data. With the measured data and the reference values, the data-driven approach can find, as discussed herein, weights such that inferred overlay values resemble the reference values. So, while the discussion of the data-driven technique will focus on measured optical information and pupil representations obtained at intentionally set overlay value, they can be generally applied to more general measurement data and associated reference values (whether measured or intentionally set).

Further, while the techniques here relate to a particular overlay (e.g., an overlay in the X-direction), it will be appreciated that the techniques here can be repeated for different overlays (e.g., an overlay in the Y-direction, overlay between structures in different layers, etc.) using corresponding measurement data and reference values. Thus, different weights sets can be determined for different overlays.

Figure 13:
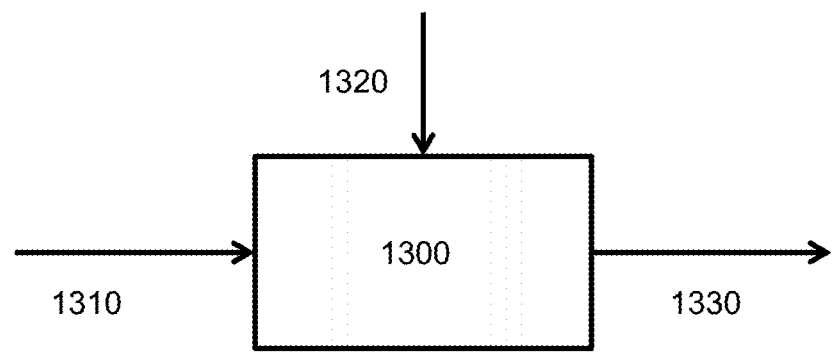
FIG. 13 depicts a high-level flow of an embodiment of a data driven technique.

So, referring to FIG. 13, a high-level flow of an embodiment of a data driven technique is depicted. At 1300, a calculation is performed to derive the weights as discussed above to translate measured optical information (e.g., pupil intensity) into a patterning process parameter (e.g., overlay). In particular, the calculation uses several inputs. One of the inputs is the set values 1320 of a set-get process for a target having a physical instance of the unit cell of interest. As noted above, a plurality of instances of a target can be measured across one or more substrates, wherein one or more instances of the target have a different value of intentional set value of a patterning process parameter than one or more other instances of the target. A further input is measured optical information 1310 for those instances of the target at different set values. In an embodiment, the optical information 1310 is a plurality of pupil representations, each corresponding to an instance of the target. Then, inputs 1310 and 1320 are processed in a data driven technique to arrive at the weights 1330. Examples of such a data driven technique are described hereafter.

In an embodiment, an example of a data driven technique to find a vector of the weights w is to minimize the following objective or merit function to arrive at the weights w:

$$\arg\min_{w,c} \Sigma_{i=1}^{D} \|P_i^T w - s_i - 1 c_i\|^2 \quad (6)$$

wherein w is a vector of the weights for combination with values of a measured optical characteristic (e.g., intensity) to determine a patterning process parameter (e.g., overlay), each weight corresponding to a pixel value of the pupil, $P_i$ is a matrix with each column containing the pixel values of the measured optical characteristic from a measured pupil of an instance of a target obtained from a substrate i patterned so as to obtain a particular set value of the patterning process parameter (which matrix is then transposed so that the columns becomes the pixels of the pupil, the rows become the one or more instances of the target on the substrate, and the values in the matrix are the values of measured optical characteristic at the respective pixels), $s_i$ is a vector containing the corresponding set values of the patterning process parameter for the one or more instances of the target on the one or more substrates i, each set value corresponding to a patterning process parameter value, 1 is a unit vector of the size of the number of set values, and $c_i$ is an offset difference between the set-values of the patterning process parameter and inferred values of the patterning process parameter ($P_i^T w$) for each substrate, and D is the number of substrates measured. The matrix $P_i$ can be combination of different results for each instance of the target. For example, a target can be measured with different wavelengths, different polarizations, etc. So, these results can be concatenated to each column so, for example, a single column can have values for the pixels of a pupil a target measured with a first wavelength and a first polarization, which are followed by values in the column for pixels of a pupil of the target measured with a second different wavelength or followed by values in the column for pixels of a pupil of the target measured with a second different polarization (and which can then be followed by further values at one or more different polarizations and/or wavelengths).

So, in effect, this function finds the weight vector w, such that the inferred values $P_i^T w$ for each substrate i looks as similar as possible (in a L2 regularization norm sense) as the set-values $s_i$ apart from an offset $c_i$. In principle, the optimal weights and offsets can be computed by a matrix inversion. Since the pixel values of the measured optical characteristic are taken with one or more particular metrology apparatuses, the obtained weights can be normalized by calibration data to reduce the impact of the particular metrology apparatus itself on the results.

Instead of or in addition to finding the weights as described above using an objective or merit function as the data driven technique, the data driven technique can use a machine learning algorithm, like a neural network, or a non-linear method to determine the weights based on measured pupils of targets with intentionally provided difference in the patterning process parameter (e.g., overlay) of interest.

In an embodiment, after the training (i.e., using the objective or merit function or the machine learning algorithm), the weights can checked using other data. There is a chance that the training results in an overfit; the data driven approach "just" fits the data to the set values. Therefore, a cross validation is done. New data with known set values are used to check the weights. This new data can also be a subset of the substrates at hand. So, in an embodiment, the training is done on a subset of substrates, and the validation is done on another (disjunct) subset of substrates.

Figure 14:
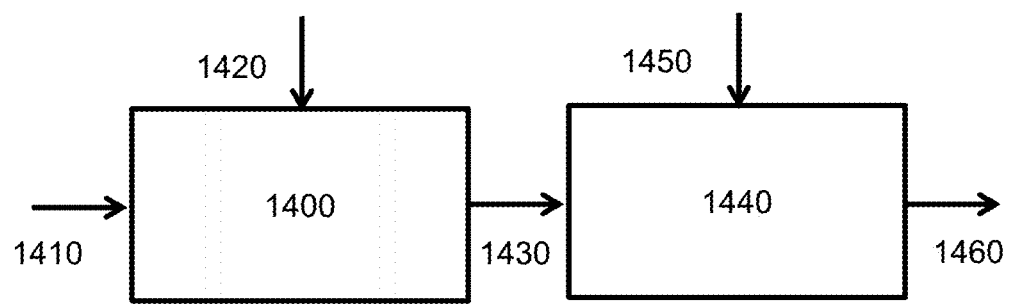
FIG. 14 depicts a high-level flow of an embodiment of a data driven technique in combination with a physical geometric model.

FIG. 14 depicts a high-level flow of an embodiment of a data driven technique in combination with a physical geometric model. In this embodiment, a data driven technique as described in relation to FIG. 13 can be used to derive weights, which are used to tune a physical geometric model (e.g., by using the Hessian to obtain better model nominal values, by changing the model nominal values, etc.) such that weights from physical geometric model (e.g., the (Moore-Penrose pseudo inverse of the) Jacobian of the physical geometric model) are the same or similar (e.g., in value, statistically, etc.) to the weights determined by the data driven technique. Thus, in an embodiment, a (scaled) weight vector w can be used to fine-tune the physical geometric model such that the physical geometric model is tuned so that the (Moore-Penrose pseudo inverse of) the Jacobian is similar to the (scaled) weight vector w.

So, in an embodiment, at 1400, a data driven technique (examples of which are described above) is performed to derive the weights as discussed above. The calculation uses several inputs. One of the inputs is the set values 1420 of a set-get process for a target having a physical instance of the unit cell of interest. As noted above, a plurality of instances of a target can be measured across one or more substrates, wherein one or more instances of the target have a different value of intentional set value of a patterning process parameter than one or more other instances of the target. A further input is measured optical information 1410 for those instances of the target at different set values. In an embodiment, the optical information 1410 is a plurality of pupil representations, each corresponding to an instance of the target. Then, inputs 1410 and 1420 are processed in a data driven technique to arrive at the weights 1430.

The weights 1430 are input to a process 1440 to fine-tune a physical geometric model using the weights 1430. The process 1440 obtains a physical profile 1450 for the unit cell (which the process 1440 uses to derive a physical profile model) or obtains a physical profile model 1450 for the unit cell (which the process 1440 uses). In an embodiment, the physical profile is the derived nominal profile and/or the derived nominal profile model of a unit cell as discussed above.

The process 1440 uses the physical geometric model to derive weights that correspond to weights 1430. Those weights are then compared to the weights 1430. The comparison can involve a matching of magnitudes, a statistical analysis, a fitting evaluation, etc. If there is a significant difference (e.g., by evaluation of the comparison against a threshold), one or more parameters of the physical profile can be tuned. For example, one or more physical profile parameters (e.g., CD, sidewall angle, material heights, etc.) can be tuned so that the results of the comparison come closer than or equal to, e.g., a certain threshold. In an embodiment, the Hessian can be used to do this fine-tuning, or can be done using a non-linear solver (including one or more forward calls (e.g., a Maxwell solver)). The tuning and comparison can be iterated until the threshold is met or crossed. Then, the tuned physical geometric model can output updated weights 1460 for use in combining with measured optical information of a target of interest to derive a patterning process parameter value.

Figure 15:
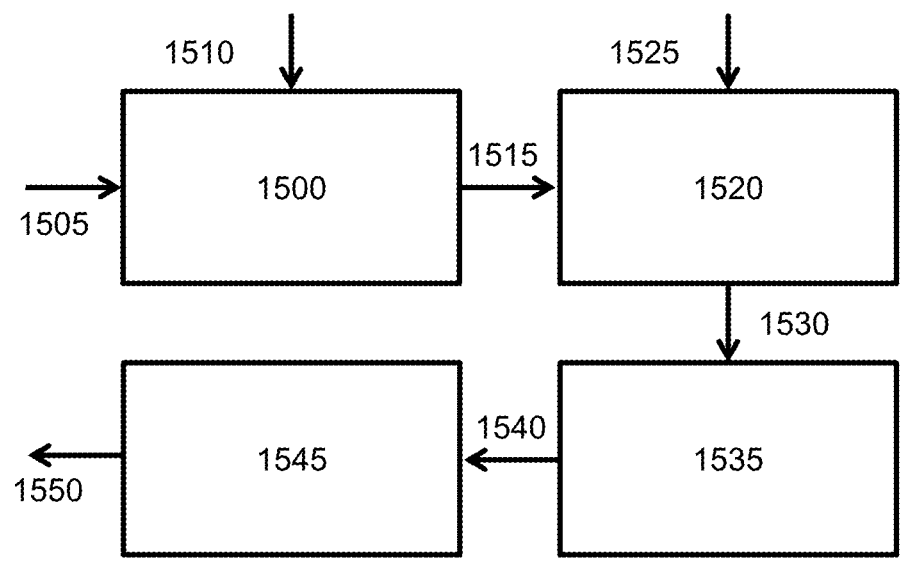
FIG. 15 depicts a high-level flow of an embodiment of a data driven technique in combination with a physical geometric model.

FIG. 15 depicts a high-level flow of a further embodiment of a data driven technique in combination with a physical geometric model. When a physical geometric model behaves similarly as measured data, the physical geometric model can be used to predict the impact of process variations. So, in an embodiment, the Hessian of the physical geometric model can be used to tune the weights such that the weights become (more) orthogonal to process variations that were not in the data used in the data driven technique to obtain the weights used to tune the physical geometric model.

This approach of using the Hessian to tune the weights can also be done without the data driven technique. That is, this technique to use the Hessian to update the weights can be done with a physical geometric model approach described in association with FIG. 11. In this case, for example, the weights can be tuned such that the weights become (more) orthogonal to process variations that were not in the data used to obtain the derived nominal profile and/or the derived nominal profile model of a unit cell as discussed above. Through such tuning, the weights become more robust to process variations not observed in measured data used to create the physical geometric model.

So, in an embodiment, at 1500, a data driven technique (examples of which are described above) is performed to derive the weights as discussed above. The calculation uses several inputs. One of the inputs is the set values 1510 of a set-get process for a target having a physical instance of the unit cell of interest. As noted above, a plurality of instances of a target can be measured across one or more substrates, wherein one or more instances of the target have a different value of intentional set value of a patterning process parameter than one or more other instances of the target. A further input is measured optical information 1505 for those instances of the target at different set values. In an embodiment, the optical information 1505 is a plurality of pupil representations, each corresponding to an instance of the target. Then, inputs 1505 and 1510 are processed in a data driven technique to arrive at the weights 1515.

The weights 1515 are input to a process 1520 to fine-tune a physical geometric model using the weights 1515. The process 1520 obtains a physical profile 1525 for the unit cell (which the process 1520 uses to derive a physical profile model) or obtains a physical profile model 1525 for the unit cell (which the process 1520 uses). In an embodiment, the physical profile is the derived nominal profile and/or the derived nominal profile model of a unit cell as discussed above.

The process 1520 uses the physical geometric model to derive weights that correspond to weights 1515. Those weights are then compared to the weights 1515. The comparison can involve a matching of magnitudes, a statistical analysis, a fitting evaluation, etc. If there is a significant difference (e.g., by evaluation of the comparison against a threshold), one or more parameters of the physical profile can be tuned. For example, one or more physical profile parameters (e.g., CD, sidewall angle, material heights, etc.) can be tuned so that the results of the comparison come closer than or equal to, e.g., a certain threshold. In an embodiment, the Hessian can be used to do this fine-tuning, or can be done using a non-linear solver (including one or more forward calls (e.g., a Maxwell solver)). The tuning and comparison can be iterated until the threshold is met or crossed.

But, as will be appreciated, a patterning process can vary during execution and differently for different executions of the patterning process. Thus, data obtained for the data driven technique doesn't account for all the possible patterning process variations. But, when the tuning of the physical geometric model has made it so that behaves similarly as measured data, the physical geometric model can be used to predict the impact of process variations and adjust the weights accordingly.

So, in an embodiment, the tuned physical geometric model 1530 is used to compute the Hessian of the tuned physical geometric model at 1535. The Hessian 1540 is then used to tune the weights at 1545 such that the weights become (more) orthogonal (i.e., robust) to process variations that were not in the data used in the data driven technique to obtain the weights used to tune the physical geometric model. In other words, the weights are tuned to be more likely to yield an accurate result when combined with measurement data from a substrate even when the substrate is subject to process variation.

A non-limiting example of how the Hessian can be used to fine-tune the weights is described here in the context of overlay; a different patterning process parameter could be used as appropriate. In this example, it is assumed only one overlay type is evaluated (e.g., overlay in the X direction). Fine-tuning with multiple overlay types is also possible.

In this embodiment of using the Hessian to fine-tune the weights, an overlay response is estimated from data measured from one or more set-get substrates by applying a single value decomposition to the data. It is assumed that an eigenvector d (which has length 1) corresponds to the overlay response. Then the following equation is solved to find vector $\Delta p$:

$$\mathrm{argmin}_{\Delta \underline{p}} \left\| d - \frac{\underline{J} + H \Delta \underline{p}}{\|\underline{J} + H \Delta \underline{p}\|} \right\| \quad (7)$$

wherein J is the Jacobian with respect to the overlay parameter, and the Hessian H is a matrix where the columns contain the partial derivatives with respect to a process variation (e.g., a variation in CD, material height, etc.) and the overlay parameter (both the Jacobian and the Hessian are obtained from the model as described above). The determined vector $\underline{\Delta p}$ then corresponds to the delta parameters to be applied to the non-overlay parameters in the model to obtain an updated (e.g., better) model.

To make the weights robust to process variations (i.e. orthogonal to the process variations), the following technique can be used. A pupil $\underline{I}$ can be defined by the following second order Taylor expansion:

$$\underline{I} = Jo + H \underline{\Delta p} o \quad (8)$$

where J is the Jacobian with respect to the overlay parameter, and H is a matrix where the columns contain the partial derivatives with respect to a process variation (e.g., a variation in CD, material height, etc.) and the overlay parameter. The vector $\underline{\Delta p}$ contains the corresponding process variations. Thus, for a given structure and for a given process variation instance $\underline{\Delta p}$ with an overlay value o, the pupil equals (approximately) $\underline{I}$. As will be appreciated, the above formulation can be extended to more overlay parameters by adding these contributions as well. Moreover, this formulation is an approximation because the higher orders in the Taylor expansion are neglected.

Now, if the impact of the process variations is small, the weights are computed using the Penrose-Moore inverse of the Jacobian J. In the case of only one overlay parameter, the weights equal to $$\underline{w} = \frac{J}{\|J\|^2}.$$

And indeed, the weighted average (inner product) with the pupil results in the overlay value o ($\underline{\Delta p}=\underline{0}$), i.e., $$\langle \underline{I}, \underline{w} \rangle = \langle \underline{J}o, \underline{w} \rangle = \frac{o}{\|J\|^2} \langle \underline{J}, \underline{J} \rangle = o \quad (9)$$

However, when the process variations have a large impact, the overlay response changes:

$$\underline{I} = (\underline{J} + \underline{\Delta p} \times )o = \tilde{J}o \quad (10)$$

To make the weights robust to these variations, $$H\underline{w} = \underline{0} \quad (11)$$

This can be achieved by taking the weights w equal to the first row of the pseudo inverse of the matrix [J H]. Or in other words, the Hessian matrix H is concatenated to the Jacobian before the inversion. In this way, the weights become orthogonal to the process variations (but at some cost of precision).

Thus, from tuning 1545, tuned weights 1550 are output for use in combining with measured optical information of a target of interest to derive a patterning process parameter value.

Figure 16:
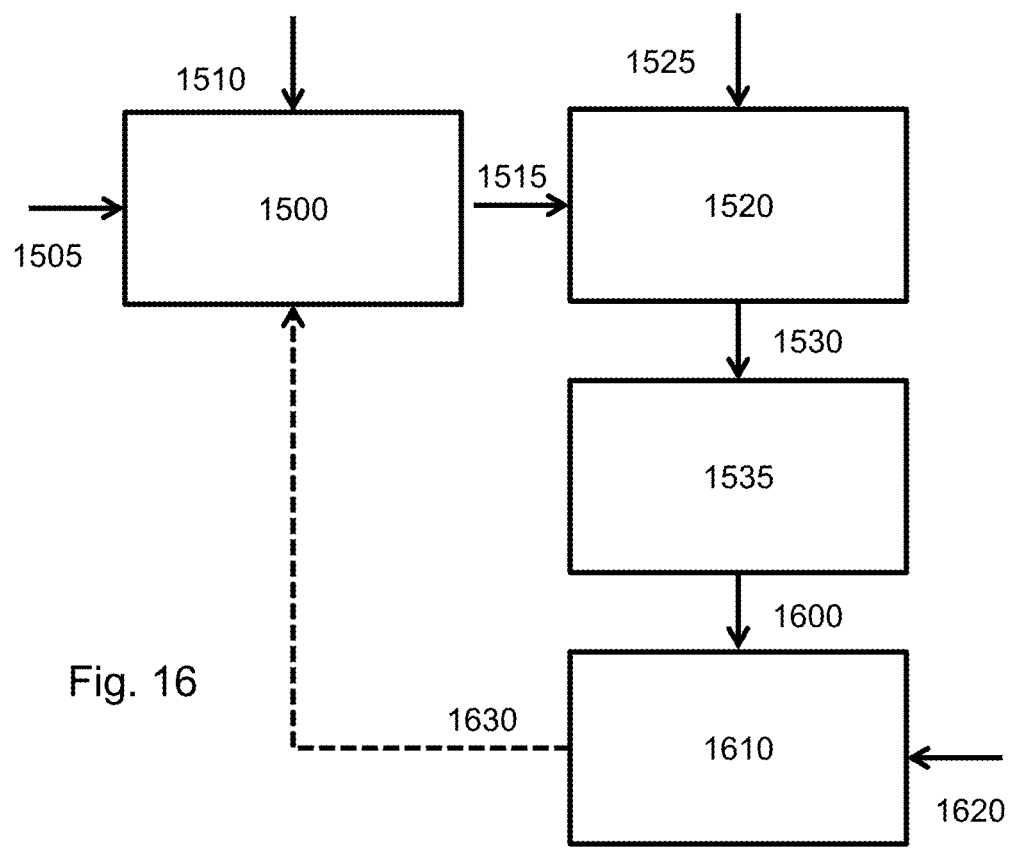
FIG. 16 depicts a high-level flow of an embodiment of a data driven technique in combination with a physical geometric model.

FIG. 16 depicts a high-level flow of a further embodiment of a data driven technique in combination with a physical geometric model. In this embodiment, the data input to the data driven technique is extended by including synthetic optical information (e.g., pupil representations) that contains process variations for the patterning process (e.g. the patterning process variation can be obtained from CD measurements). The synthetic optical information alone or in combination with the measured optical information can be used to find new weights using the data driven technique.

So, in an embodiment, at 1500, a data driven technique (examples of which are described above) is performed to derive the weights as discussed above. The calculation uses several inputs. One of the inputs is the set values 1510 of a set-get process for a target having a physical instance of the unit cell of interest. As noted above, a plurality of instances of a target can be measured across one or more substrates, wherein one or more instances of the target have a different value of intentional set value of a patterning process parameter than one or more other instances of the target. A further input is measured optical information 1505 for those instances of the target at different set values. In an embodiment, the optical information 1505 is a plurality of pupil representations, each corresponding to an instance of the target. Then, inputs 1505 and 1510 are processed in a data driven technique to arrive at the weights 1515.

The weights 1515 are input to a process 1520 to fine-tune a physical geometric model using the weights 1515. The process 1520 obtains a physical profile 1525 for the unit cell (which the process 1520 uses to derive a physical profile model) or a physical profile model 1525 for the unit cell (which the process 1520 uses). In an embodiment, the physical profile is the derived nominal profile and/or the derived nominal profile model of a unit cell as discussed above.

The process 1520 uses the physical geometric model to derive weights that correspond to weights 1515. Those weights are then compared to the weights 1515. The comparison can involve a matching of magnitudes, a statistical analysis, a fitting evaluation, etc. If there is a significant difference (e.g., by evaluation of the comparison against a threshold), one or more parameters of the physical profile can be tuned. For example, one or more physical profile parameters (e.g., CD, sidewall angle, material heights, etc.) can be tuned so that the results of the comparison come closer than or equal to, e.g., a certain threshold. The tuning and comparison can be iterated until the threshold is met or crossed.

So, in an embodiment, the tuned physical geometric model 1530 is used to compute the Hessian of the tuned physical geometric model at 1535. The Hessian 1600 is then used to generate at 1610 synthetic optical information (e.g., one or more pupil representations). Synthetic optical information is simulated optical information. The synthetic optical information is intended to mimic one or more expected process variations in the patterning process. In an embodiment, data 1620 regarding one or more process variations in the patterning process can be used in combination with the Hessian 1600 to derive the synthetic optical information. In an embodiment, a synthetic pupil $\underline{I}$ can be generated by substituting different overlay values o and different parameter variations $\Delta p$ in the equation (8) above, wherein the weights correspond to $$\underline{w} = \frac{J}{\|J\|^2}.$$

While equation (8) described above is directed to a single overlay parameter, the technique can be extended to more overlay parameters by adding those contributions as well. Furthermore, the technique using equation (8) is an approximation, because the higher orders in the Taylor expansion are neglected. The data 1620 can comprise, for example, information that describes the kind and extent of a process variation (e.g., an indication that overlay, CD, etc. can vary by a certain percentage). The data 1620 can be obtained by a measurement in the patterning process, e.g., overlay, CD, etc. measurement. The data 1620 is thus used with the Hessian 1600 to generate simulated optical information 1630 that includes an expected process variation. The synthetic optical information 1630 can also include one or more associated estimated set values associated with the synthetic optical information 1630. The synthetic optical information 1630 (and any associated set values) is then input to the data driven technique 1500 for analysis alone or in combination with the measured optical information, to find new weights using the data driven technique.

Figure 17:
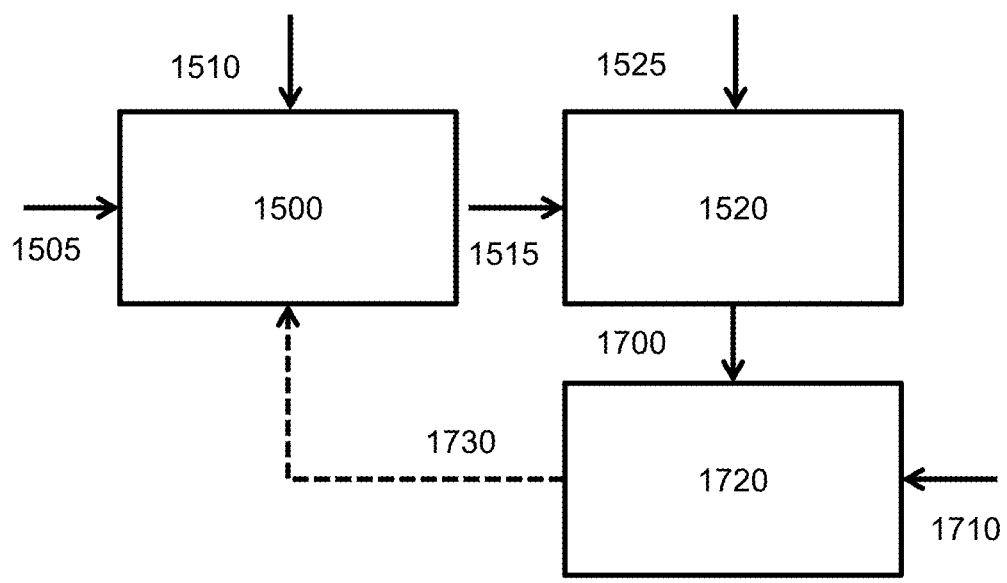
FIG. 17 depicts a high-level flow of an embodiment of a data driven technique in combination with a physical geometric model.

FIG. 17 depicts a high-level flow of a further embodiment of a data driven technique in combination with a physical geometric model. This embodiment is similar to the embodiment of FIG. 16 except that instead of computing a Hessian a forward call is made to a non-linear solver (e.g., a Maxwell solver) for every process variation to obtain the synthetic optical information.

So, in an embodiment, at 1500, a data driven technique (examples of which are described above) is performed to derive the weights as discussed above. The calculation uses several inputs. One of the inputs is the set values 1510 of a set-get process for a target having a physical instance of the unit cell of interest. As noted above, a plurality of instances of a target can be measured across one or more substrates, wherein one or more instances of the target have a different value of intentional set value of a patterning process parameter than one or more other instances of the target. A further input is measured optical information 1505 for those instances of the target at different set values. In an embodiment, the optical information 1505 is a plurality of pupil representations, each corresponding to an instance of the target. Then, inputs 1505 and 1510 are processed in a data driven technique to arrive at the weights 1515.

The weights 1515 are input to a process 1520 to fine-tune a physical geometric model using the weights 1515. The process 1520 obtains a physical profile 1525 for the unit cell (which the process 1520 uses to derive a physical profile model) or a physical profile model 1525 for the unit cell (which the process 1520 uses). In an embodiment, the physical profile is the derived nominal profile and/or the derived nominal profile model of a unit cell as discussed above.

The process 1520 uses the physical geometric model to derive weights that correspond to weights 1515. Those weights are then compared to the weights 1515. The comparison can involve a matching of magnitudes, a statistical analysis, a fitting evaluation, etc. If there is a significant difference (e.g., by evaluation of the comparison against a threshold), one or more parameters of the physical profile can be tuned. For example, one or more physical profile parameters (e.g., overlay, CD, sidewall angle, etc.) can be tuned so that the results of the comparison come closer than or equal to, e.g., a certain threshold. The tuning and comparison can be iterated until the threshold is met or crossed.

So, in an embodiment, the tuned physical geometric model 1700 is used to compute at 1720 synthetic optical information like as discussed above. Like as discussed above, data 1710 regarding one or more process variations in the patterning process can be used in combination with the tuned physical geometric model 1700 to derive the synthetic optical information. For example, the data 1710 can comprise information that describes the kind and extent of a process variation (e.g., an indication that overlay, CD, etc. can vary by a certain percentage). The data 1710 can be obtained by a measurement in the patterning process, e.g., overlay, CD, etc. measurement. As noted above, the process at 1720 can use a forward call to a non-linear solver (e.g., a Maxwell solver) for the process variation to obtain the synthetic optical information. The data 1710 is thus used with the tuned physical geometric model 1700 to generate simulated optical information 1730 that includes an expected process variation. The synthetic optical information 1730 can also include one or more associated estimated set values associated with the synthetic optical information 1730. The synthetic optical information 1730 (and any associated set values) is then input to the data driven technique 1500 for analysis alone or in combination with the measured optical information, to find new weights using the data driven technique.

In FIGS. 10A-10C, a relatively simple example of a unit cell was presented in which an overlay in essentially only one direction caused a change in the symmetry of the unit cell. In particular, in the unit cell of FIGS. 10A-10C, an overlay change in the X direction resulted in a change in the symmetry/asymmetry of the unit cell, while an overlay change in the Y direction does not result in a change in the symmetry of the unit cell. This is a consequence of the unit cell of FIGS. 10A-10C having two structures 1000, 1005 which are configured in a particular geometric way such that an overlay in essentially only one direction caused a change in the symmetry of the unit cell. Of course, this can be designed in this manner by appropriate selection of structures. However, it could be that an existing structure, such as a device structure, can be identified that has a particular geometry such that an overlay in essentially only one direction causes a change in the symmetry of the unit cell. So, various unit cells can be chosen or designed that enable determination of an overlay in essentially only one direction (which need not be in the X direction).

However, advantageously, a unit cell can be identified or designed that is configured so that a change in the symmetry of the unit cell results for two or more different overlays. In an embodiment, the different overlays can be in different directions. Specifically, in an embodiment, a first overlay can be in the X direction, while a second overlay can be in the Y direction. In an embodiment, the different overlays can each be between a different combination of structures or parts of the unit cell. In an embodiment, those structures can be in a same layer and/or in different layers of the target. Specifically, in an embodiment, a first overlay can be between a first structure and a second structure of the unit cell and a second overlay can be between the first structure (or second structure) and a third structure of the unit cell or between a third structure and a fourth structure of the unit cell. In this case, the first overlay and second overlay can be in the same direction. Naturally, there can be a combination of different overlays in different directions and different overlays from combinations of structures of the unit cell. For example, a first overlay can be in the X direction for a first structure in a first layer and a second structure in a second lower layer and a second overlay can be in the Y direction for the first structure in the first layer and a third structure in the a third layer lower than the second layer. Thus, numerous combinations of overlay can be determined through appropriate identification or design of the unit cell (and thus the target).

Moreover, as will be appreciated, a determination of an overlay in the X direction and the Y direction can enable through appropriate combination determine a total overlay (in X and Y). Similarly, to enable the determination of total overlay for multiple different structures between which overlay can occur, the overlay for each of those structures needs to be determined. So, as an example, for a unit cell that has 4 distinct structures in 4 layers between which overlay can occur (with one of the layers being a reference layer), then 6 overlays (X and Y for each layer) could be determined to enable determination of the total overlay for the unit cell. Of course, a sub-combination could be determined as desired to arrive at one or more different overlays of interest among the 4 layers.

Figure 18:
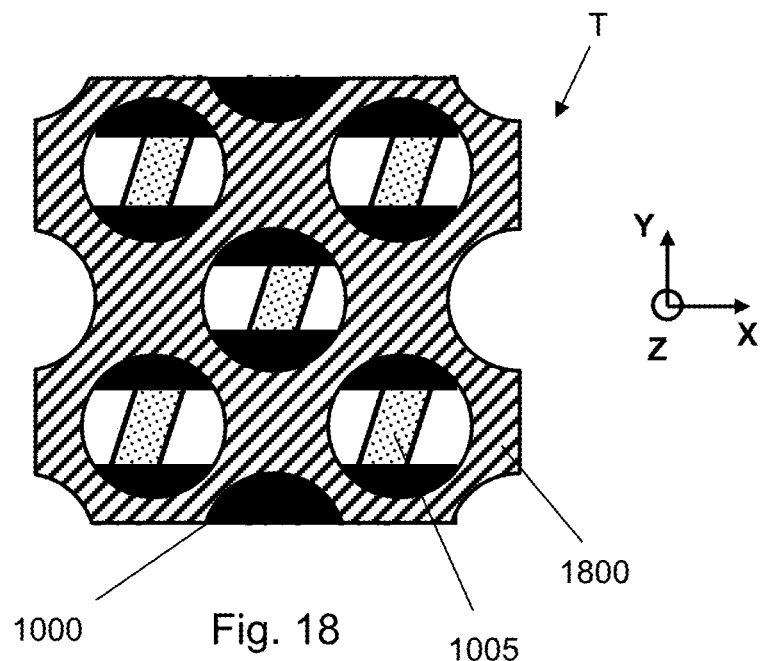
FIG. 18 schematically depicts an embodiment of a multiple overlay unit cell of a target.

FIG. 18 depicts an example embodiment of a multiple overlay unit cell of a target. Like the unit cells of FIGS. 10A-10C, this unit cell comprises a first structure 1000 and a second structure 1005. Additionally, this unit cell has a third structure 1800 that is in this embodiment in a layer above, in the Z direction, the first and second structures 1000, 1005. In this embodiment, asymmetry of this unit cell can be created by one or more different overlays. For example, a relative shift between the structure 1005 and the structure 1800 in the X direction can yield an overlay in the X direction which causes asymmetry. As another example, a relative shift between the structure 1005 and the structure 1000 in the Y direction can yield an overlay in the Y direction which causes asymmetry. As a further example, a relative shift between the structure 1000 and the structure 1800 in the Y direction can yield a further overlay in the Y direction which causes asymmetry.

Figure 19:
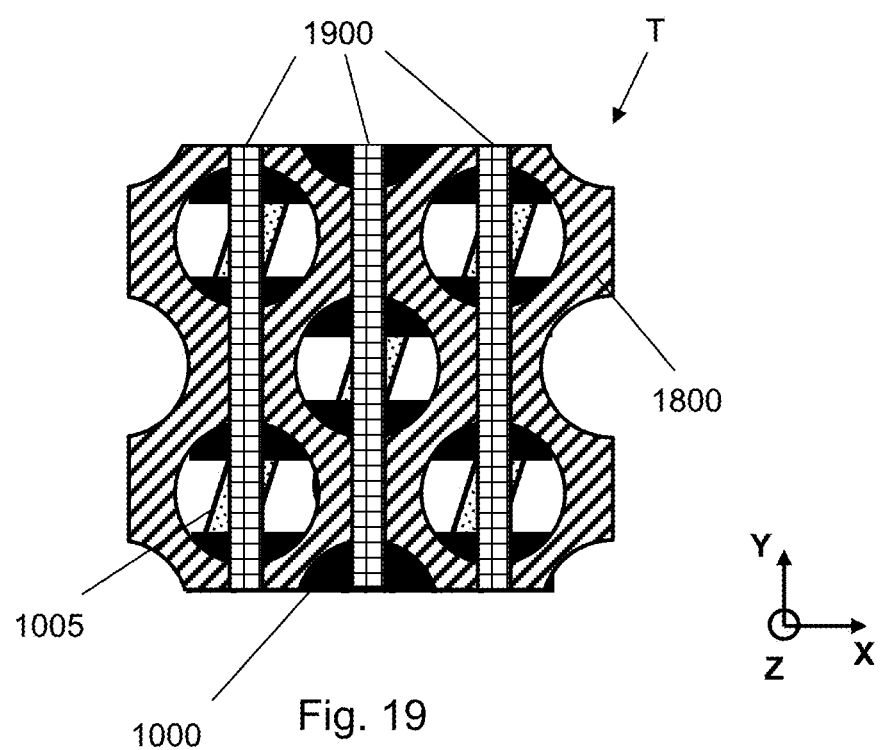
FIG. 19 schematically depicts an embodiment of a multiple overlay unit cell of a target.

FIG. 19 depicts a further example embodiment of a multiple overlay unit cell of a target. Like the unit cells of FIGS. 10A-10C, this unit cell comprises a first structure 1000 and a second structure 1005. Additionally, like the unit cell of FIG. 18, this unit cell has a third structure 1800 that is in this embodiment in a layer above, in the Z direction, the first and second structures 1000, 1005. Further, this unit cell has a fourth structure 1900 that is in this embodiment in a layer above, in the Z direction, the first, second and third structures 1000, 1005, 1800. Like the unit cell of FIG. 18, in this embodiment, asymmetry of this unit cell can be created by one or more different overlays. For example, a relative shift between the structure 1005 and the structure 1800 in the X direction can yield an overlay in the X direction which causes asymmetry. As another example, a relative shift between the structure 1005 and the structure 1900 in the X direction can yield an overlay in the X direction which causes asymmetry. As another example, a relative shift between the structure 1005 and the structure 1000 in the Y direction can yield an overlay in the Y direction which causes asymmetry. As a further example, a relative shift between the structure 1000 and the structure 1800 in the Y direction can yield a further overlay in the Y direction which causes asymmetry.

Thus, in an embodiment, measurement of an illuminated physical instance of the unit cell of FIG. 18 or of FIG. 19 will yield optical information that could potentially include multiple different overlays if there are in fact multiple different overlays. For example, referring to FIG. 18, if the symmetry of the unit cell of FIG. 18 represents zero overlay and there is a shift in the X and Y of the structure 1005 (e.g., a shift in direction that is not 0, 90, 180 or 270 degrees) from its zero overlay position relative to its overlying structures, that shift would cause an asymmetry due to the relative shift between the structure 1005 and the structure 1800 in the X direction and the relative shift between the structure 1005 and the structure 1000 in the Y direction. So, it would be desirable to determine both the overlay for structure 1005 in the X and Y directions (which combination will yield the total overlay of structure 1005).

As discussed hereafter, a technique is presented that can determine, from the optical characteristic values, a value of a first overlay for the physical instance of the unit cell separately from a second overlay for the physical instance of the unit cell that is also obtainable from the same optical characteristic values, wherein the first overlay is in a different direction than the second overlay (e.g., X direction overlay and Y direction overlay) or between a different combination of parts of the unit cell than the second overlay (e.g., a first overlay between structure 1005 and structure 1800 and a second overlay between structure 1005 and structure 1000 or between structure 1000 and structure 1800, where the first overlay and the second overlay could possibly be in the same direction).

That is, in an embodiment, weights are determined to decouple first overlay information in an optical characteristic value from second (or more) overlay information in the same optical characteristic value. Thus, in an embodiment, by applying specially selected weights, the combination of the weights with optical characteristic values will yield a particular overlay of interest as distinguished from other possible overlay information in the same optical characteristic values. In effect, the weights will feature the overlay of interest and lessen one or more other overlays. Of course, different sets of weights can be constructed for each overlay of interest such that the optical characteristic values can be processed to yield different values for each of the different overlays of interest.

Figure 20:
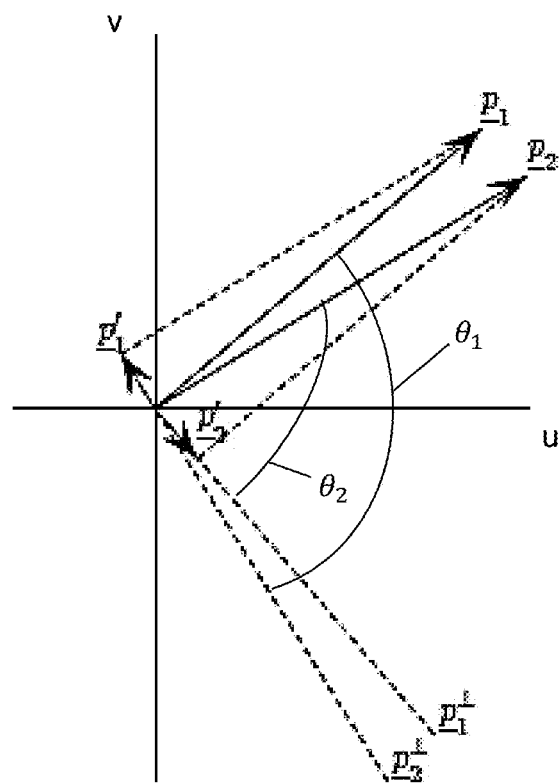
FIG. 20 depicts an example graph of two vectors corresponding to two different overlays.

This technique will be described in respect of the graph of FIG. 20. The graph of FIG. 20 presents a graphical presentation of the technique but in practice the graph need not be constructed as all the processing can be done mathematically without the need to create the graph. Further, the technique is described in respect of the model of FIG. 11. But, models (and associated other techniques) described in respect of other Figures herein could be used.

Further, this example is presented in terms of deriving the linear version of the weights from the model. That is, in an embodiment, the weights are derived from the (Moore-Penrose pseudo inverse of) the Jacobian.

So, in this linear case, to reconstruct a particular parameter such as an overlay in a certain direction, the Jacobian can be inverted. But, how the column of the parameter of interest is correlated to the remaining columns determines how easily it will be to reconstruct this parameter.

So, having, e.g., the nominal profile model for a unit cell of interest (e.g., the unit cell of FIG. 18), at least two vectors can be generated. A first overlay vector $p_1$ represents a first overlay of interest (e.g., a X-direction overlay) within the unit cell and a second overlay vector $p_2$ represents a second overlay of interest (e.g., a Y-direction overlay). As will be appreciated, further vectors can be created for additional overlays of interest.

Further, for each of the two overlay vectors, one or more pixels of a pupil representation corresponding to an expected measurement of the physical instance of the unit cell are selected. In this embodiment, a pair of pixels is selected for each overlay vector, wherein each pair of pixels comprises symmetrically located pixels as described earlier. Desirably, the pairs of pixels are selected from the asymmetric radiation distribution portion of the pupil representation as discussed above.

Now, the first overlay vector $p_1$ corresponds to the response (in this case, asymmetric signal between the pixels creating a pair) in the pairs of pixels to a change in the first overlay of interest for the first overlay vector (leaving all other parameters unchanged, i.e., no change in the second overlay of interest). This response can be generated using the nominal profile model by inducing a change in the first overlay of interest (e.g., 1 nm change) and then calculating the optical response (e.g., intensity) in the pairs of pixels to that change.

Similarly, the second overlay vector $\underline{p_2}$ corresponds to the response (in this case, asymmetric signal between the pixels creating a pair) in the pairs of pixels to a change in the second overlay of interest for the second overlay vector (leaving all other parameters unchanged, i.e., no change in the first overlay of interest). This response can be generated using the nominal profile model by inducing a change in the second overlay of interest (e.g., 1 nm change) and then calculating the optical response (e.g., intensity) in the pairs of pixels.

The resulting vectors are graphed in FIG. 20 wherein the horizontal axis u corresponds to the asymmetric intensity ($I_i$-$I_i'$) between symmetrically positioned pixels of the first pixel pair and the vertical axis v corresponds to the asymmetric intensity ($I_i$-$I_i'$) between symmetrically positioned pixels of the second pixel pair. So, FIG. 20 shows two highly correlating vectors $\underline{p_1}$ and $\underline{p_2}$.

So, to decouple and separate the contributions of the first and second overlays of interest to the pixel pairs, the vector $\underline{p_1}$ is back-projected onto a vector $\underline{P_1}^\perp$, which is a vector orthogonal to the vector $\underline{p_2}$, to form vector $p'_1$ and the length of projected vector $p'_1$ is divided by the cosine of the angle $\theta_1$ between vector $\underline{p_1}$ and $\underline{P_2}^\perp$. This vector then helps to isolate the first overlay of interest from the intensity of the pixel pairs (and by extension other pixel pairs in the pupil representation).

Additionally or alternatively, the vector $\underline{p_2}$ is back-projected onto a vector $\underline{P_1}^\perp$, which is a vector orthogonal to the vector $\underline{p_1}$, to form vector $p'_2$ and the length of projected vector $p'_2$ is divided by the cosine of the angle $\theta_2$ between vector $\underline{p_2}$ and $\underline{P_1}^\perp$. This vector then helps to isolate the second overlay of interest from the intensity of the pixels pairs (and by extension other pixel pairs in the pupil representation).

So, referring back to equations (3) and (4), $S_i$ represents the asymmetric intensity ($I_i$-$I_i'$) between symmetrically positioned pixels of a pixel pair. So, the first overlay vector $\underline{p_1}$ can correspond to the response in a first pixel pair having $S_i$ of $U_0$ and a second pixel pair having $S_i$ of $V_0$ to a change in the first overlay of interest. Similarly, the second overlay vector $\underline{p_2}$ can correspond to the response in those first and second pixel pairs to a change in the second overlay of interest. Accordingly, the vector $p'_1$ and/or the vector $p'_2$ can be constructed; here both are constructed for explanatory purposes. The vector $p'_1$ and the vector $p'_2$ are defined in terms of the intensity u corresponding to the first pixel pair corresponding to $U_0$ and in terms of the intensity v corresponding to the second pixel pair corresponding to $V_0$. So, vector $p'_1$ and vector $p'_2$ can be specified as:

$$\underline{p'_1} = (u'_1, v'_1) \quad (12)$$

$$\underline{p'_2} = (u'_2, v'_2) \quad (13)$$

So, now in the linear context described above and referring to equation (4), an overlay value of the first overlay of interest can then be defined based on $U_0$, $V_0$, and vectors $p'_1$ and $p'_2$ as follows:

$$OV_{\underline{p1}} = (u'_1 U_0 + v'_1 V_0)/\cos\theta_1 \quad (14)$$

Additionally or alternatively, an overlay value of the second overlay of interest can then be defined based on $U_0$, $V_0$ and vectors $p'_1$ and $p'_2$ follows $$OV_{\underline{p2}} = (u'_2 U_0 + v'_2 V_0)/\cos\theta_2 \quad (15)$$

So, from equation (14), the weights to determine the first overlay of interest are, for respectively $U_0$ and $V_0$, the following:

$$\frac{u'_1}{\cos\theta_1}, \frac{v'_1}{\cos\theta_1} \quad (11)$$

Further, from equation (15), the weights to determine the second overlay of interest are, for respectively $U_0$ and $V_0$, the following:

$$\frac{u'_2}{\cos\theta_2}, \frac{v'_2}{\cos\theta_2} \quad (16)$$

So, as will be appreciated, this can be repeated for all, or substantially all, of the pixel pairs in the pupil representation so as to arrive at a set of weights $w_i$ for the first overlay of interest ($w_i^1$) and/or to arrive at a set of weights $w_i$ for the second overlay of interest ($w_i^2$). One or both of these can then applied to measured optical characteristic values in accordance with equation (4) to arrive at an overlay value for the respective overlay of interest. Of course, one or more further overlays of interest can be evaluated and one or more appropriate weight sets determined for them. As will be appreciated, in an embodiment, the sensitivity (e.g., Jacobian) to all of the different overlays of interest is included in the weights definition for a particular overlay of interest.

So, for example for a unit cell having 4 layers (with one of the layers being a reference layer) wherein a shift in each of the layers in the X and Y directions could cause a change in symmetry (e.g., cause an asymmetry, or cause a further asymmetry, or cause an asymmetric unit cell to become symmetric), then 6 vectors can be created (each being associated with a different pixel pair), the 6 vectors comprising a X-direction overlay vector for each of the layers and a Y-direction overlay vector for each of the layers. There could thus be 6 sets of weights to derive the respective overlays. Of course not all of the weight sets need to be derived if one of the vectors is not of interest (but in an embodiment, the sensitivity (e.g., Jacobian) to all of the different overlays of interest is included in the weights definition for the particular overlay of interest). Any other overlay can then be determined by appropriate mathematical combination of two or more of these overlays.

As will be appreciated, some shifts of a layer in a unit cell would not cause a change in symmetry and so the overlay corresponding to that shift cannot be determined from the unit cell. So, obviously, no vector would be defined for such a shift. So, taking FIG. 18 as an example, three vectors could be defined for that unit cell—one for the X-direction overlay and two for the different Y-direction overlays. So, one sets of weights can be determined that will give the overlay in the X-direction when combined with measured optical characteristic values. Or, a set of weights can be determined that will give one of the overlays in the Y-direction when combined with measured optical characteristic values and/or a set of weights can be determined that will give the other of the overlays in the Y-direction when combined with measured optical characteristic values. Of course, all three sets of weights can be determined or just two.

The discussion above has focused on a target formed by one or more instances of a symmetrical unit cell made up of structures of a device. Such a target can enable, through on-product measurement of radiation redirected by the on-product target, determination of an on-product value of a patterning process parameter. However, as described above, the target need not be made up of only device structures. In other words, a non-product target can be provided whose structures don't exclusively comprise device structures. For example, in an embodiment, a target can be specially created of structures that are not used to form the device but rather are merely used for measurement. Such a target can be provided, e.g., in a scribe lane away from the device (and thus provided in a part of a device patterning pattern away from the device pattern). In an embodiment, the target can be provided in among the device pattern (and thus provided among the features of a device pattern of a patterning device pattern). Where appropriate, a non-product target can comprise one or more device structures and one or more specially created structures that are not used to form the device but rather are merely used for measurement.

A non-product target can be useful if, for example, a patterning process parameter is being determined for a device pattern that cannot present symmetric unit cell instances. As another example, a non-product target can be useful if, for example, a patterning process parameter is being determined for a portion of a device pattern that doesn't have a symmetrical unit cell as described above that can give a measure of that patterning process parameter. For example, there can be cases of a structure for overlay after etch is desired to be determined using the symmetrical unit cell methods described above but has no symmetry. For example, logic circuits or structures have many process layers\steps that are each able to introduce a different overlay component that can break the symmetry of the structure. In the case of logic circuits for example, measurement on the device pattern typically cannot be performed due to the lack of a symmetric unit cell of logic circuit structures.

As a further example, the non-product target can be used in association with a device pattern that can present symmetric unit cell instances (and even if the unit cell can give a measure of all patterning process parameters of interest). This can be, for example, if the device pattern is complex, which can require significant computation time. Further, the device pattern may present potential cross-talk with signals of patterning process parameters not of interest. As an example, the pupil correlations of different overlay components might be so large that it is impossible to separate the different overlay errors.

Thus, a non-product target can be used with a device pattern that has instances of a symmetrical unit cell for a beam spot or with a device pattern that can't present instances of a symmetrical unit for the beam spot.

So, in an embodiment, a non-product target can be designed such that a particular type of patterning process parameter (e.g., overlay) of interest breaks a certain type of (pupil) symmetry of the non-product target; this is similar to the techniques described above. And, while overlay will be a focus of the discussion, like as discussed above, one or more different patterning process parameters than overlay may be determined.

Of course, for the non-product target to give a measure of the patterning process parameter, the non-product target will follow those process steps that are considered to be the main contributor to the patterning process parameter at issue. Thus, as discussed above, if, e.g., an overlay between two structures created in separate patterning processes are of interest, then the non-product target comprises a structure created in each of the separate patterning processes and desirably by a same or comparable process.

Further, breaking a certain type of geometric symmetry (e.g., Y-symmetry) leads to breaking the same type of symmetry in the pupil domain. So, a non-product target can be designed for a particular type of geometric symmetry such that a corresponding particular patterning process parameter value causes a break in the symmetry. For example, a Y-symmetry broken by an X-overlay. Further, where there is symmetry in more than one direction using a target that is designed such that a different type of patterning process parameter (e.g., different overlay type such as overlay in X and overlay in Y) breaks a different type of symmetry enables monitoring the induced asymmetry (according to the relevant type of symmetry) to determine one patterning process parameter (e.g., overlay) at a time.

A non-product target can have one or more advantages. For example, a non-product target design can have reduced or minimized pupil correlations compared to using a measurement of radiation from an on-product target and, as a consequence, a patterning process parameter of interest is easier to determine from the measured radiation. In an embodiment, the non-product target design can reduce or minimize cross-talk between different types of a same patterning process parameter or between different kinds of patterning process parameter. Thus, a cleaner signal can be obtained. The non-product target design can have of advantage of measuring a patterning process parameter for a device pattern that doesn't have instances of a symmetric unit cell for a beam spot. Thus, the non-product target design can enable the extension of the measurement and determination techniques described herein to applications like logic and/or advanced memory where the device pattern may not have instances of a useful symmetric unit cell. A non-product target design can have a relatively simplified structure, which can, e.g., make it easier for modeling as described herein. This can make it easier to separate and determine more than one patterning process parameter type from a single target. Further, a non-product target design can be specially configured to determine just a single patterning process parameter type or determine a specific combination of patterning process parameter types.

But, oversimplification in a non-product target design may kill critical contributors to the patterning process parameter (e.g. overlay). To mitigate this risk, the non-product target design should assume the substantially same process steps as the device product pattern. Further, main contributors to the patterning process parameter of interest should be identified so that they can be factored into the non-product target design and/or and associated modeling.

So, like an on-product target design, an embodiment of a non-product target design is defined in terms of a unit cell comprising structures having a geometric symmetry. In an embodiment, the symmetry can be in a first direction (e.g., X-direction), in a second orthogonal direction (e.g., Y-direction), or both. In an embodiment, the unit cell is created such that a change in physical configuration of the structures in the unit cell causes a break in symmetry, which break in symmetry results in a particular radiation distribution which can be processed to determine a value of a patterning process parameter of interest as described above. Thus, the unit cell effectively as the metrology target and, in an embodiment, contains a minimum area of structures used to provide the signal to determine the patterning process parameter of interest.

In an embodiment, the non-product target design comprises structures created in at least two patterning processes (e.g., at least two executions of a same type of patterning process, at least two executions of different types of patterning processes, etc.). In an embodiment, where the plurality of patterning process executions result in structures in different layers for which a patterning process parameter of interest is being determined, the non-product target design unit cell comprises a structure from each of the plurality of layers of interest. In an embodiment, where the patterning process executions result in structures in a same layer for which a patterning process parameter of interest is being determined, the non-product target design unit cell comprises a structure from each of the applicable different patterning process executions of interest. In an embodiment, a first structure created by a first patterning process and/or a second structure created by a second patterning process is not used to create a functional aspect of a device pattern.

So, in an embodiment and in terms of the unit cell, structures from a plurality of patterning processes together form an instance of the unit cell and the unit cell has geometric symmetry at a nominal physical configuration, wherein the unit cell has a feature that causes, at a different physical configuration than the nominal physical configuration due to, e.g., a relative shift in pattern placement in the first patterning process, the second patterning process and/or another patterning process, an asymmetry in the unit cell. An example of such a feature is one that causes asymmetry in the unit cell in response to an offset of a structure in one layer relative a structure to another layer.

In an embodiment, the non-product target design comprises a repetition of the unit cell. That is in an embodiment, a beam spot on a physical instance of the non-product target would illuminate a plurality of instances of the unit cell filling up the beam spot. In an embodiment, the non-product target design comprises at least 4 instances, at least 8 instances, at least 10 instances, at least 20 instances, at least 40 instances, at least 80 instances, at least 100 instances, at least 200 instances, at least 400 instances, or at least 1000 instances of the unit cell.

In an embodiment, the non-product target as produced on a substrate has a small size. For example, the non-product target can have an area of 100 square microns or less, 50 square microns or less, or 25 square microns or less. In an embodiment, the non-product target has a cross-wise dimension of 10 microns or less or 5 microns or less. In an embodiment, the beam spot for the non-product target has a cross-wise dimension smaller than the maximum cross-wise dimension of the target. In an embodiment, the beam spot for a non-product target has a cross-wise dimension of 10 microns or less, 5 microns or less or 2 microns or less. In an embodiment, the beam spot for a non-product target has a cross-sectional area of less than or equal to 100 square microns, 50 square microns or less, or 25 square microns or less. In an embodiment, the unit cell of a non-product target has an area of 250,000 square nanometers or less, 150,000 square nanometers or less, 100,000 square nanometers or less, or 50,000 square nanometers or less. In an embodiment, the unit cell of a non-product target has a cross-wise dimension of 500 nanometers or less, 300 nanometers or less, 200 nanometers or less or 150 nanometers or less. In an embodiment, the unit cell of the non-product target has a smaller size than a unit cell of a device pattern associated with the non-product target.

In an embodiment, the unit cell comprises a feature (e.g., a structure, a void (e.g., a gap), etc.) that corresponds to a feature (e.g., a structure, a void, etc.) of a device made using a first patterning process and a feature (e.g., a structure, a void, etc.) that corresponds to a feature (e.g., a structure, a void, etc.) of a device made using a second patterning process. For example, a structure of the unit cell is created by a first patterning process that creates a corresponding device feature of a device and another structure of the unit cell is created by a second patterning process that creates a corresponding device feature of the device. In an embodiment, one or more features created in a unit cell share key process steps of a feature in a device for which the unit cell feature is being used to determine a patterning process parameter. In an embodiment, the features of the unit cell created by the respective corresponding patterning processes correspond to, e.g., one or more features (e.g., structures such as lines) of the device that extend or are elongate in a direction essentially parallel to the features (e.g., lines) of the unit cell. So, for example, the unit cell comprises structures extending in a Y-direction can be used to determine overlay of corresponding structures in the device extending in the Y-direction.

In an embodiment, as described further in examples presented below, the unit cell can enable determination of multiple different types of a same patterning process parameter (e.g., overlay). For example, a unit cell enable determination of 2 or more types of overlay, 3 or more types of overlay, etc. For example, besides types of overlay in different directions (e.g., in X and Y), the unit cell can enable determination of overlay between different combinations of features and/or between different combinations of layers.

In an embodiment, the unit cell has features that have comparable dimensions (e.g., widths and/or pitches) to corresponding features of a device. Comparable dimensions means identical or within ±5% from the device feature dimension (i.e., 95% to 105% of the device feature dimension), within ±10% from the device feature dimension, within ±15% from the device feature dimension, within ±20% from the device feature dimension, or within ±25% from the device feature dimension. In an embodiment, the dimensions of one or more the unit cell features can be selected to improve the measurement signal and thus not match the corresponding dimension of a feature of the device pattern. This can be done, for example, by evaluating the sensitivity of signal output to change in dimension of the target feature and so the dimension can be selected in the particular circumstance to maximize signal or provide a signal meeting or crossing a threshold.

In an embodiment, the non-product target can be used in conjunction with an on product target. For example, an overlay can be determined using the non-product target and the result can be fed-forward to determination of the overlay using an on-product target.

Figures 21A, 21B:
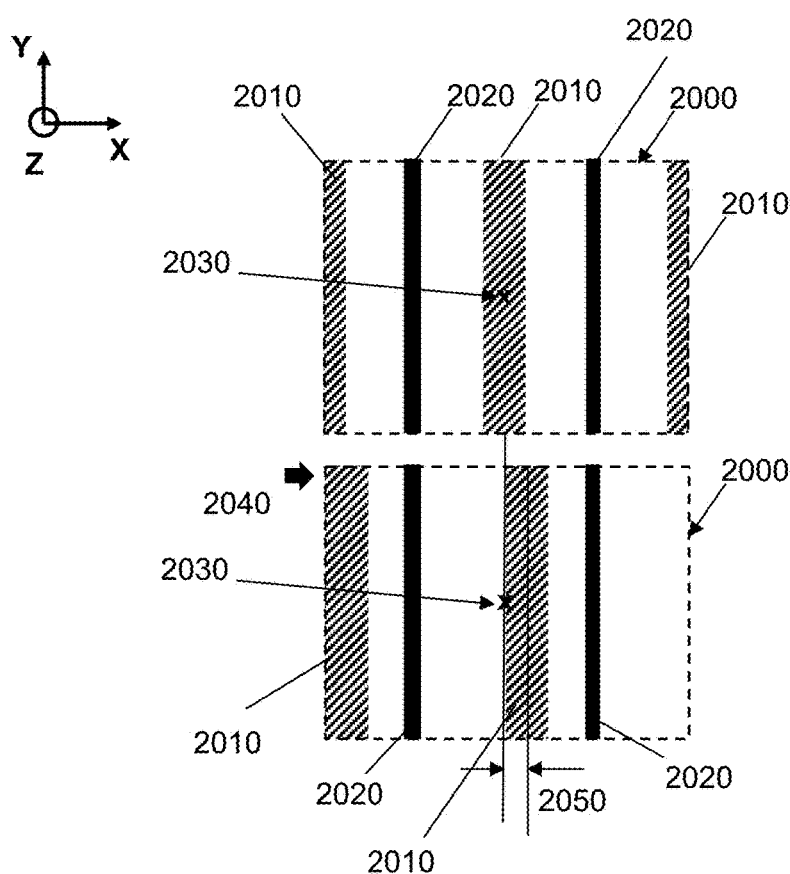
FIG. 21A and FIG. 21B schematically depict an example of a non-product target design.

Referring to FIG. 21, a non-limiting example of a unit cell of a non-product target design is depicted for determining a patterning process parameter using the measuring techniques described herein (e.g., the weights and pupil distributions). In this case, the unit cell is for determining overlay. In FIG. 21A, an example of a unit cell 2000 is depicted. The unit cell 2000 comprises a structure 2010 (in this case, a plurality of lines 2010) created in a first patterning process and a structure 2020 (in this case, a second plurality of lines 2020) created in a second patterning process. An anchor 2030 is depicted to show the symmetry of the unit cell. In this case, the unit cell 2000 has a symmetry in the Y direction. FIG. 21A shows the unit cell in symmetric form, and would correspond to a certain nominal overlay value (e.g., zero overlay).

In an embodiment, the structure 2010 corresponds to a feature of a device made using the first patterning process. That is, the structure 2010 is to be created by a first patterning process that creates a corresponding device feature of a device. For example, the creation of the structure 2010 corresponds to a comparable creation of a structure in a device. Similarly, in an embodiment, the structure 2020 corresponds to a feature of the device made using the second patterning process. That is, the structure 2020 is to be created by a second patterning process that creates a corresponding device feature of the device. For example, the creation of the structure 2020 corresponds to a comparable creation of a structure in the device. So, in an embodiment, the structure 2010 corresponds to, e.g., one or more features (e.g., structures such as lines) of the device that extend in a direction essentially parallel to the features (e.g., lines) of structure 2010. Similarly, the structure 2020 corresponds to, e.g., one or more features (e.g., structures such as lines) of the device that extend in a direction essentially parallel to the features (e.g., lines) of structure 2020. In an embodiment, the structure 2010 is created in a different layer than structure 2020. So, in an embodiment, the structures 2010 and 2020 extending in the Y-direction can be used to determine overlay of corresponding structures in the device extending in the Y-direction.

As noted above, in an embodiment, the structures 2010 and 2020 have comparable widths and/or pitches to features of a device. For example, the structure 2010 has a comparable width and/or pitch to features of a corresponding device structure created in the first patterning process. Similarly, for example, the structure 2020 has a comparable width and/or pitch to features of a corresponding device structure created in the second patterning process.

In unit cell 2000, a feature that will cause a break in symmetry for a different physical configuration of the structures in the unit cell 2000 is a physical difference between the structure 2010 and the structure 2020. In an embodiment, the difference is a difference in width of structures 2010 and 2020 in the X-direction as schematically depicted in FIG. 21A. In an embodiment, the difference is a difference in material composition of structure 2010 and 2020, e.g., structure 2010 is made of a different material than structure 2020. In an embodiment, there can be a combination of physical differences, e.g., difference in width and physical composition.

The result of the physical difference in the case of unit cell 2000 is that a relative shift 2040 in the X-direction in an X-Y plane between structures 2010 and 2020 causes asymmetry in the unit cell 2000. This is depicted in FIG. 21B. In FIG. 21B, structure 2010 shifts from its nominal (e.g., design) position of structure 2010 shown in FIG. 21A when it is created in the second patterning process. The result is a displacement 2050 from the anchor 2030. Thus, assuming that the unit cell 2000 corresponds to a situation of no overlay, the displacement 2050 corresponds to an overlay that is desirably determined by processing the radiation redirected by the target comprising unit cell 2000 as described above (e.g., the weights and pupil distributions).

Since unit cell 2000 shows asymmetry with respect to the Y axis, the translation in the X-direction in combination with the asymmetry causing feature (here the physical difference between structures 2010 and 2020) yields a radiation distribution from which an X-overlay value can be determined. In an embodiment, that X-overlay value would correspond to an X-overlay of features of a device made using the respective patterning processes. Now, of course, the unit cell 2000 can be effectively rotated 90 degrees about the anchor 2030 to give a Y-overlay value for a relative shift in the Y-direction between structure 2010 and 2020. In an embodiment, that Y-overlay value would correspond to a Y-overlay of features of a device made using the respective patterning processes. In an embodiment, in that case, the device features corresponding to structures 2010 and 2020 would extend in the X-direction.

So, in an embodiment, the structures 2010 and 2020 of the unit cell correspond to respective features of a device that extend in a same direction. As a result, the structures of unit cell 2000 can yield a value of overlay in a direction orthogonal to a direction of extension/elongation of features of a device. Thus, by identifying device features extending in a same direction for which an overlay in an orthogonal direction is of interest, the unit cell 2000 can be designed to mimic the overlay by appropriate selection of structures 2010 and 2020 and causing their creation with the creation of the device features.

In FIG. 21, the unit cell 2000 was designed to primarily determine the overlay between the formation of the structures (e.g., lines) themselves. In some patterning processes, a particular pattern is transferred to a substrate having a structure such that, when etching is performed with respect to that pattern, a portion of the structure is removed. This process and its result will be herein referred to as a cut. For example, a device structure (e.g., a line) can be cut into a plurality of pieces and/or an end portion of a device structure can be cut off. As will be appreciated, it can be desirable to know whether a cut has been accurately made. Thus, it can be desirable to know the overlay between cuts and/or the overlay between a cut and a structure.

Furthermore, the unit cell of FIG. 21 enables determining a value of overlay in a direction orthogonal to a direction of extension/elongation of features of a device. But, it can be desirable to determine an overlay in a direction parallel to the direction of extension/elongation of the features of a device.

Referring now to FIG. 22, a non-limiting example of a unit cell of a non-product target design is depicted for determining a patterning process parameter using the measuring techniques described herein (e.g., the weights and pupil distributions). In this case, the unit cell is for determining overlay. In FIG. 22A, an example of a unit cell 2100 is depicted. The unit cell 2100 comprises a structure 2110 (in this case, a plurality of lines 2110) and a structure 2120 (in this case, a second plurality of lines 2120). As will be described in more detail below, in this embodiment, overlay in X and in Y can be determined from this non-product target design.

In the embodiment here, the unit cell 2100 has features of unit cell 2000 of FIG. 21 and thus can enable determination of X direction overlay as described above if structure 2110 is created in a first patterning process and the structure 2120 is created in a second patterning process and there is a physical difference between structure 2110 and 2120. However, if, e.g., X direction overlay is not desired then structures 2110 and 2120 can be created in the same patterning process and/or structures 2110 and 2120 can have the same physical characteristic, i.e., do not have a physical difference. But, even if X direction overlay is not desired, structures 2110 and 2120 can have a different physical characteristic to provide a better measurement signal.

So, in this embodiment that enables determining overlay in X and in Y, the unit cell 2100 comprises a structure 2110 created in a first patterning process and a structure 2120 created in a second patterning process. An anchor 2130 is depicted to show the symmetry of the unit cell. In this case, the unit cell 2100 has a symmetry in the Y direction and a symmetry in the X direction. FIG. 22A shows the unit cell in symmetric form, and would correspond to a certain nominal overlay value (e.g., zero overlay).

In an embodiment, the structure 2110 corresponds to a feature of a device made using the first patterning process as described above and the structure 2120 corresponds to a feature of the device made using the second patterning process. And, in unit cell 2100, a feature that will cause a break in symmetry for a different physical configuration of the structures in the unit cell 2100 is a physical difference between the structure 2110 and the structure 2120. In an embodiment, the difference is a difference in width of structures 2110 and 2120 in the X-direction as schematically depicted in FIG. 22A. In an embodiment, the difference is a difference in material composition of structure 2110 and 2120, e.g., structure 2110 is made of a different material than structure 2120.

As discussed above, the result of the physical difference in the case of unit cell 2100 is that a relative shift 2180 in the X-direction in an X-Y plane between structures 2110 and 2120 causes asymmetry in the unit cell 2100. This is depicted in FIG. 22C. In FIG. 22C, structure 2110 shifts from its nominal (e.g., design) position of structure 2110 shown in FIG. 22A when it is created in the second patterning process. The result is a displacement 2190 from the anchor 2130. Thus, assuming that the unit cell 2100 corresponds to a situation of no overlay, the displacement 2190 corresponds to an overlay that is desirably determined by processing the radiation redirected by the target comprising unit cell 2100 as described above (e.g., the weights and pupil distributions).

Since unit cell 2100 shows asymmetry with respect to the Y axis, the translation in the X-direction in combination with the asymmetry causing feature (here the physical difference between structures 2110 and 2120) yields a radiation distribution from which an X-overlay value can be determined. In an embodiment, that X-overlay value would correspond to an X-overlay of features of a device made using the respective patterning processes. Now, of course, the unit cell 2100 can be effectively rotated 90 degrees about the anchor 2130 to give a Y-overlay value for a relative shift in the Y-direction between structure 2110 and 2120. In an embodiment, that Y-overlay value would correspond to a Y-overlay of features of a device made using the respective patterning processes. In an embodiment, in that case, the device features corresponding to structures 2110 and 2120 would extend in the X-direction.

Now, unit cell 2100 further enables determination of an overlay in the Y direction. Similarly to how the structures in a unit cell of a non-product target can correspond to a feature in a device, a cut in a non-product target design can correspond to a feature (e.g., a cut) in a device.

Referring to FIG. 22A, the unit cell 2100 comprises a cut 2150 created in a first patterning process and a cut 2140 created in a second patterning process. The cuts 2150 and 2140 are arranged so as to maintain symmetry in the unit cell in a nominal physical configuration.

In an embodiment, the cut 2150 corresponds to a feature of a device made using the first patterning process. That is, the cut 2150 is to be created by a first patterning process that creates a corresponding device feature of a device. For example, the creation of the cut 2150 corresponds to a comparable creation of a cut in a device. Similarly, in an embodiment, the cut 2140 corresponds to a feature of the device made using the second patterning process. That is, the cut 2140 is to be created by a second patterning process that creates a corresponding device feature of the device. For example, the creation of the cut 2140 corresponds to a comparable creation of a cut in the device. So, in an embodiment, the cut 2150 corresponds to, e.g., one or more features (e.g., one or more cuts) of the device that extend in a direction essentially parallel to the cut 2150. Similarly, the cut 2140 corresponds to, e.g., one or more features (e.g., one or more cuts) of the device that extend in a direction essentially parallel to the cut 2140. In an embodiment, the cut 2150 is created in a different layer than cut 2140. So, in an embodiment, the cuts 2150 and 2140 can be used to determine overlay of corresponding cuts in the device in the Y-direction.

In an embodiment, the cuts 2150 and 2140 have comparable widths and/or pitches to features of a device. For example, the cut 2150 has a comparable width and/or pitch to features (e.g., one or more cuts) of a corresponding device structure created in the first patterning process. Similarly, for example, the cut 2140 has a comparable width and/or pitch to features (e.g., one or more cuts) of a corresponding device structure created in the second patterning process.

In unit cell 2100, a feature that will cause a break in symmetry for a different physical configuration of the structures in the unit cell 2100 is the arrangement of cuts 2150 and 2140 that will create asymmetry upon relative shift between cuts 2150 and 2140. In an embodiment, the cut 2140 is made in each structure 2120, while cut 2150 is not made in each structure 2110. As will be appreciated, the cut 2150 can be made in each structure 2110, while cut 2140 is not made in each structure 2120. As will be appreciated, many different variations are possible in terms of the cuts including different locations of the cuts and/or different sizes of the cuts.

The result of the arrangement of cuts 2150 and 2140 is that a relative shift 2160 in the Y-direction in an X-Y plane between cuts 2150 and 2140 causes asymmetry in the unit cell 2100. This is depicted in FIG. 22B. In FIG. 22B, cut 2150 shifts from its nominal (e.g., design) position shown in FIG. 22A when it is created in the first patterning process. The result is a displacement 2170 from the anchor 2130. Thus, assuming that the unit cell 2100 corresponds to a situation of no overlay, the displacement 2170 corresponds to an overlay that is desirably determined by processing the radiation redirected by the target comprising unit cell 2100 as described above (e.g., the weights and pupil distributions).

Since unit cell 2100 shows asymmetry with respect to the X axis, the translation in the Y-direction in combination with the asymmetry causing feature (here the arrangement of cuts 2140 and 2150) yields a radiation distribution from which a Y-overlay value can be determined. In an embodiment, that Y-overlay value would correspond to a Y-overlay of features of a device made using the respective patterning processes. Now, of course, the unit cell 2100 can be effectively rotated 90 degrees about the anchor 2130 to give an X-overlay value for a relative shift in the X-direction between cuts 2140 and 2150. In an embodiment, that X-overlay value would correspond to an X-overlay of features (e.g., cuts) of a device made using the respective patterning processes. In an embodiment, in that case, the device features (e.g., cuts) corresponding to cuts 2140 and 2150 would extend in the X-direction.

So, in an embodiment, the cuts 2140 and 2150 of the unit cell correspond to respective features of a device that extend in a same direction. As a result, the structures of unit cell 2100 can yield a value of overlay in a direction parallel to a direction of extension/elongation of features of a device. Thus, by identifying device features extending in a same direction for which an overlay in a parallel direction is of interest, the unit cell 2100 can be designed to mimic the overlay by appropriate selection of cuts 2140 and 2150 and causing their creation with the creation of the device features.

As noted above, in an embodiment, the cuts 2140 and 2150 can be created in the structures 2110 and 2120 in a similar manner as cuts are made in device features. Thus, the cuts 2140 and 2150 can give a good measure of the overlay of cuts made in creating device structures. But, in an embodiment, the cuts 2140 and 2150 may instead be voids created when structure 2110 and 2120 are created and can be created as part of corresponding patterning process to create structures of a device. Thus, voids 2140 and 2150 in this case can give a good measure of the overlay of structures made in creating the device.

And, while FIG. 22 shows cuts/voids facilitating determination of overlay, the structures 2110 and 2120 could have one or more protrusions or deformities, e.g., protrusions at the locations of the depicted cuts. So, relative displacement between such protrusions or deformities could cause asymmetry in the unit cell much like the cuts 2140 and 2150. The protrusions or deformities can be created when the structures 2110 and 2120 are created or created by a cutting process. Thus, the protrusions or deformities can be used to facilitate, e.g., determination of overlay between device structures (e.g., for protrusions or deformities created when the structures 2110 and 2120 are created) or between device cuts (e.g., for protrusions or deformities created by cutting structures 2110 and 2120).

Figure 22D:
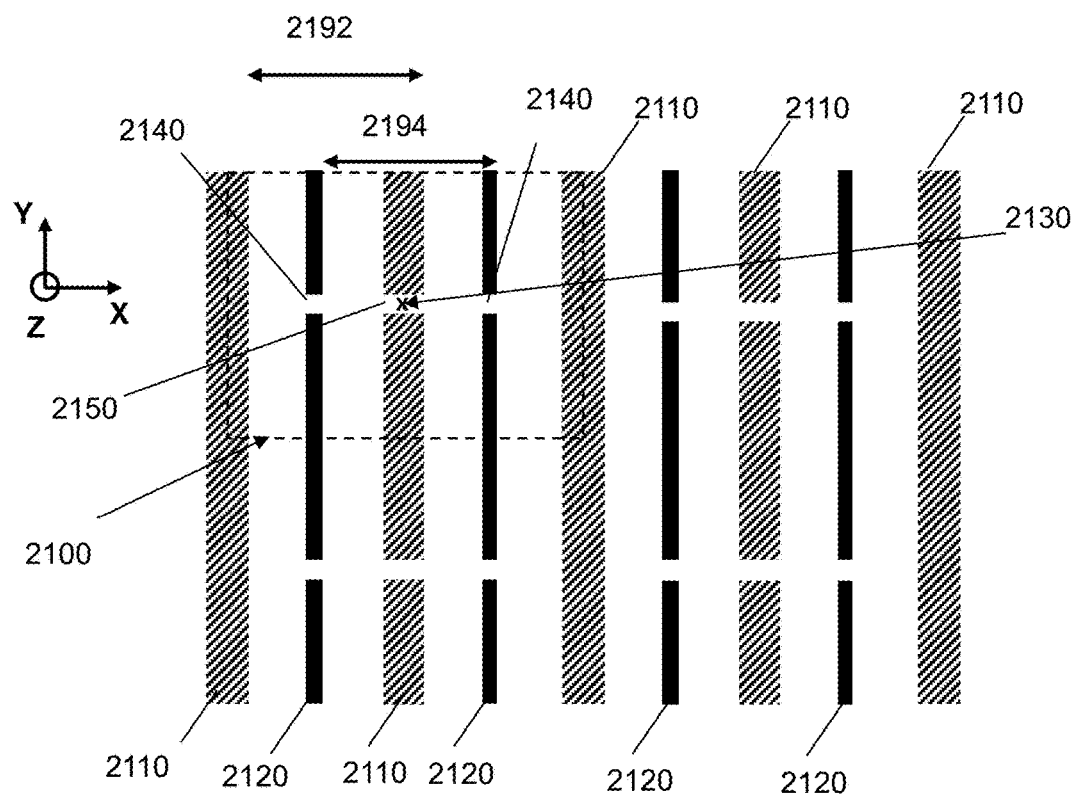

FIG. 22D schematically depicts a non-product target comprising a plurality of instances of the unit cell. In this non-limiting example, FIG. 22D comprises at least 4 instances of the unit cell. FIG. 22D shows the instances of the unit cell in symmetric form, and would correspond to a certain nominal overlay value (e.g., zero overlay). In an embodiment, the pitch 2192 of structures 2110 is comparable to the pitch 2194 of structure 2120.

In FIG. 22D, if, e.g., the second patterning process is not well aligned in the X-direction resulting in a relative shift between structures 2110 and 2120, the Y-symmetry is broken, and so is the Y-symmetry in the pupil. Thus, measurement of the target in that condition can translate into an X-overlay determination. Effectively, the structures 2110 and 2120 are used to determine X-overlay. Similarly, if, e.g., the second patterning process is not well aligned in the Y-direction resulting in a relative shift between cuts 2140 and 2150, the X-symmetry is broken and so is the X-symmetry in the pupil. Thus, measurement of the target in that condition can translate into a Y-overlay determination. Effectively, the cuts 2140 and 2150 are used to determine Y-overlay. Further, as seen in FIG. 22D, a shift of a cut in the Y direction does not change the symmetry with respect to the Y axis and shift of the structures in the X direction does not change the symmetry with respect to the X axis. Thus, the X and Y direction overlays are decoupled. So, while a combination of a badly aligned patterning process in X- and Y-directions results in broken X- and Y-symmetry, the different overlays can be separated from the signal.

In an embodiment, the number of structures and their sizes, pitches, etc. can be configured to closely comparable to the patterning processes of the device pattern. Similarly, the number of cuts (or protrusions/deformities) and their sizes, pitches, etc. can be configured to closely comparable to the patterning processes of the device pattern. For example, cuts will be comparable to the CD and pitch as used in the device when possible. But, in an embodiment, the locations and/or number of cuts are adapted to make a symmetric unit cell. Further, the non-product target overlay sensitivity can be tailored by adapting the pitch of structures and cuts (or protrusions/deformities).

Referring to FIG. 23, a non-limiting example of a unit cell of a non-product target design is depicted for determining a patterning process parameter using the measuring techniques described herein (e.g., the weights and pupil distributions). In this case, the unit cell is for determining overlay. In FIG. 23A, an example of a unit cell 2300 is depicted. The unit cell 2300 comprises a structure 2310 (in this case, a plurality of lines 2310) and a structure 2320 (in this case, a second plurality of lines 2320). Different from FIGS. 21 and 22, structure 2310 extends in a direction substantially perpendicular to structure 2320. An anchor 2340 is depicted to show the symmetry of the unit cell. In this case, the unit cell 2300 has a symmetry in the Y direction. FIG. 23A shows the unit cell in symmetric form, and would correspond to a certain nominal overlay value (e.g., zero overlay).

So, in this embodiment of unit cell 2300, an overlay in the X-direction between a structure extending a first direction and a cut or a structure extending a second direction essentially orthogonal to the first direction can be determined from the redirected radiation from this unit cell.

In particular, similar to the principles described above, the unit cell 2300 comprises a structure 2310 created in a first patterning process and comprise a cut 2330 and/or a structure 2320 created in a second patterning process. Where, for example, the overlay between the structure 2310 and the cut 2330 is desired then the structure 2310 is created in the first patterning process and the cut 2330 is made in the second patterning process (optionally, the structure 2320 is also created in the second patterning process). Where, for example, the overlay between the structures 2310 and 2320 is desired then the structure 2310 is created in the first patterning process and the structure 2320 is created in the second patterning process with a void comparable to, e.g., cut 2330. The structures 2310 and 2320 and the cut 2330 are arranged so as to maintain symmetry in the unit cell in a nominal physical configuration.

Similar to embodiments described above, the structure 2310 corresponds to a feature of a device made using the first patterning process. That is, the structure 2310 is to be created by a first patterning process that creates a corresponding device feature of a device. For example, the creation of the structure 2310 corresponds to a comparable creation of a structure in a device. Similarly, in an embodiment, the structure 2320 and/or cut 2330 corresponds to a feature of the device made using the second patterning process. That is, the structure 2320 and/or cut 2330 are to be created by a second patterning process that creates a corresponding device feature of the device. For example, the creation of the cut 2330 corresponds to a comparable creation of a cut in the device. So, in an embodiment, the structure 2310 corresponds to, e.g., one or more features (e.g., one or more structures) of the device that extend in a first direction essentially parallel to the structure 2310. Similarly, the structure 2320 and/or cut 2330 correspond to, e.g., one or more features of the device that extend in a second direction essentially perpendicular to the first direction. In an embodiment, the structure 2320 and/or cut 2330 is created in a different layer than structure 2310. So, in an embodiment, the cut 2330 (or a void comparable to the cut of structure 2320) can be used to determine overlay of corresponding features in the device in the X-direction.

In an embodiment, the structure 2310 and the structure 2320 and/or cut 2330 have comparable widths and/or pitches to features of a device. For example, the structure 2310 has a comparable width and/or pitch to features (e.g., one or more structures) of a corresponding device structure created in the first patterning process. Similarly, for example, the structure 2320 and/or cut 2330 have a comparable width and/or pitch to features of a corresponding device structure created in the second patterning process.

In unit cell 2300, a feature that will cause a break in symmetry for a different physical configuration of the structures in the unit cell 2300 is the arrangement of cut 2330 (or the comparable void in a structure 2320) that will create asymmetry upon a relative shift between the structure 2310 and the cut 2330 (or between structure 2310 and 2320). As will be appreciated, many different variations are possible in terms of the cuts/voids including different locations of the cuts/voids and/or different sizes of the cuts/voids.

The result of the arrangement of cut 2330 (or void 2330) in combination with the essentially perpendicular structures 2310 and 2320 is that a relative shift 2350 in the X-direction in an X-Y plane between structure 2310 and cut 2330 (or between structures 2310 and 2320 where there is a void) causes asymmetry in the unit cell 2300. This is depicted in FIG. 23B. In FIG. 23B, cut 2330 shifts from its nominal (e.g., design) position shown in FIG. 23A when it is created in the second patterning process. The result is a displacement 2360 from the anchor 2340. Thus, assuming that the unit cell 2300 corresponds to a situation of no overlay, the displacement 2360 corresponds to an overlay that is desirably determined by processing the radiation redirected by the target comprising unit cell 2300 as described above (e.g., the weights and pupil distributions).

Since unit cell 2300 shows asymmetry with respect to the Y axis, the translation in the X-direction in combination with the asymmetry causing feature (here the arrangement of cut 2330 (or void 2330) in combination with the essentially perpendicular structures 2310 and 2320) yields a radiation distribution from which a X-overlay value can be determined. In an embodiment, that X-overlay value would correspond to an X-overlay of features of a device made using the respective patterning processes.

So, in an embodiment, the structure 2310 and the structure 2320 and/or cut 2330 of the unit cell correspond to respective features of a device that extend in a same direction. As a result, the structures of unit cell 2300 can yield a value of overlay for features that extend or are elongate in perpendicular directions. Thus, by identifying device features extending in orthogonal direction for which an overlay in a certain direction is of interest, the unit cell 2300 can be designed to mimic the overlay by appropriate selection of the cut 2330 (or void 2330) in relation to orthogonal structures 2310 and 2320 and causing their creation with the creation of the device features.

And, while FIG. 23 shows cuts/voids facilitating determination of overlay, the structures 2310 and 2320 could have one or more protrusions or deformities, e.g., protrusions at the locations of the depicted cuts. So, relative displacement between such protrusions or deformities could cause asymmetry in the unit cell much like the cut 2330. The protrusions or deformities can be created when the structures 2310 and 2320 are created or created by a cutting process. Thus, the protrusions or deformities can be used to facilitate, e.g., determination of overlay between device structures (e.g., for protrusions or deformities created when the structures 2310 and 2320 are created) or between a cut and a structure.

Now, of course, the unit cell 2300 can be effectively rotated 90 degrees about the anchor 2340 to give a Y-overlay value for a relative shift in the Y-direction between the structure 2310 and the structure 2320 and/or cut 2330. In an embodiment, that Y-overlay value would correspond to a Y-overlay of features of a device made using the respective patterning processes.

Referring to FIG. 24, a non-limiting example of a unit cell of a non-product target design is depicted for determining a patterning process parameter using the measuring techniques described herein (e.g., the weights and pupil distributions). In this case, the unit cell is for determining overlay. In FIG. 24A, an example of a unit cell 2400 is depicted. The unit cell 2400 comprises a structure 2410 (in this case, a plurality of lines 2410) and a structure 2420 (in this case, a second plurality of lines 2420). Structure 2410 extends in a direction substantially perpendicular to structure 2420. An anchor 2440 is depicted to show the symmetry of the unit cell. In this case, the unit cell 2400 has a symmetry in the X direction. FIG. 24A shows the unit cell in symmetric form, and would correspond to a certain nominal overlay value (e.g., zero overlay).

So, in this embodiment of unit cell 2400, an overlay in the Y-direction between a structure extending a first direction and a cut or a structure extending a second direction essentially orthogonal to the first direction can be determined from the redirected radiation from this unit cell.

FIG. 24 is effectively a reverse arrangement of FIG. 23. While FIG. 23 is designed for determining X direction overlay. FIG. 24 is designed to determine Y direction overlay; however, like FIG. 23, the FIG. 24 unit cell can be rotated 90 degrees to determine X direction overlay. But, differently than FIG. 23, a cut 2430 (or a void 2430 of created structure 2410) is created in the first patterning process compared to the second patterning process in the embodiment of FIG. 24.

So, in unit cell 2400, a feature that will cause a break in symmetry for a different physical configuration of the structures in the unit cell 2400 is the arrangement of cut 2430 (or the comparable void in a structure 2410) that will create asymmetry upon a relative shift between the cut 2430 and the structure 2420 (or between structures 2410 and 2420). As will be appreciated, many different variations are possible in terms of the cuts/voids including different locations of the cuts/voids and/or different sizes of the cuts/voids.

The result of the arrangement of cut 2430 (or void 2430) in combination with the essentially perpendicular structures 2410 and 2420 is that a relative shift 2450 in the Y-direction in an X-Y plane between the cut 2430 and the structure 2420 (or between structures 2410 and 2420 where there is a void) causes asymmetry in the unit cell 2400. This is depicted in FIG. 24B. In FIG. 24B, cut 2430 shifts from its nominal (e.g., design) position shown in FIG. 24A when it is created in the first patterning process. The result is a displacement 2460 from the anchor 2440. Thus, assuming that the unit cell 2300 corresponds to a situation of no overlay, the displacement 2460 corresponds to an overlay that is desirably determined by processing the radiation redirected by the target comprising unit cell 2400 as described above (e.g., the weights and pupil distributions).

Since unit cell 2400 shows asymmetry with respect to the X axis, the translation in the Y-direction in combination with the asymmetry causing feature (here the arrangement of cut 2430 (or void 2430) in combination with the essentially perpendicular structures 2410 and 2420) yields a radiation distribution from which a Y-overlay value can be determined. In an embodiment, that Y-overlay value would correspond to a Y-overlay of features of a device made using the respective patterning processes.

And, while FIG. 24 shows cuts/voids facilitating determination of overlay, the structures 2410 and 2420 could have one or more protrusions or deformities, e.g., protrusions at the locations of the depicted cuts. So, relative displacement between such protrusions or deformities could cause asymmetry in the unit cell much like the cut 2430. The protrusions or deformities can be created when the structures 2410 and 2420 are created or created by a cutting process. Thus, the protrusions or deformities can be used to facilitate, e.g., determination of overlay between device structures (e.g., for protrusions or deformities created when the structures 2410 and 2420 are created) or between a cut and a structure.

Now, of course, the unit cell 2400 can be effectively rotated 90 degrees about the anchor 2440 to give an X-overlay value for a relative shift in the X-direction between the structure 2410 and/or cut 2430 and the structure 2420. In an embodiment, that X-overlay value would correspond to an X-overlay of features of a device made using the respective patterning processes.

Referring to FIG. 25, a non-limiting example of a unit cell of a non-product target design is depicted for determining a patterning process parameter using the measuring techniques described herein (e.g., the weights and pupil distributions). In this case, the unit cell is for determining overlay. In FIG. 25A, an example of a unit cell 2500 is depicted. The unit cell 2500 comprises a structure 2510 (in this case, a plurality of lines 2510) created in a first patterning process and a structure 2520 (in this case, a second plurality of lines 2520) created in a second patterning process. Structure 2510 extends in a direction substantially parallel to structure 2520. An anchor 2530 is depicted to show the symmetry of the unit cell. In this case, the unit cell 2500 has a symmetry in the Y direction. FIG. 25A shows the unit cell in symmetric form, and would correspond to a certain nominal overlay value (e.g., zero overlay).

The non-product target design of FIG. 25 is comparable to the non-product target design of FIG. 21. The difference is that a center line 2510 is not provided compared to a center line 2010 provided in FIG. 20. This means the unit cell 2500 and the non-product target involves fewer structures than FIG. 20, which can, e.g., improve the related modeling. However, this may involve a different pitch in the lines from corresponding features in the device, e.g., the pitch for the lines of structure 2520 may need to be different than a pitch of comparable lines in the device.

In an embodiment, structure 2510 comprises at least two sub-structures (e.g., line-like structures). Alternatively or additionally, structure 2520 comprises at least two sub-structures (e.g., line-like structures). This is to enable a sufficient signal. This principle can apply to other embodiments described herein.

Like FIG. 21, a feature that causes a break of symmetry is a physical difference between structures 2510 and 2520, which in the depicted embodiment is a difference in width of the structures 2510 and 2520. And so, like FIG. 21 and as shown in FIG. 25B, a relative shift 2540 between the structures 2510 and 2520 results in a break of symmetry in the Y-direction. The break of symmetry results in a particular radiation distribution that enables determination of the relative displacement 2550. The relative displacement 2550 can correspond to an X direction overlay of corresponding device features.

Referring to FIG. 26, a non-limiting example of a unit cell of a non-product target design is depicted for determining a patterning process parameter using the measuring techniques described herein (e.g., the weights and pupil distributions). In this case, the unit cell is for determining overlay. In FIG. 26A, an example of a unit cell 2600 is depicted. The unit cell 2600 comprises a structure 2610 (in this case, a plurality of lines 2610) created in a first patterning process and a structure 2620 (in this case, a second plurality of lines 2620) created in a second patterning process. Structure 2610 extends in a direction substantially parallel to structure 2620. Further, structure 2610 comprises a cut 2630 created by a patterning process and structure 2620 comprises a cut 2640 created by a patterning process. An anchor 2650 is depicted to show the symmetry of the unit cell. In this case, the unit cell 2600 has a symmetry in the Y direction and a symmetry in the X direction. FIG. 26A shows the unit cell in symmetric form, and would correspond to a certain nominal overlay value (e.g., zero overlay).

The non-product target design of FIG. 26 is comparable to the non-product target design of FIG. 22 in layout and in terms of being capable of being used to determine overlay in X and Y directions. A difference is that a center line 2610 is not provided compared to a center line 2010 provided in FIG. 20. This means the unit cell 2600 and the non-product target involves fewer structures than FIG. 20, which can, e.g., improve the related modeling. Further, the cuts 2630 and 2640 have a different arrangement than in FIG. 22. The arrangement of cuts is to provide asymmetry but then also enable a break of symmetry when there is a relative shift involving the cuts.

As a result of this different arrangement of FIG. 26, the design may involve a different pitch in the lines from corresponding features in the device, e.g., the pitch for the lines of structure 2620 may need to be different than a pitch of comparable lines in the device.

Like FIG. 22, a feature that causes a break of symmetry is a physical difference between structures 2610 and 2620, which in the depicted embodiment is a difference in width of the structures 2610 and 2620. And so, like FIG. 22 and as shown in FIG. 26C, a relative shift 2670 between the structures 2610 and 2620 results in a break of symmetry in the Y-direction. The break of symmetry results in a particular radiation distribution that enables determination of the relative displacement 2680. The relative displacement 2680 can correspond to an X direction overlay of corresponding device features.

Further, like FIG. 22, a feature that causes a break of symmetry is the arrangement of cuts 2630 and 2640. And so, like FIG. 22 and as shown in FIG. 26B, a relative shift 2650 between the cuts 2630 and 2640 results in a break of symmetry in the X-direction. The break of symmetry results in a particular radiation distribution that enables determination of the relative displacement 2660. The relative displacement 2660 can correspond to a Y direction overlay of corresponding device features.

Referring to FIG. 27, a non-limiting example of a unit cell of a non-product target design is depicted for determining a patterning process parameter using the measuring techniques described herein (e.g., the weights and pupil distributions). In this case, the unit cell is for determining overlay. In FIG. 27A, an example of a unit cell 2700 is depicted. The unit cell 2700 comprises a structure 2710 (in this case, a plurality of lines 2710) created in a first patterning process, a structure 2720 (in this case, a second plurality of lines 2720) created in a second patterning process, and a structure 2730 (in this case, a third plurality of lines 2730) created in a third patterning process. Structure 2710 extends in a direction substantially parallel to structure 2720. Further, structure 2730 extends in a direction substantially perpendicular to structures 2710 and 2720. Further, structure 2710 comprises a cut 2740 created by a patterning process and a cut 2750 created by a patterning process. An anchor 2750 is depicted to show the symmetry of the unit cell. In this case, the unit cell 2700 has a symmetry in the Y direction and a symmetry in the X direction. FIG. 27A shows the unit cell in symmetric form, and would correspond to a certain nominal overlay value (e.g., zero overlay).

The non-product target design of FIG. 27 is comparable to the non-product target design of FIG. 22 in layout and in terms of being capable of being used to determine overlay in X and Y directions. A difference is that a further structure 2730 is provided in a third patterning process.

Due this arrangement, this non-product target can enable, for example, determining overlay between features across more than 2 layers of the device; for example, this non-product target can enable determining an overlay between a feature in a first layer of the device and a feature in a second layer of the device and an overlay between the feature in the first layer of the device and a feature in a third layer of the device.

For example, as described with respect to FIG. 22, a shift between structures 2710 and 2720 in the X direction can enable determination of an X direction overlay between device features corresponding to structures 2710 and 2720.

But, in addition to the arrangement of FIG. 22, a shift between cut 2750 and structure 2730 in the Y direction can enable determination of a Y direction overlay between device features corresponding to cut 2750 and structure 2730. And, in this embodiment, structure 2730 can be in a different layer than structure 2710 and 2720.

A feature that causes a break of symmetry in respect of structure 2730 is the arrangement of cut 2750 in relation to structure 2730. And so, as shown in FIG. 27B, a relative shift 2760 between the structure 2730 and cut 2750 results in a break of symmetry in the X-direction. The break of symmetry results in a particular radiation distribution that enables determination of the relative displacement 2770. The relative displacement 2670 can correspond to a Y direction overlay of corresponding device features.

Thus, FIG. 27 represents a combined target that enables measurement of overlay between 3 different process steps. The target enables, for example, a $1^{st}$ layer feature to $2^{nd}$ layer feature overlay measurement (in the X direction) and $1^{st}$ layer feature to $3^{rd}$ layer feature overlay measurement (in the Y-direction). Of course, in an embodiment, the target of FIG. 27 can be separated into discrete targets (e.g., a target having structures 2710 and 2720 and cut 2740 for a $1^{st}$ layer feature to $2^{nd}$ layer feature overlay measurement and another target having structures 2710 and 2730 and cut 2740 for a $1^{st}$ layer feature to $3^{rd}$ layer feature overlay measurement) to provide one target per layer pair rather than a combined target as shown in FIG. 27.

Referring to FIG. 28, a non-limiting example of a unit cell of a non-product target design is depicted for determining a patterning process parameter using the measuring techniques described herein (e.g., the weights and pupil distributions). In this case, the unit cell is for determining overlay. In FIG. 28A, an example of a unit cell 2800 is depicted. The unit cell 2800 comprises a structure 2810 (in this case, a plurality of closed curves 2810, e.g., essentially circles or ovals) created in a first patterning process and a structure 2820 (in this case, a second plurality of closed curves 2820, e.g., essentially circles or ovals) created in a second patterning process. Structure 2810 extends in a direction substantially parallel to structure 2820. In this case, the unit cell 2800 has a symmetry in the Y direction and a symmetry in the X direction. FIG. 28A shows the unit cell in symmetric form, and would correspond to a certain nominal overlay value (e.g., zero overlay).

In this arrangement, as shown in FIG. 28B, a relative shift 2830 between the structures 2810 and 2820 results in a break of symmetry in the Y-direction. The break of symmetry results in a particular radiation distribution that enables determination of the relative displacement 2840. The relative displacement 2840 can correspond to an X direction overlay of corresponding device features.

Further, in this arrangement, as shown in FIG. 28C, a relative shift 2850 between the structures 2810 and 2820 results in a break of symmetry in the X-direction. The break of symmetry results in a particular radiation distribution that enables determination of the relative displacement 2860. The relative displacement 2860 can correspond to a Y direction overlay of corresponding device features.

A feature that causes a break of symmetry is the staggered arrangement of structure 2810 with respect to structure 2820. While, in this embodiment, structures 2810 are depicted as having a different width than structures 2820, it need not have such a difference where the structures 2810 and 2820 are in a staggered arrangement as shown. Otherwise, if the structures 2810 and 2820 are not in a staggered arrangement, a physical difference (e.g., different width, different material, etc.) could be used to break symmetry.

Different combinations of features from FIGS. 21-28 can be combined into a unit cell to enable determination of multiple types of a parameter (e.g., X direction overlay and Y direction overlay, overlay between different combinations of features of a device, etc.). In an embodiment, separate targets can be created each for a single type of parameter (e.g., a target for X direction overlay and a separate target for Y direction overlay, a target for overlay between a first combination of features and a separate target for overlay between a second combination of features, etc.) or multiples targets can be created to determine combinations of types of parameter.

Figure 29A:
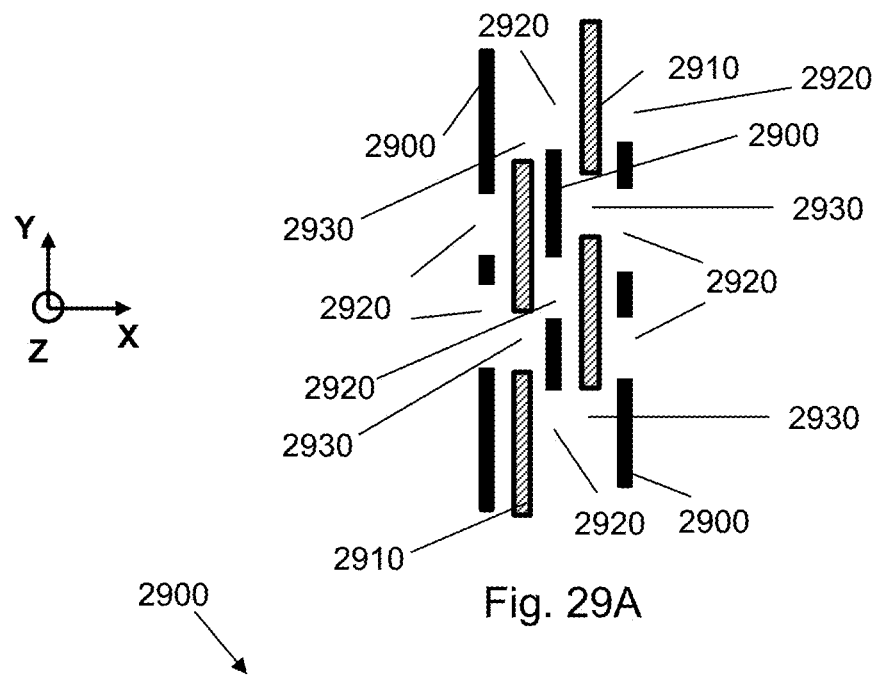
FIG. 29A schematically depicts an example of device pattern features.

Referring now to FIG. 29, FIG. 29A schematically depicts an example of device pattern features. For example, the device pattern features could be for a memory device (e.g. a SRAM). As will be appreciated, a full memory device would likely have many more features in the area depicted. However, it may be desired to determine overlay of a certain combination of the device pattern features depicted in FIG. 29A. Such overlay can be used for patterning process control, defect prediction in the patterning process, etc. as discussed in more detail herein.

In FIG. 29A, the device pattern comprises a plurality of line features 2900 extending substantially parallel to each other. Further, the device pattern comprises a plurality of line features 2910 extending substantially parallel to each other and which interleave with the line features 2900. In an example embodiment of a multi-patterning process as described further hereafter, the features 2900 are created first and then features 2910 are created thereafter because of, e.g., resolution limits.

Further, it is desired to have, e.g., multiple segments along a line feature 2900. So, in a multi-patterning process, such segments can be created by cuts as described above. So, the device pattern comprises a plurality of cut features 2920 with respect to line features 2900. Further, the device pattern comprises a plurality of cut features 2930 with respect to line feature 2910.

Figure 29B:
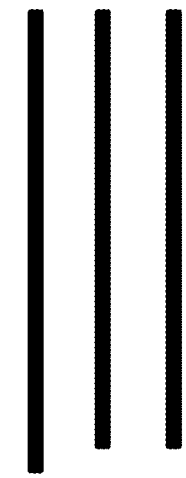
FIG. 29B, FIG. 29C, FIG. 29D and FIG. 29E schematically depict an example of steps of a device patterning process.
Figure 29C:
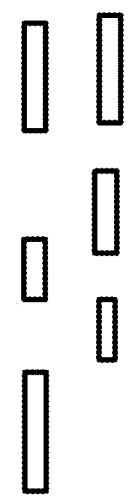

The device pattern features can then be created by a plurality of litho-etch (LE) processes. FIG. 29B, FIG. 29C, FIG. 29D and FIG. 29E schematically depict an example of steps of a device multi-patterning method. In FIG. 29B, the plurality of line features 2900 is created. Then, in FIG. 29C, cuts 2920 are applied to features 2900 to yield the segmented line features 2900 as shown in FIG. 29A.

Figure 29D:
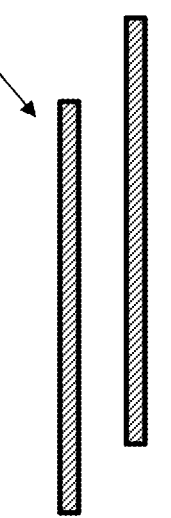
Figure 29E:

In FIG. 29D, the plurality of line features 2910 is created, wherein the plurality of line features 2910 are created in an interleaved fashion between line features 2900. Then, in FIG. 29E, cuts 2930 are applied to features 2910 to yield the segmented line features 2910 as shown in FIG. 29A.

Thus, it may be desired to determine an overlay between the creation of cuts 2920 and cuts 2930. Or, it may be desired to determine an overlay between structures 2900 and 2910. So, as will be appreciated, there can be a variety of different overlays that could desirably be determined and then monitored, controlled, etc.

So, the layers of interest are identified and the overlay (e.g., overlay in the X-direction, overlay in the Y direction, or both overlay in the X and Y directions) that should be determined is identified. In this example, it may be desired to determine the X direction overlay between structures 2900 and 2910 and determine the Y direction overlay between the cuts 2920 and 2930.

So, having the one or more particular overlays of interest within the device, a non-product target can be designed to help determine that overlay. In the case of the device features of FIG. 29A, a line space pattern of structures can be created with a comparable pitch and CD as the layers of interest. An example of such structures of a non-product target design is schematically depicted in FIG. 29F. In this case, for example, structure 2940 would be created in a same patterning process as structure 2900 is created and structure 2950 would be created in a same patterning process as structure 2910. As discussed above with respect to FIGS. 21-28, a physical difference can be provided between structures 2940 and 2950 to enable a relative shift in the X direction when structures 2940 and 2950 are created to cause a break in symmetry to enable X direction overlay determination. Since structures 2940 and 2950 act effectively as proxies for structures 2900 and 2910, the determination of the relative displacement between structures 2940 and 2950 in the X direction from the radiation redirected by the non-product target in that condition can correspond to a X direction overlay for structures 2900 and 2910.

Further, referring to FIG. 29G, one or more cuts are introduced to the structures of FIG. 29F in the non-product target design to enable determination of Y direction overlay. To enable this, a unit cell 2960 is defined. As seen the unit cell has the structures 2940 and 2950 and has Y symmetry that is broken by the relative displacement of the structures 2940 and 2950 in the X direction. So, to enable the Y direction overlay determination, a feature is introduced to create asymmetry in the X direction when there is a relative displacement in the Y direction. As noted above, it is desired to determine the overlay in the Y direction between cuts 2920 and 2930. So, comparable cuts are introduced to structures 2940 and 2950 respectively since cuts 2920 and 2930 remove portions of structures 2900 and 2910 respectively. In this embodiment, those cuts are cuts 2970 and 2980. The cuts 2970 and 2980 create a reference to determine Y direction overlay due to a relative shift between the cuts 2970 and 2980 during their creation. Cuts 2970 and 2980 act effectively as proxies for cuts 2920 and 2930, and so the determination of the relative displacement between cuts 2970 and 2980 in the Y direction from the radiation redirected by the non-product target in that condition can correspond to a Y direction overlay for cuts 2920 and 2930.

In an embodiment, the cuts 2970 and 2980 are such that the unit cell is symmetric in the X direction at a nominal configuration. Further, in an embodiment, the cuts are such that they do not affect the symmetry of the unit cell in respect of the X overlay determination as described above. In an embodiment, the cuts 2970 and 2980 have comparable CD and pitch to the cuts in the device patterning process when possible. However, the size, number and location of the cuts may be adapted to make a symmetric unit cell. In an embodiment, as shown in FIG. 29G, the unit cell is repeated as a plurality of instances to form a non-product target for creation on a substrate.

So, in this embodiment, at a nominal configuration, the unit cell 2960 has both X and Y symmetry. Further, a relative shift in the Y direction between features results in a break in X symmetry in the unit cell (while Y symmetry is preserved) so that Y direction overlay can be determined. Also, a relative shift in the X direction between features results in a break in Y symmetry in the unit cell (while X symmetry is preserved) so that X direction overlay can be determined.

Figure 30A:
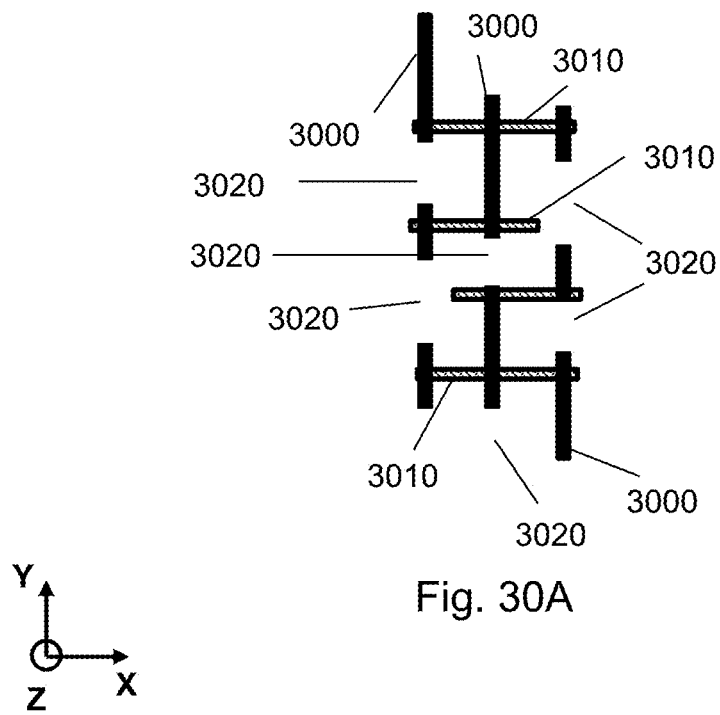
FIG. 30A schematically depicts an example of device pattern features.

Referring now to FIG. 30, FIG. 30A schematically depicts a further example of device pattern features. For example, the device pattern features could be for a memory device (e.g. a SRAM). As will be appreciated, a full memory device would likely have many more features in the area depicted. However, it may be desired to determine overlay of a certain combination of the device pattern features depicted in FIG. 30A Such overlay can be used for patterning process control, defect prediction in the patterning process, etc. as discussed in more detail herein.

In FIG. 30A, the device pattern comprises a plurality of line features 3000 extending substantially parallel to each other. Further, the device pattern comprises a plurality of line features 3010 extending substantially parallel to each other and essentially perpendicular to the line features 3000. In an example embodiment of a multi-patterning process as described further hereafter, the features 3010 are created first and then features 3000 are created thereafter.

Further, it is desired to have, e.g., multiple segments along a line feature 3000. So, in a multi-patterning process, such segments can be created by cuts as described above. So, the device pattern comprises a plurality of cut features 3020 with respect to line features 3000. The device pattern features can then be created by a plurality of litho-etch (LE) processes different than, but similar to, those described in respect of FIGS. 29B-29E.

Thus, it may be desired to determine an overlay between structures 3000 and 3010. Or it may be desired to determine an overlay between the creation of cuts 3020 and structure 3010. So, as will be appreciated, there can be a variety of different overlays that could desirably be determined and then monitored, controlled, etc.

So, the layers of interest are identified and the overlay (e.g., overlay in the X-direction, overlay in the Y direction, or both overlay in the X and Y directions) that should be determined are identified. In this example, it may be desired to determine the Y direction overlay between structure 3010 and cut 3020.

Figures 30B, 30C:
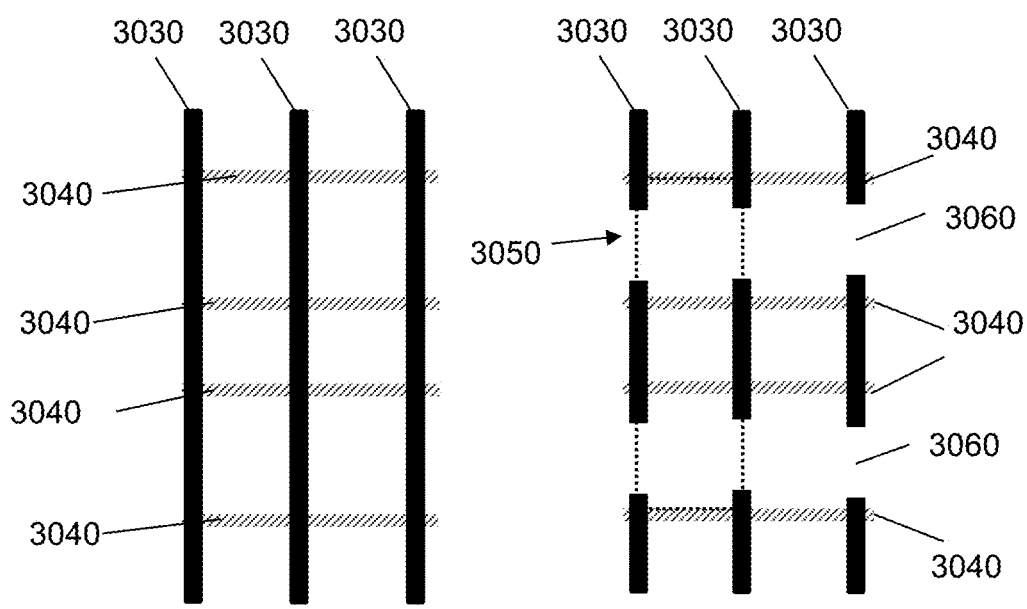
FIG. 30B schematically depicts an example of structures of a non-product target design.
FIG. 30C schematically depicts an example of a non-product target design created from the structures of FIG. 30B.

So, having the one or more particular overlays of interest within the device, a non-product target can be designed to help determine that overlay. In the case of the device features of FIG. 30A, a line space pattern of structures can be created with a comparable pitch and CD as the layers of interest. An example of such structures of a non-product target design is schematically depicted in FIG. 30C. In this case, for example, structure 3040 would be created in a same patterning process as structure 3010 is created and structure 3030 would be created in a same patterning process as structure 3000. As discussed above with respect to FIG. 24, a cut can be provided to determine Y direction overlay between a cut and an essentially perpendicular structure. That is, a cut can enable a relative shift in the Y direction between a cut and a structure, when they are created, cause a break in symmetry to enable Y direction overlay determination.

So, referring to FIG. 30C, one or more cuts are introduced to the structures of FIG. 30B in the non-product target design to enable determination of Y direction overlay. To enable this, a unit cell 3050 is defined. As seen the unit cell has the structures 3030 and 3040. Further, the unit cell has a cut 3060 in structure 3030. The cut is such that the X symmetry is broken by the relative displacement between the creation of the cut 3060 and the structure 3040 in the Y direction. The cut 3060 thus enables creation of asymmetry in the X direction when there is a relative displacement in the Y direction between cut 3060 and the structure 3040. The cut 3060 creates a reference to determine Y direction overlay due to a relative shift between cut 3060 and the structure 3040 during their creation. Since the cut 3060 and structure 3040 acts a proxy for structure 3010 and cut 3020, the determination of the relative displacement between cut 3060 and the structure 3040 in the Y direction from the radiation redirected by the non-product target in the relative displacement condition can correspond to a Y direction overlay between structure 3010 and cut 3020.

In an embodiment, the cut 3060 is such that the unit cell is symmetric in the X direction at a nominal configuration. Further, in an embodiment, the cut 3060 is such that it does not affect the symmetry of the unit cell in the Y direction. In an embodiment, the cut 3060 has comparable CD and pitch to cut 3020 in the device patterning process when possible. However, the size, number and location of the cut may be adapted to make a symmetric unit cell. In an embodiment, as shown in FIG. 30C, the unit cell is repeated as a plurality of instances to form a non-product target for creation on a substrate.

So, in this embodiment, at a nominal configuration, the unit cell 3060 has both X and Y symmetry. Further, a relative shift in the Y direction between features results in a break in X symmetry in the unit cell (while Y symmetry is preserved) so that Y direction overlay can be determined.

Figure 31:
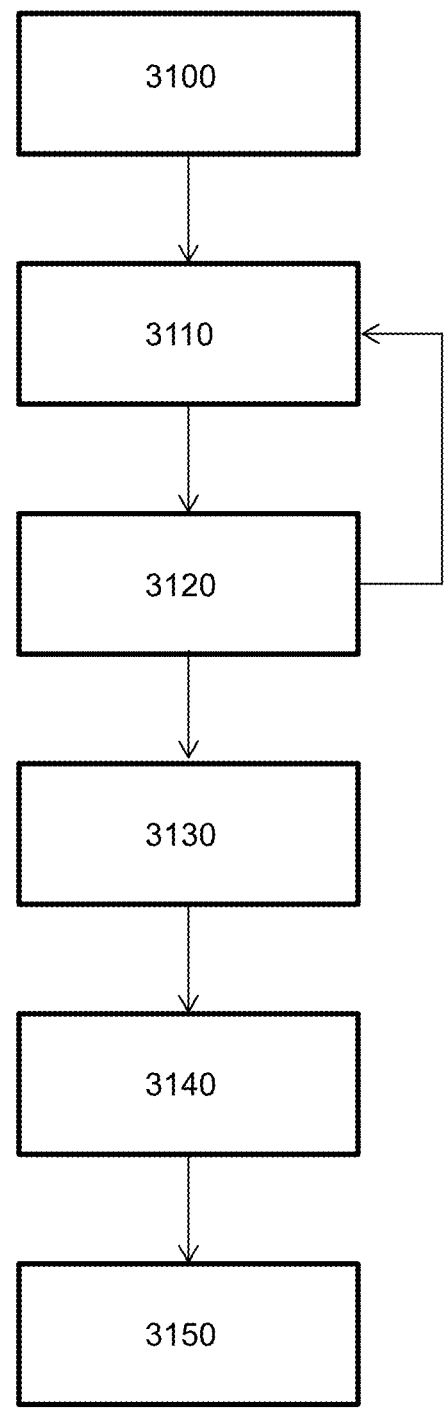
FIG. 31 corresponds to an embodiment of a method of designing a non-product target design.

Referring to FIG. 31, an embodiment of a method to design a non-product target is schematically depicted. While several steps are described, not all of the steps are required. Thus, in an embodiment, a sub-combination of the steps can be selected. Further, the order of the steps (or a sub-combination of steps) could be re-arranged. Further, the design method is described in terms of creating a non-product target design for determining overlay (or any other parameter derived from the results of such a target). However, the method can be extended to one or more other parameters.

At 3100, one or more non-product targets are designed in a non-product target layout design process. The one or more non-product target designs can be any one or more of those described herein. In an embodiment, one or more techniques of designing the non-product target design as described herein can be used. In an embodiment, the non-product target layout design process primarily determines the geometry of the unit cell of the non-product target (and thus the geometry of the non-product target).

In an embodiment, the non-product target layout design process involves evaluating a device pattern to identify an overlay of interest. Often there are multiple combinations of features and/or layers, especially with LELE processing, for evaluation of overlay. So, it may be desirable to determine one or more overlay-critical combinations of features and/or layers.

With one or more overlays identified in terms of the features/layers being evaluated and the one or more directions (e.g., X, Y or X and Y), a repetitive pattern can be created (e.g., a line space pattern, an array of closed curves such as in FIG. 28). In an embodiment, the repetitive pattern has a comparable pitch and/or CD as the features/layers of interest from the device pattern.

Then, depending on the device pattern and overlay to measure, the geometry of a unit cell of the non-product target design can be created using one or more of the techniques described herein. For example, where features of interest are parallel (e.g. Y direction) and overlay in the X direction is desired, then a target such as in FIG. 21 can be created or a target can incorporate design features from FIG. 21 to enable such overlay to be determined. Where, for example, features of interest are parallel (e.g. Y direction) and overlay in the Y direction is desired, then a target incorporating the cut/protrusion arrangement in FIG. 22 can be created or a target can incorporate design features from FIG. 22 to enable such overlay to be determined. Where, for example, features of interest are perpendicular and overlay in the X direction is desired, then a target such as in FIG. 23 can be created or a target can incorporate design features from FIG. 23 to enable such overlay to be determined. Where, for example, features of interest are perpendicular and overlay in the Y direction should be measured, then a target such as in FIG. 24 can be created or a target can incorporate design features from FIG. 24 to enable such overlay to be determined.

Where appropriate and in many cases, cuts/protrusions on the lines of a line space pattern can be used as a means to break symmetry in X and/or Y directions to enable respective overlays to be determined. In an embodiment, the cuts/protrusions are comparable in terms of CD and/or pitch as associated features in the device pattern. But, in an embodiment, the location of the cuts/protrusions should be such that the unit cell is symmetrical at a nominal configuration. In an embodiment, the cuts/protrusions and/or structures of the unit cell are selected to make the unit cell as small as possible.

In an embodiment, the target need not need follow exactly all the process steps of the device (for example, one or more process steps of the device can be bypassed in forming the target if for example those steps are difficult to model). However, the process differences between the device and the target should not impact overlay for the features/layers under consideration.

When both overlay in the X direction and overlay in the Y direction are desired from a same target, a vertical shift of the cut should not change the symmetry with respect to the Y axis and a horizontal shift of the structures should not change the symmetry with respect to the X axis. This helps ensure that X and Y direction overlays are decoupled in their determination from the redirected radiation from the target.

In an embodiment, if one of the layers is processed with LELE, different targets could be used to decouple the overlay from each of the lithography steps. If two layers are processed with LELE, then, for example, four targets could be used.

In an embodiment, where the overlay sensitivity of the target allows it, overlay between more than two layers can be combined in the same target (e.g., a target like that in FIG. 27). This would be more space-efficient, but there could be a loss of accuracy due to, e.g., cross-talk or inaccuracy in the modeling due to the higher complexity of the target.

In an embodiment, the target should have a clearance area and a patterned area with a pattern of similar density as the device. In an embodiment, the clearance and patterned areas around the target can be, for example, at least 0.2 µm of clearance area and/or at least 2 µm of patterned area.

With a nominal target design, various evaluation steps can be performed to tune the nominal target design and/or determine whether the nominal target design will be suitable. So, for example, besides design of a target to satisfy the overlay behavior of device features, the design of the target can be analyzed in view of printability (e.g., the ability of the target to be created as part of a patterning process), detectability (e.g., how good a signal is produced by the target), robustness (e.g., how stable the target is to variation occurring in a patterning process), and/or device matching (e.g., how representative of the overlay of the device is a determine of overlay from the target).

So, at 3110, a device matching can be performed to determine that overlay measured from the target is representative of the overlay of the device. This can be performed by using a simulator or mathematical model to determine whether a simulated or modeled overlay of interest of the device matches (e.g. within a threshold) the corresponding simulated or modeled overlay of interest of the target design. In an embodiment, the matching can be performed for a lithographic step of the patterning process (e.g., intrafield match). In an embodiment, the matching can be performed for an etch step of the patterning process (e.g., interfield match). If there isn't a sufficient match, the target design can be, e.g., abandoned or modified (wherein the modification can comprise a change in pitch of features of the target, a change in CD of features of the target, a change in material of structures of the target, etc.)

At 3120, a detectability evaluation can be performed to determine how good a signal is produced by the target design. This can be performed by using a simulator or mathematical model to determine to expected signal from the target design and whether it meets a threshold. In an embodiment, this can involve evaluation of the sensitivity of the target to overlay, such as any of the sensitivities (e.g., a Jacobian) as discussed herein. In an embodiment, the evaluation can consider the pupil intensity (e.g., root mean square of pupil intensity), stack sensitivity and/or diffraction efficiency of the target design and evaluate it against a threshold. If there isn't a sufficient match, the target design can be, e.g., abandoned or modified (wherein the modification can comprise a change in pitch of features of the target, a change in CD of features of the target, a change in material of structures of the target, etc.). In an embodiment, an iteration is performed with steps 3110 and 3120 until the respective thresholds are met.

At 3130, a printability evaluation can be performed to determine the feasibility of the target to be created as part of a patterning process. This can be performed by using a simulator or mathematical model to determine whether the target design will sufficiently be produced on the substrate (e.g., crosses or meets a threshold). If there isn't sufficient printability, the target design can be, e.g., abandoned or modified (wherein the modification can comprise a change in pitch of features of the target, a change in CD of features of the target, a change in material of structures of the target, etc.).

At 3140, a robustness evaluation can be performed to determine how stable the target is to variation occurring in a patterning process. This can be performed by using a simulator or mathematical model to determine whether the target design will be sensitive (e.g., crosses or meets a threshold) to variations occurring in the patterning process and thus produce inaccurate results. For example, the evaluation can determine the orthogonality of the target results to process perturbations by, e.g., introducing perturbations in the simulator or model. If there isn't sufficient robustness, the target design can be, e.g., abandoned or modified (wherein the modification can comprise a change in pitch of features of the target, a change in CD of features of the target, a change in material of structures of the target, etc.).

At 3150, the target can be created by a patterning process for verification of the target. A patterning process printing the target can be set to induce various know overlay to the target and then the targets can be measured using the techniques herein to determine overlay. The set overlay can then be compared to the obtained overlay. If there isn't sufficient matching (e.g., crosses or meets a threshold), the target design can be, e.g., abandoned or modified (wherein the modification can comprise a change in pitch of features of the target, a change in CD of features of the target, a change in material of structures of the target, etc.).

The determined patterning process parameter value (e.g., overlay value) and the techniques herein can be used for numerous purposes. For example, significant aspects to enabling a patterning process include developing the process itself, setting it up for monitoring and control and then actually monitoring and controlling the process itself (e.g., predicting a chance of a defect based on the patterning process parameter value). The patterning process parameter value and the techniques herein can be used in any of these aspects. Further, assuming a configuration of the fundamentals of the patterning process, such as the patterning device pattern(s), the resist type(s), post-lithography process steps (such as the development, etch, etc.), it is desirable to setup the apparatus in the patterning process for transferring the pattern onto the substrates, develop one or more metrology targets to monitor the process, setup up a metrology process to measure the metrology targets and implement a process of monitoring and/or controlling the process based on measurements. The patterning process parameter value and the techniques herein can be used in any of those processes.

While discussion in this application considers an embodiment of a metrology process and metrology target designed to measure overlay of a device being formed on a substrate, the embodiments herein are equally applicable to other metrology processes and targets, such as process and targets to measure various other asymmetries in symmetrical structures, such as sidewall angle asymmetry, asymmetry in bottom floor tilt angle, asymmetries in CD, etc. Accordingly, the references herein to overlay metrology targets, overlay data, etc. should be considered as suitably modified to enable other kinds of metrology processes and targets.

In an embodiment, there is provided a method of determining a parameter of a patterning process, the method comprising: illuminating a substrate with a radiation beam such that a beam spot on the substrate is filled with one or more physical instances of a unit cell, the unit cell having geometric symmetry at a nominal value of the parameter; detecting primarily zeroth order radiation redirected by the one or more physical instances of the unit cell using a detector; and determining, by a hardware computer system, a non-nominal value of the parameter of the unit cell from values of an optical characteristic of the detected radiation.

In an embodiment, the parameter comprises overlay. In an embodiment, the method comprises determining an edge placement error based on the parameter. In an embodiment, optical characteristic values from pixels of the detected radiation with greater sensitivity to a physical effect measured by the parameter provide a greater contribution to determining the non-nominal value of the parameter than optical characteristic values from other pixels of the detected radiation with lower sensitivity to the physical effect measured by the parameter. In an embodiment, the values of the optical characteristic form a pupil representation. In an embodiment, the values of the optical characteristic are processed to subtract optical characteristic values across an axis of symmetry so as to reduce or eliminate the optical characteristic values of a symmetric optical characteristic distribution of the detected radiation. In an embodiment, the non-nominal value of the parameter is determined using a summation for a plurality of pixels of the detected radiation of an optical characteristic value for each pixel multiplied by an associated weighting for that pixel. In an embodiment, the optical characteristic is intensity and/or phase. In an embodiment, the one or more physical instances of the unit cell is a device structure. In an embodiment, the one or more physical instances of the unit cell is a non-device structure within a substrate die comprising a device structure. In an embodiment, the radiation is detected after an etching process to produce the one or more physical instances of the unit cell. In an embodiment, the parameter comprises overlay and the method further comprises determining, from the optical characteristic values, a value of a first overlay separately from a second overlay that is also obtainable from the same optical characteristic values, wherein the first overlay is in a different direction than the second overlay or between a different combination of parts of the unit cell than the second overlay.

In an embodiment, there is provided a method of determining a parameter of a patterning process, the method comprising: obtaining a detected pupil representation of radiation redirected by a structure having geometric symmetry at a nominal physical configuration, wherein a different physical configuration of the structure than the nominal physical configuration causes an asymmetric optical characteristic distribution in the pupil representation; processing the pupil representation to subtract optical characteristic values across an axis of symmetry so as to reduce or eliminate the optical characteristic values of a symmetric optical characteristic distribution in the pupil representation; and determining, by a hardware computer system, a value of the patterning process parameter based on optical characteristic values from the processed pupil representation.

In an embodiment, the patterning process parameter is overlay and the different physical configuration is a shift of at least part of the structure relative another part of the structure. In an embodiment, the pupil representation is of primarily zeroth order radiation. In an embodiment, optical characteristic values from pixels of the processed pupil representation with greater sensitivity to the different physical configuration provide a greater contribution to determining the value of the patterning process parameter than optical characteristic values from other pixels of the detected radiation with lower sensitivity to the different physical configuration. In an embodiment, the value of the patterning process parameter is determined using a summation for a plurality of pixels of the pupil representation of an optical characteristic value for each pixel multiplied by an associated weighting for that pixel. In an embodiment, the optical characteristic is intensity and/or phase. In an embodiment, the structure is a device structure. In an embodiment, the structure is a non-device structure within a substrate die comprising a device structure. In an embodiment, the radiation is detected after an etching process to produce the structure. In an embodiment, the determining comprises determining, from the optical characteristic values, a value of a first patterning process parameter of the structure separately from a value of the a second patterning process parameter, that is also obtainable from the same optical characteristic values, for the structure, wherein the first patterning process parameter is in a different direction than the second patterning process parameter or between a different combination of parts of the structure than the second patterning process parameter.

In an embodiment, there is provided a method of determining a parameter of a patterning process, the method comprising: obtaining a detected representation of radiation redirected by a structure having geometric symmetry at a nominal physical configuration, wherein the detected representation of the radiation was obtained by illuminating a substrate with a radiation beam such that a beam spot on the substrate was filled with the structure; and determining, by a hardware computer system, a value of the patterning process parameter based on optical characteristic values from an asymmetric optical characteristic distribution portion of the detected radiation representation with higher weight than another portion of the detected radiation representation, the asymmetric optical characteristic distribution arising from a different physical configuration of the structure than the nominal physical configuration.

In an embodiment, the patterning process parameter is overlay and the different physical configuration is a shift of at least part of the structure relative another part of the structure. In an embodiment, the detected radiation representation is a pupil representation. In an embodiment, the detected radiation was primarily zeroth order radiation. In an embodiment, the detected radiation representation is processed to subtract optical characteristic values across an axis of symmetry so as to reduce or eliminate the optical characteristic values of a symmetric optical characteristic distribution of the detected radiation representation. In an embodiment, the value of the patterning process parameter is determined using a summation for a plurality of pixels of the detected radiation representation of an optical characteristic value for each pixel multiplied by an associated weighting for that pixel. In an embodiment, the optical characteristic is intensity and/or phase. In an embodiment, the structure is a device structure. In an embodiment, the structure is a non-device structure within a substrate die comprising a device structure. In an embodiment, the weighting is configured to cause a first type of the patterning process parameter to be determined for the different physical configuration separately from a second type of the patterning process parameter that is also obtainable from the same optical characteristic values, wherein the first type of patterning process parameter is in a different direction than the second type of patterning process parameter or between a different combination of parts of the unit cell than the second type of patterning process parameter. In an embodiment, the method further comprises a weighting configured to cause the second type of the patterning process parameter to be determined for the different physical configuration.

In an embodiment, there is provided a method of determining a parameter of a patterning process, the method comprising: obtaining a detected representation of radiation redirected by a structure having geometric symmetry at a nominal value of the parameter, wherein the detected representation of the radiation was obtained by illuminating a substrate with a radiation beam such that a beam spot on the substrate was filled with the structure and wherein, at a non-nominal value of the parameter, the physical configuration of the structure causes an asymmetric optical characteristic distribution in the detected radiation representation; and determining, by a hardware computer system, a non-nominal value of the parameter of the structure based on a summation for a plurality of pixels of the detected radiation representation of an optical characteristic value for each pixel multiplied by an associated weighting for that pixel, wherein the weighting for pixels in the asymmetric optical characteristic distribution are different than the weighting for pixels in a symmetric optical characteristic distribution portion of the detected radiation representation.

In an embodiment, the parameter comprises overlay. In an embodiment, the detected radiation representation is a pupil representation. In an embodiment, the detected radiation was primarily zeroth order radiation. In an embodiment, the detected radiation representation is processed to subtract optical characteristic values across an axis of symmetry so as to reduce or eliminate the optical characteristic values of the symmetric optical characteristic distribution of the detected radiation representation. In an embodiment, the optical characteristic is intensity and/or phase. In an embodiment, the structure is a device structure. In an embodiment, the structure is a non-device structure within a substrate die comprising a device structure. In an embodiment, the parameter comprises overlay and the weighting is configured to separately determine a first type of overlay for the structure from a second type of overlay for the structure, that is also obtainable from the same optical characteristic values. In an embodiment, the method further comprises a weighting configured to separately determine, from the same optical characteristic values, the second type of overlay for the structure from the first type of overlay for the structure.

In an embodiment, there is provided a method comprising: obtaining a detected representation of radiation redirected by a structure that has geometric symmetry at a nominal physical configuration, wherein a different physical configuration of the structure than the nominal physical configuration causes an asymmetric optical characteristic distribution in the detected representation and a patterning process parameter measures change in the physical configuration; and determining, by a hardware computer system, a value of the patterning process parameter at the different physical configuration using a reconstruction process that processes optical characteristic values derived from the detected representation.

In an embodiment, the method further comprises processing the representation to subtract optical characteristic values across an axis of symmetry so as to reduce or eliminate the optical characteristic values of a symmetric optical characteristic distribution in the representation and the determining comprises determining the value of the patterning process parameter using a reconstruction process that processes optical characteristic values derived from the processed detected representation. In an embodiment, the reconstruction process involves using a mathematical model of the structure to generate a simulated representation of radiation redirected by the structure for comparison with the optical characteristic values derived from the detected representation. In an embodiment, the mathematical model is based on a profile of the structure derived from measurements of instances of the structure. In an embodiment, the reconstruction process involves comparing the optical characteristic values derived from the detected representation against a library of simulated representations of radiation redirected by the structure.

In an embodiment, there is provided a method comprising: obtaining a detected representation of radiation redirected by a structure that has geometric symmetry at a nominal physical configuration, wherein a different physical configuration of the structure than the nominal physical configuration causes an asymmetric optical characteristic distribution in the detected representation and a patterning process parameter measures change in the physical configuration; and determining, by a hardware computer system, a value of the patterning process parameter at the different physical configuration using a non-linear solver that processes optical characteristic values derived from the detected representation.

In an embodiment, the non-linear solver solves a function wherein the one or more variable terms thereof consist only of one or more variable terms having the patterning process parameter as the variable to an odd power, and/or one or more variable terms having the patterning process parameter as the variable in combination with another parameter of the structure as a variable. In an embodiment, the method further comprises processing the representation to subtract optical characteristic values across an axis of symmetry so as to reduce or eliminate the optical characteristic values of a symmetric optical characteristic distribution in the representation and the determining the value of the patterning process parameter using a non-linear solver that processes optical characteristic values derived from the processed detected representation.

In an embodiment, there is provided a method of configuring a parameter determination process, the method comprising: obtaining a mathematical model of a structure, the mathematical model configured to predict an optical response when illuminating the structure with a radiation beam and the structure having geometric symmetry at a nominal physical configuration; using, by a hardware computer system, the mathematical model to simulate a perturbation in the physical configuration of the structure of a certain amount to determine a corresponding change of the optical response in each of a plurality of pixels to obtain a plurality of pixel sensitivities; and based on the pixel sensitivities, determining a plurality of weights for combination with measured pixel optical characteristic values of the structure on a substrate to yield a value of a parameter associated with change in the physical configuration, each weight corresponding to a pixel.

In an embodiment, the parameter is overlay and the different physical configuration is a shift of at least part of the structure relative another part of the structure. In an embodiment, the optical response comprises the optical characteristic in the form of a pupil image. In an embodiment, the optical response is of primarily zeroth order radiation. In an embodiment, the determining the weights comprises using a Jacobian matrix. In an embodiment, the determining the weights comprises using a Hessian matrix. In an embodiment, the determining the weights comprises using a Moore-Penrose pseudoinverse. In an embodiment, the weights are configured such that the value of the parameter can be determined using a summation for a plurality of pixels of the detected radiation representation of an optical characteristic value for each pixel multiplied by the weight of the plurality of weights associated with that pixel. In an embodiment, the optical characteristic is intensity and/or phase. In an embodiment, the structure is a device structure. In an embodiment, the structure is a non-device structure within a substrate die comprising a device structure. In an embodiment, the method further comprises determining a set of measurement settings for obtaining the measured pixel optical characteristic values, the set of measurement settings corresponding to the plurality of weights. In an embodiment, the set of measurement settings comprises one or more selected from: a wavelength of a measurement beam, a polarization of the measurement beam, a dose of the measurement beam, and/or a number of optical characteristic readings taken by a detector sensor of a particular one illumination of the structure. In an embodiment, the obtaining the mathematical model comprises performing CD measurements on one or more substrates comprising the structure and calibrating the mathematical model against the CD measurements to obtain a nominal profile of the structure for perturbation of the physical configuration of the structure. In an embodiment, the method further comprises measuring optical characteristic values of radiation redirected by a plurality of structures with known different physical configurations and associated expected values of the parameter; combining the weights and the measured optical characteristic values to determine a value of the parameter for each of the known different physical configurations; and evaluating the determined values of the parameter with the expected values of the parameter; and responsive to the evaluation, adjusting a parameter of the mathematical model and/or adjusting one or more of the weights.

In an embodiment, there is provided a method comprising: using, by a hardware computer system, a mathematical model of a structure to predict an optical response when illuminating the structure with a radiation beam, the structure having geometric symmetry at a nominal physical configuration and a patterning process parameter measures change in the physical configuration; and using, by the hardware computer system, a non-linear solver to determine, based on the optical response, coefficients of a mathematical function of the patterning process parameter as a variable thereof, the determined coefficients and the function for use with a measured representation of detected radiation from the structure, on a substrate, at a different physical configuration than the nominal physical configuration which causes an asymmetric optical characteristic distribution in the detected representation, to determine a value of the patterning process parameter for the measured structure. In an embodiment, the method comprises using the mathematical model to simulate a perturbation in the physical configuration of the structure of a certain amount to determine a corresponding change of the optical response and wherein determining the coefficients uses the changed optical response. In an embodiment, the method further comprises obtaining a detected representation of radiation redirected by the structure on the substrate having the different physical configuration, and determining a value of the patterning process parameter using a non-linear solver that processes optical characteristic values derived from the detected representation and uses the determined coefficients. In an embodiment, the non-linear solver solves a function wherein the one or more variable terms thereof consist only of one or more variable terms having the patterning process parameter as the variable to an odd power, and/or one or more variable terms having the patterning process parameter as the variable in combination with another parameter of the structure as a variable. In an embodiment, the method further comprises processing the optical response to subtract optical characteristic values across an axis of symmetry so as to reduce or eliminate the optical characteristic values of a symmetric optical characteristic distribution in the optical response and the determining the coefficients is based on optical characteristic values derived from the processed optical response. In an embodiment, the mathematical model uses a nominal profile of the structure derived from calibration of the mathematical model against CD measurements to obtain the nominal profile of the structure. In an embodiment, the coefficients comprise a set of coefficients for each of a plurality of pixels in the optical response.

In an embodiment, there is provided a method, comprising: obtaining measurement results for different instances of a structure generated by a patterning process, wherein measurement results are obtained at each of a plurality of different set values of a patterning process parameter that measures a change in the physical configuration of the structure and each different set value of the patterning process parameter corresponds to a physical configuration of the structure that causes an asymmetric optical characteristic distribution in a radiation representation; and determining, by a hardware computer system, a plurality of data-driven values that correspond to weights for combination with measured optical characteristic values of a further instance of the structure to yield a value of the patterning process parameter, wherein the set values and the measurement results are used in an objective or merit function or a machine learning algorithm, to determine the data-driven values.

In an embodiment, the method further comprises using the determined data-driven values to modify a mathematical model of the structure, and using the mathematical model to derive the weights for combination with measured optical characteristic values of the further instance of the structure. In an embodiment, the method further comprises using a Hessian matrix of the mathematical model to update values of a nominal profile of the structure embodied in the mathematical model. In an embodiment, the method further comprises using a Hessian matrix of the modified mathematical model to compute the weights for combination with measured optical characteristic values of the further instance of the structure. In an embodiment, the measurement results are a plurality of detected representations of radiation redirected by the different instances of the structure. In an embodiment, the detected representations of the radiation were obtained by illuminating a substrate with a radiation beam such that a beam spot on the substrate was filled with the structure. In an embodiment, the method further comprises generating one or more synthetic representations of radiation expected to be redirected by an instance of the structure and expected for a variation in the patterning process, and wherein the determining the plurality of data-driven values is based on the set values, the measurement results and the one or more synthetic representations. In an embodiment, the one or more synthetic representations of radiation are generated by using a Hessian matrix of the mathematical model. In an embodiment, the one or more synthetic representations of radiation are generated using a non-linear simulation. In an embodiment, the patterning process parameter is overlay. In an embodiment, the method further comprises determining the value of the patterning process parameter for the further instance of the structure based on the plurality of weights in combination with measured optical characteristic values of the further instance of the structure. In an embodiment, each of the measured optical characteristic values corresponds to a pixel in a pupil representation and comprising determining the value of the patterning process parameter for the further instance based on a summation for a plurality of pixels of the pupil representation of a measured optical characteristic value for each pixel multiplied by an associated weighting for that pixel, wherein the weighting for pixels in an asymmetric optical characteristic distribution portion of the pupil representation are different than the weighting for pixels in a symmetric optical characteristic distribution portion of the pupil representation.

In an embodiment, there is provided a method of determining a parameter of a patterning process, the method comprising: obtaining a detected representation of radiation redirected by one or more physical instances of a unit cell, wherein the unit cell has geometric symmetry at a nominal value of the parameter and wherein the detected representation of the radiation was obtained by illuminating a substrate with a radiation beam such that a beam spot on the substrate was filled with the one or more physical instances of the unit cell; and determining, by a hardware computer system and from optical characteristic values from the detected radiation representation, a value of a first type of the parameter for the unit cell separately from a second type of the parameter for the unit cell that is also obtainable from the same optical characteristic values, wherein the first type of the parameter is for a different direction than the second type of the parameter or for between a different combination of parts of the unit cell than the second type of the parameter.

In an embodiment, the parameter comprises overlay. In an embodiment, the first and second types of parameter are for different directions and for a same first and second parts of the unit cell. In an embodiment, the first type of parameter is for between a different combination of parts of the unit cell than the second type of parameter. In an embodiment, the method further comprises determining, from the same optical characteristic values as the value of the first type of parameter is determined, a value of the second type of parameter. In an embodiment, the determining the value of first type of parameter uses a set of weights for pixel optical characteristic values. In an embodiment, the value of the first type of parameter is determined using a summation for a plurality of pixels of the detected radiation representation of an optical characteristic value for each pixel multiplied by an associated weighting for that pixel. In an embodiment, optical characteristic values from pixels of the detected radiation representation with greater sensitivity to a physical effect measured by the parameter provide a greater contribution to determining the value of the first type of parameter than optical characteristic values from other pixels of the detected radiation with lower sensitivity to the physical effect measured by the parameter. In an embodiment, the detected radiation was primarily zeroth order radiation. In an embodiment, the detected radiation representation is a pupil representation. In an embodiment, the detected radiation representation is processed to subtract optical characteristic values across an axis of symmetry so as to reduce or eliminate the optical characteristic values of a symmetric optical characteristic distribution of the detected radiation representation. In an embodiment, the optical characteristic is intensity and/or phase. In an embodiment, the structure is a device structure. In an embodiment, the structure is a non-device structure within a substrate die comprising a device structure. In an embodiment, the detected radiation representation was detected after an etching process to produce the structure.

In an embodiment, there is provided a method of determining a parameter of a patterning process, the method comprising: obtaining a detected representation of radiation redirected by one or more physical instances of a unit cell, wherein the unit cell has geometric symmetry at a nominal value of the parameter and wherein the detected representation of the radiation was obtained by illuminating a substrate with a radiation beam such that a beam spot on the substrate was filled with the one or more physical instances of the unit cell; and determining, by a hardware computer system and from optical characteristic values from the detected radiation representation, a value of the parameter for between a first part of the unit cell and a second part of the unit cell separately from a value of the parameter, that is also obtainable from the same optical characteristic values, for between the second part of the unit cell and a third part of the unit cell or between the third part of the unit cell and a fourth part of the unit cell.

In an embodiment, the parameter comprises overlay. In an embodiment, the method further comprises determining, from the optical characteristic values, a value of the parameter for between the second and third parts of the or each unit cell or between the third and fourth parts of the or each unit cell, separately from a value of the parameter for between the first and second parts of the or each unit cell. In an embodiment, the determining the parameter value uses a set of weights for pixel optical characteristic values. In an embodiment, the parameter value is determined using a summation for a plurality of pixels of the detected radiation representation of an optical characteristic value for each pixel multiplied by an associated weighting for that pixel. In an embodiment, optical characteristic values from pixels of the detected radiation representation with greater sensitivity to a physical effect measured by the parameter provide a greater contribution to determining the parameter value than optical characteristic values from other pixels of the detected radiation representation with lower sensitivity to the physical effect measured by the parameter. In an embodiment, the detected radiation was primarily zeroth order radiation. In an embodiment, the detected radiation representation is a pupil representation. In an embodiment, the detected radiation representation is processed to subtract optical characteristic values across an axis of symmetry so as to reduce or eliminate the optical characteristic values of a symmetric optical characteristic distribution of the detected radiation representation. In an embodiment, the optical characteristic is intensity and/or phase. In an embodiment, the structure is a device structure. In an embodiment, the structure is a non-device structure within a substrate die comprising a device structure. In an embodiment, the radiation is detected after an etching process to produce the structure.

In an embodiment, there is provided a method of configuring a parameter determination process, the method comprising: obtaining a mathematical model of a structure on a substrate, the model configured to predict an optical response when illuminating the structure with a radiation beam and the structure having geometric symmetry at a nominal parameter value; using, by a hardware computer system, the model to simulate a change of a first type of the parameter of the structure to determine a corresponding first change of the optical response in each of a plurality of pixels and to a simulate a change of a second type of the parameter to determine a corresponding second change of the optical response in each of the plurality of pixels, wherein the first type of parameter is for a different direction than the second type of parameter or for between a different combination of parts of the structure than the second type of parameter; and based on the first and second changes in the optical response, determining a plurality of weights for combination with measured pixel optical characteristic values to yield a value of first type of parameter from same measured optical characteristic values separately from the second type of parameter.

In an embodiment, the parameter comprises overlay. In an embodiment, the plurality of weights for the first type of parameter are determined using the result of a back projection of a vector corresponding to the change in the first type of parameter in terms of the first change in optical responses of the plurality of pixels against an orthogonal to a vector corresponding to the change in the second type of parameter in terms of the second change in optical responses of the plurality of pixels. In an embodiment, the method further comprises, based on the first and second changes in the optical response, determining a plurality of weights for combination with measured pixel optical characteristic values to yield a value of second type of parameter from the measured optical characteristic values separately from the first type of parameter. In an embodiment, the plurality of weights for the second type of parameter are determined using the result of a back projection of a vector corresponding to the change in the second type of parameter in terms of the second change in optical responses of the plurality of pixels against an orthogonal to a vector corresponding to the change in the first type of parameter in terms of the first change in optical responses of the plurality of pixels. In an embodiment, the weights are configured such that the first and/or second types of parameter is determined using a summation for a plurality of pixels of the detected radiation representation of an optical characteristic value for each pixel multiplied by an associated weight for that pixel. In an embodiment, the optical response comprises the optical characteristic in the form of a pupil image. In an embodiment, the optical response is of primarily zeroth order radiation. In an embodiment, the optical characteristic is intensity and/or phase. In an embodiment, the structure is a device structure. In an embodiment, the structure is a non-device structure within a substrate die comprising a device structure.

In an embodiment, there is provided a metrology target comprising: a first structure arranged to be created by a first patterning process; and a second structure arranged to be created by a second patterning process, wherein the first structure and/or second structure is not used to create a functional aspect of a device pattern, and wherein the first and second structures together form one or more instances of a unit cell, the unit cell having geometric symmetry at a nominal physical configuration and wherein the unit cell has a feature that causes, at a different physical configuration than the nominal physical configuration due to a relative shift in pattern placement in the first patterning process, the second patterning process and/or another patterning process, an asymmetry in the unit cell.

In an embodiment, the first structure comprises a structure of a first dimension and/or material and the second structure comprises a structure of a second dimension or material, wherein the feature comprises the first dimension and/or material being different than the second dimension and/or material. In an embodiment, the first structure comprises structures arranged in an array in a first direction and at least one such structure comprises a plurality of sub-structures separated by voids arranged along a second direction substantially perpendicular to the first direction and/or the second structure comprises structures arranged in an array in a first direction and at least one such structure comprises a plurality of sub-structures separated by voids arranged along a second direction substantially perpendicular to the first direction, wherein the feature comprises the voids of the first structure and/or the second structure. In an embodiment, the voids of the first structure and/or the second structure are produced using a different patterning process than the first and second patterning processes. In an embodiment, the first structure comprises the voids and the second structure comprises the voids. In an embodiment, the voids of the first structure have a different pitch than the voids of the second structure. In an embodiment, at least one void of the first structure lines up with at least one void of the second structure at the nominal physical configuration. In an embodiment, the first structure comprises closed curve structures and the second structure comprises close curve structures. In an embodiment, the structures are arranged in the first array in a direction substantially perpendicular to a direction in which the structures are arranged in the second array or in which the structures are arranged in a third array of structures.

In an embodiment, there is provided a computer program product comprising a computer non-transitory readable medium having a data structure recorded thereon, the data structure corresponding to a metrology target as described herein. In an embodiment, there is provided a reticle comprising a pattern corresponding to a metrology target as described herein.

In an embodiment, there is provided a method comprising: creating a first structure for a metrology target, the first structure to be created by a first patterning process that creates a corresponding device feature of a device; creating a second structure for the metrology target, the second structure to be created by a second patterning process that creates a further corresponding device feature of device, wherein the first and second structures together form one or more instances of a unit cell, the unit cell having geometric symmetry at a nominal physical configuration; and introducing a feature in the metrology target that causes, at a different physical configuration than the nominal physical configuration due to a relative shift in location of device features in the device from an expected location of the device features in the device, an asymmetry in the unit cell.

In an embodiment, a feature of the first structure has a substantially same dimension and/or pitch as the corresponding feature of the device and/or a feature of the second structure has a substantially same dimension and/or pitch as the corresponding feature of the device. In an embodiment, the feature in the metrology target causes a first type of asymmetry in the unit cell for a relative shift in a first direction and causes a second different type of asymmetry in the unit cell for a relative shift in a second different direction. In an embodiment, the method further comprises evaluating one or more selected from: printability of the metrology target, detectability of the metrology target, robustness of the metrology target to process variations, and/or matching of the metrology target to a device pattern. In an embodiment, the method comprises iteratively evaluating matching of the metrology target to a device pattern and detectability of the metrology target.

In an embodiment, there is provided a method comprising: measuring radiation redirected by a metrology as described herein transferred to a substrate using a patterning process to determine a value of a parameter of the patterning process. In an embodiment, the parameter comprises overlay and/or edge placement error.

Figure 32:
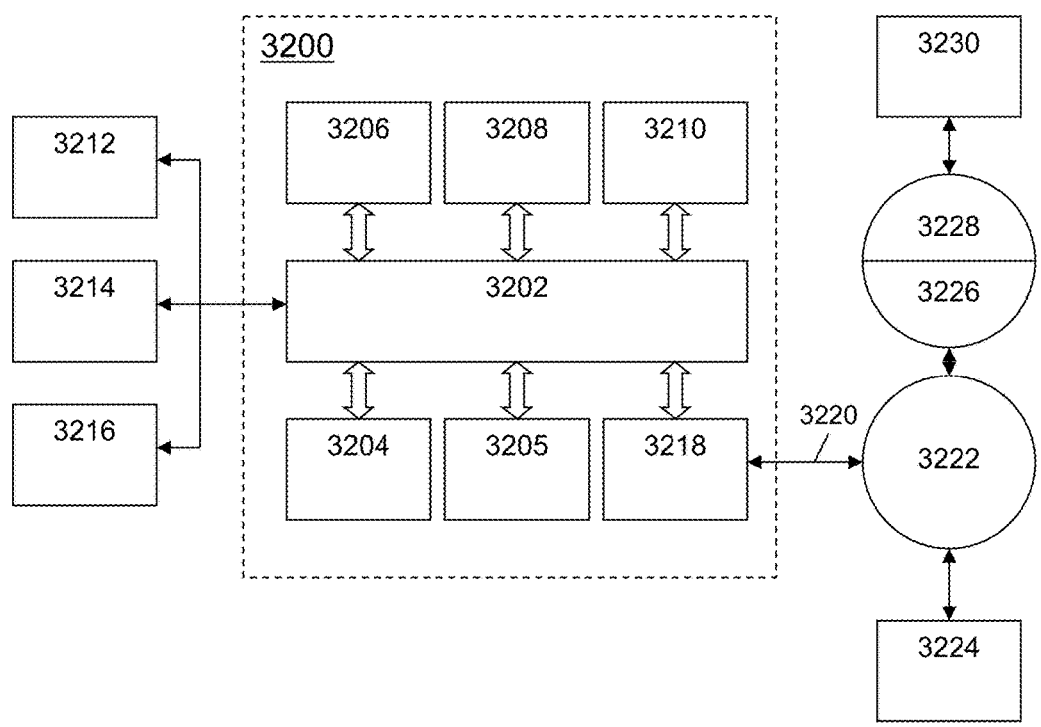
FIG. 32 schematically depicts a computer system which may implement embodiments of this disclosure.

Referring to FIG. 32, a computer system 3200 is shown. The computer system 3200 includes a bus 3202 or other communication mechanism for communicating information, and a processor 3204 (or multiple processors 3204 and 3205) coupled with bus 3202 for processing information. Computer system 3200 also includes a main memory 3206, such as a random access memory (RAM) or other dynamic storage device, coupled to bus 3202 for storing information and instructions to be executed by processor 3204. Main memory 3206 also may be used for storing temporary variables or other intermediate information during execution of instructions to be executed by processor 3204. Computer system 3200 further includes a read only memory (ROM) 3208 or other static storage device coupled to bus 3202 for storing static information and instructions for processor 3204. A storage device 3210, such as a magnetic disk or optical disk, is provided and coupled to bus 3202 for storing information and instructions.

Computer system 3200 may be coupled via bus 3202 to a display 3212, such as a cathode ray tube (CRT) or flat panel or touch panel display for displaying information to a computer user. An input device 3214, including alphanumeric and other keys, is coupled to bus 3202 for communicating information and command selections to processor 3204. Another type of user input device is cursor control 3216, such as a mouse, a trackball, or cursor direction keys for communicating direction information and command selections to processor 3204 and for controlling cursor movement on display 3212. This input device typically has two degrees of freedom in two axes, a first axis (e.g., x) and a second axis (e.g., y), that allows the device to specify positions in a plane. A touch panel (screen) display may also be used as an input device.

The computer system 3200 may be suitable to function as a processing unit herein in response to processor 3204 executing one or more sequences of one or more instructions contained in main memory 3206. Such instructions may be read into main memory 3206 from another computer-readable medium, such as storage device 3210. Execution of the sequences of instructions contained in main memory 3206 causes processor 3204 to perform a process described herein. One or more processors in a multi-processing arrangement may also be employed to execute the sequences of instructions contained in main memory 3206. In alternative embodiments, hard-wired circuitry may be used in place of or in combination with software instructions. Thus, embodiments are not limited to any specific combination of hardware circuitry and software.

The term "computer-readable medium" as used herein refers to any medium that participates in providing instructions to processor 3204 for execution. Such a medium may take many forms, including but not limited to, non-volatile media, volatile media, and transmission media. Non-volatile media include, for example, optical or magnetic disks, such as storage device 3210. Volatile media include dynamic memory, such as main memory 3206. Transmission media include coaxial cables, copper wire and fiber optics, including the wires that comprise bus 3202. Transmission media can also take the form of acoustic or light waves, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 3204 for execution. For example, the instructions may initially be borne on a magnetic disk of a remote computer. The remote computer can load the instructions into its dynamic memory and send the instructions over a telephone line using a modem. A modem local to computer system 3200 can receive the data on the telephone line and use an infrared transmitter to convert the data to an infrared signal. An infrared detector coupled to bus 3202 can receive the data carried in the infrared signal and place the data on bus 3202. Bus 3202 carries the data to main memory 3206, from which processor 3204 retrieves and executes the instructions. The instructions received by main memory 3206 may optionally be stored on storage device 3210 either before or after execution by processor 3204.

Computer system 3200 may also include a communication interface 3218 coupled to bus 3202. Communication interface 3218 provides a two-way data communication coupling to a network link 3220 that is connected to a local network 3222. For example, communication interface 3218 may be an integrated services digital network (ISDN) card or a modem to provide a data communication connection to a corresponding type of telephone line. As another example, communication interface 3218 may be a local area network (LAN) card to provide a data communication connection to a compatible LAN. Wireless links may also be implemented. In any such implementation, communication interface 3218 sends and receives electrical, electromagnetic or optical signals that carry digital data streams representing various types of information.

Network link 3220 typically provides data communication through one or more networks to other data devices. For example, network link 3220 may provide a connection through local network 3222 to a host computer 3224 or to data equipment operated by an Internet Service Provider (ISP) 3226. ISP 3226 in turn provides data communication services through the worldwide packet data communication network, now commonly referred to as the "Internet" 3228. Local network 3222 and Internet 3228 both use electrical, electromagnetic or optical signals that carry digital data streams. The signals through the various networks and the signals on network link 3220 and through communication interface 3218, which carry the digital data to and from computer system 3200, are exemplary forms of carrier waves transporting the information.

Computer system 3200 can send messages and receive data, including program code, through the network(s), network link 3220, and communication interface 3218. In the Internet example, a server 3230 might transmit a requested code for an application program through Internet 3228, ISP 3226, local network 3222 and communication interface 3218. In accordance with one or more embodiments, one such downloaded application provides for a method as disclosed herein, for example. The received code may be executed by processor 3204 as it is received, and/or stored in storage device 3210, or other non-volatile storage for later execution. In this manner, computer system 3200 may obtain application code in the form of a carrier wave.

An embodiment of the disclosure may take the form of a computer program containing one or more sequences of machine-readable instructions describing a method as disclosed herein, or a data storage medium (e.g. semiconductor memory, magnetic or optical disk) having such a computer program stored therein. Further, the machine readable instruction may be embodied in two or more computer programs. The two or more computer programs may be stored on one or more different memories and/or data storage media.

Any controllers described herein may each or in combination be operable when the one or more computer programs are read by one or more computer processors located within at least one component of the lithographic apparatus. The controllers may each or in combination have any suitable configuration for receiving, processing, and sending signals. One or more processors are configured to communicate with the at least one of the controllers. For example, each controller may include one or more processors for executing the computer programs that include machine-readable instructions for the methods described above. The controllers may include data storage medium for storing such computer programs, and/or hardware to receive such medium. So the controller(s) may operate according the machine readable instructions of one or more computer programs.

Although specific reference may be made in this text to the use of a metrology apparatus in the manufacture of ICs, it should be understood that the metrology apparatus and processes described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or one or more various other tools. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the disclosure in the context of optical lithography, it will be appreciated that the disclosure may be used in other applications, for example nanoimprint lithography, and where the context allows, is not limited to optical lithography. In the case of nanoimprint lithography, the patterning device is an imprint template or mold.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

References herein to crossing or passing a threshold may include something having a value lower than a specific value or lower than or equal to a specific value, something having a value higher than a specific value or higher than or equal to a specific value, something being ranked higher or lower than something else (through e.g., sorting) based on, e.g., a parameter, etc.

References herein to correcting or corrections of an error include eliminating the error or reducing the error to within a tolerance range.

The term "optimizing" and "optimization" as used herein refers to or means adjusting a lithographic apparatus, a patterning process, etc. such that results and/or processes of lithography or patterning processing have more a desirable characteristic, such as higher accuracy of projection of a design layout on a substrate, a larger process window, etc. Thus, the term "optimizing" and "optimization" as used herein refers to or means a process that identifies one or more values for one or more variables that provide an improvement, e.g. a local optimum, in at least one relevant metric, compared to an initial set of one or more values for those one or more variables. "Optimum" and other related terms should be construed accordingly. In an embodiment, optimization steps can be applied iteratively to provide further improvements in one or more metrics.

In an optimization process of a system, a figure of merit of the system or process can be represented as a cost function. The optimization process boils down to a process of finding a set of parameters (design variables) of the system or process that optimizes (e.g., minimizes or maximizes) the cost function. The cost function can have any suitable form depending on the goal of the optimization. For example, the cost function can be weighted root mean square (RMS) of deviations of certain characteristics (evaluation points) of the system or process with respect to the intended values (e.g., ideal values) of these characteristics; the cost function can also be the maximum of these deviations (i.e., worst deviation). The term "evaluation points" herein should be interpreted broadly to include any characteristics of the system or process. The design variables of the system can be confined to finite ranges and/or be interdependent due to practicalities of implementations of the system or process. In the case of a lithographic apparatus or patterning process, the constraints are often associated with physical properties and characteristics of the hardware such as tunable ranges, and/or patterning device manufacturability design rules, and the evaluation points can include physical points on a resist image on a substrate, as well as non-physical characteristics such as dose and focus.

While specific embodiments of the disclosure have been described above, it will be appreciated that the disclosure may be practiced otherwise than as described. For example, the disclosure may take the form of a computer program containing one or more sequences of machine-readable instructions describing a method as disclosed above, or a data storage medium (e.g. semiconductor memory, magnetic or optical disk) having such a computer program stored therein.

In block diagrams, illustrated components are depicted as discrete functional blocks, but embodiments are not limited to systems in which the functionality described herein is organized as illustrated. The functionality provided by each of the components may be provided by software or hardware modules that are differently organized than is presently depicted, for example such software or hardware may be intermingled, conjoined, replicated, broken up, distributed (e.g. within a data center or geographically), or otherwise differently organized. The functionality described herein may be provided by one or more processors of one or more computers executing code stored on a tangible, non-transitory, machine readable medium. In some cases, third party content delivery networks may host some or all of the information conveyed over networks, in which case, to the extent information (e.g., content) is said to be supplied or otherwise provided, the information may be provided by sending instructions to retrieve that information from a content delivery network.

Unless specifically stated otherwise, as apparent from the discussion, it is appreciated that throughout this specification discussions utilizing terms such as "processing," "computing," "calculating," "determining" or the like refer to actions or processes of a specific apparatus, such as a special purpose computer or a similar special purpose electronic processing/computing device.

The reader should appreciate that the present application describes several inventions. Rather than separating those inventions into multiple isolated patent applications, applicants have grouped these inventions into a single document because their related subject matter lends itself to economies in the application process. But the distinct advantages and aspects of such inventions should not be conflated. In some cases, embodiments address all of the deficiencies noted herein, but it should be understood that the inventions are independently useful, and some embodiments address only a subset of such problems or offer other, unmentioned benefits that will be apparent to those of skill in the art reviewing the present disclosure. Due to costs constraints, some inventions disclosed herein may not be presently claimed and may be claimed in later filings, such as continuation applications or by amending the present claims. Similarly, due to space constraints, neither the Abstract nor the Summary of the Invention sections of the present document should be taken as containing a comprehensive listing of all such inventions or all aspects of such inventions.

It should be understood that the description and the drawings are not intended to limit the invention to the particular form disclosed, but to the contrary, the intention is to cover all modifications, equivalents, and alternatives falling within the spirit and scope of the present invention as defined by the appended claims.

Modifications and alternative embodiments of various aspects of the invention will be apparent to those skilled in the art in view of this description. Accordingly, this description and the drawings are to be construed as illustrative only and are for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, certain features may be utilized independently, and embodiments or features of embodiments may be combined, all as would be apparent to one skilled in the art after having the benefit of this description of the invention. Changes may be made in the elements described herein without departing from the spirit and scope of the invention as described in the following claims. Headings used herein are for organizational purposes only and are not meant to be used to limit the scope of the description.

As used throughout this application, the word "may" is used in a permissive sense (i.e., meaning having the potential to), rather than the mandatory sense (i.e., meaning must). The words "include", "including", and "includes" and the like mean including, but not limited to. As used throughout this application, the singular forms "a," "an," and "the" include plural referents unless the content explicitly indicates otherwise. Thus, for example, reference to "an" element or "a" element includes a combination of two or more elements, notwithstanding use of other terms and phrases for one or more elements, such as "one or more." The term "or" is, unless indicated otherwise, non-exclusive, i.e., encompassing both "and" and "or." Terms describing conditional relationships, e.g., "in response to X, Y," "upon X, Y,", "if X, Y," "when X, Y," and the like, encompass causal relationships in which the antecedent is a necessary causal condition, the antecedent is a sufficient causal condition, or the antecedent is a contributory causal condition of the consequent, e.g., "state X occurs upon condition Y obtaining" is generic to "X occurs solely upon Y" and "X occurs upon Y and Z," Such conditional relationships are not limited to consequences that instantly follow the antecedent obtaining, as some consequences may be delayed, and in conditional statements, antecedents are connected to their consequents, e.g., the antecedent is relevant to the likelihood of the consequent occurring. Statements in which a plurality of attributes or functions are mapped to a plurality of objects (e.g., one or more processors performing steps A, B, C, and D) encompasses both all such attributes or functions being mapped to all such objects and subsets of the attributes or functions being mapped to subsets of the attributes or functions (e.g., both all processors each performing steps A-D, and a case in which processor 1 performs step A, processor 2 performs step B and part of step C, and processor 3 performs part of step C and step D), unless otherwise indicated. Further, unless otherwise indicated, statements that one value or action is "based on" another condition or value encompass both instances in which the condition or value is the sole factor and instances in which the condition or value is one factor among a plurality of factors. Unless otherwise indicated, statements that "each" instance of some collection have some property should not be read to exclude cases where some otherwise identical or similar members of a larger collection do not have the property, i.e., each does not necessarily mean each and every.

To the extent certain U.S. patents, U.S. patent applications, or other materials (e.g., articles) have been incorporated by reference, the text of such U.S. patents, U.S. patent applications, and other materials is only incorporated by reference to the extent that no conflict exists between such material and the statements and drawings set forth herein. In the event of such conflict, any such conflicting text in such incorporated by reference U.S. patents, U.S. patent applications, and other materials is specifically not incorporated by reference herein.

The descriptions above are intended to be illustrative, not limiting. Thus, it will be apparent to one skilled in the art that modifications may be made to the disclosure as described without departing from the scope of the claims set out below.

The invention claimed is:

1. A method of determining a parameter of a patterning process, the method comprising:

obtaining a representation of radiation, redirected by a structure having geometric symmetry at a nominal physical configuration, detected by an optical measurement machine with respect to a pupil of the optical measurement machine, wherein the detected representation of the radiation was obtained by illuminating a substrate with a radiation beam such that a beam spot on the substrate was filled with the structure and the detected representation of the radiation comprises a symmetric optical characteristic distribution portion and an asymmetric optical characteristic distribution portion; and determining, by a hardware computer system, a value of the patterning process parameter based on optical characteristic values from the asymmetric optical characteristic distribution portion of the detected radiation representation with higher weight than that of another portion of the detected radiation representation, the asymmetric optical characteristic distribution portion arising from a different physical configuration of the structure than the nominal physical configuration.

2. The method of claim 1, wherein the patterning process parameter is overlay and the different physical configuration is a shift of at least part of the structure relative another part of the structure.

3. The method of claim 1, wherein the detected radiation was primarily zeroth order radiation.

4. The method of claim 1, wherein the detected radiation representation is processed to subtract optical characteristic values across an axis of symmetry so as to reduce or eliminate the optical characteristic values of the symmetric optical characteristic distribution portion of the detected radiation representation.

5. The method of claim 1, wherein the value of the patterning process parameter is determined using a summation for a plurality of pixels of the detected radiation representation of an optical characteristic value for each pixel multiplied by an associated weighting for that pixel.

6. The method of claim 1, wherein the optical characteristic is intensity and/or phase.

7. The method of claim 1, wherein the structure is a device structure.

8. The method of claim 1, wherein the structure is a non-device structure within a substrate die comprising a device structure.

9. The method of claim 1, wherein the weighting is configured to cause a first type of the patterning process parameter to be determined for the different physical configuration separately from a second type of the patterning process parameter that is also obtainable from the same optical characteristic values, wherein the first type of patterning process parameter is in a different direction than the second type of patterning process parameter or between a different combination of parts of a unit cell of the structure than the second type of patterning process parameter.

10. The method of claim 9, further comprising a weighting configured to cause the second type of the patterning process parameter to be determined for the different physical configuration.

11. A computer program product comprising a computer non-transitory computer-readable medium having instructions recorded thereon, the instructions, when executed by a computer system, configured to cause the computer system to at least:
obtain a representation of radiation, redirected by a structure having geometric symmetry at a nominal physical configuration, detected by an optical measurement machine with respect to a pupil of the optical measurement machine, wherein the detected representation of the radiation was obtained by illuminating a substrate with a radiation beam such that a beam spot on the substrate was filled with the structure and the detected representation of the radiation comprises a symmetric optical characteristic distribution portion and an asymmetric optical characteristic distribution portion; and
determine a value of the patterning process parameter based on optical characteristic values from the asymmetric optical characteristic distribution portion of the detected radiation representation with higher weight than that of another portion of the detected radiation representation, the asymmetric optical characteristic distribution portion arising from a different physical configuration of the structure than the nominal physical configuration.

12. The computer program product of claim 11, wherein the patterning process parameter is overlay and the different physical configuration is a shift of at least part of the structure relative another part of the structure.

13. The computer program product of claim 11, wherein the detected radiation was primarily zeroth order radiation.

14. The computer program product of claim 11, wherein the instructions are further configured to process the detected radiation representation to subtract optical characteristic values across an axis of symmetry so as to reduce or eliminate optical characteristic values of the symmetric optical characteristic distribution portion of the detected radiation representation.

15. The computer program product of claim 11, wherein the instructions configured to determine the value of the patterning process parameter are further configured to use a summation for a plurality of pixels of the detected radiation representation of an optical characteristic value for each pixel multiplied by an associated weighting for that pixel.

16. The computer program product of claim 11, wherein the structure is a device structure or is a non-device structure within a substrate die comprising a device structure.

17. The computer program product of claim 11, wherein the weighting is configured to cause a first type of the patterning process parameter to be determined for the different physical configuration separately from a second type of the patterning process parameter that is also obtainable from the same optical characteristic values, wherein the first type of patterning process parameter is in a different direction than the second type of patterning process parameter or between a different combination of parts of a unit cell of the structure than the second type of patterning process parameter.

18. A metrology apparatus for measuring an object of a patterning process, the metrology apparatus comprising the computer program product of claim 11.

19. A method of determining a patterning process parameter of a patterning process, the method comprising:
obtaining a representation of radiation, redirected by a structure having geometric symmetry at a nominal physical configuration, detected by an optical measurement machine, wherein the detected representation of the radiation was obtained by illuminating a substrate with a radiation beam such that a beam spot on the substrate was filled with the structure and the detected representation of the radiation comprises a symmetric optical characteristic distribution portion and an asymmetric optical characteristic distribution portion; and
determining, by a hardware computer system, a value of the patterning process parameter based on optical characteristic values from the asymmetric optical characteristic distribution portion of the detected radiation representation with different weight than that of another portion of the detected radiation representation, wherein the asymmetric optical characteristic distribution portion arises from a different physical configuration of the structure than the nominal physical configuration and the value of the patterning process parameter is determined using a summation for a plurality of pixels of the detected radiation representation of an optical characteristic value for each pixel multiplied by an associated weighting for that pixel.

20. The method of claim 19, wherein the weighting for pixels in the asymmetric optical characteristic distribution portion are different in different parts of the asymmetric optical characteristic distribution portion.

21. The method of claim 19, wherein the patterning process parameter is overlay and the different physical configuration is a shift of at least part of the structure relative another part of the structure.

22. A computer program product comprising a non-transitory computer-readable medium having instructions recorded thereon, the instructions, when executed by a computer system, configured to cause the computer system to at least:
obtain a representation of radiation, redirected by a structure having geometric symmetry at a nominal physical configuration, detected by an optical measurement machine, wherein the detected representation of the radiation was obtained by illuminating a substrate with a radiation beam such that a beam spot on the substrate was filled with the structure and the detected representation of the radiation comprises a symmetric optical characteristic distribution portion and an asymmetric optical characteristic distribution portion; and
determine a value of the patterning process parameter based on optical characteristic values from the asymmetric optical characteristic distribution portion of the detected radiation representation with different weight than that of another portion of the detected radiation representation, wherein the asymmetric optical characteristic distribution portion arises from a different physical configuration of the structure than the nominal physical configuration and the value of the patterning process parameter is determined using a summation for a plurality of pixels of the detected radiation representation of an optical characteristic value for each pixel multiplied by an associated weight for the pixel.

23. The computer program product of claim 22, wherein the weighting for pixels in the asymmetric optical characteristic distribution portion are different in different parts of the asymmetric optical characteristic distribution portion.

24. The computer program product of claim 22, wherein the detected radiation representation is detected with respect to a pupil of the optical measurement machine.

25. The computer program product of claim 22, wherein the detected radiation was primarily zeroth order radiation.

26. The computer program product of claim 22, wherein the instructions are further configured to process the detected radiation representation to subtract optical characteristic values across an axis of symmetry so as to reduce or eliminate optical characteristic values of the symmetric optical characteristic distribution portion of the detected radiation representation.

27. The computer program product of claim 22, wherein the patterning process parameter is overlay and the different physical configuration is a shift of at least part of the structure relative another part of the structure.

28. The computer program product of claim 22, wherein the structure is a device structure or is a non-device structure within a substrate die comprising a device structure.

29. The computer program product of claim 22, wherein the weighting is configured to cause a first type of the patterning process parameter to be determined for the different physical configuration separately from a second type of the patterning process parameter that is also obtainable from the same optical characteristic values, wherein the first type of patterning process parameter is in a different direction than the second type of patterning process parameter or between a different combination of parts of a unit cell of the structure than the second type of patterning process parameter.

* * * * *